US006682923B1

(12) United States Patent
Bentzien et al.

(10) Patent No.: US 6,682,923 B1
(45) Date of Patent: Jan. 27, 2004

(54) THERMOSTABLE ALKALIPHILIC XYLANASE

(75) Inventors: Jörg Bentzien, Pasadena, CA (US); Bassil I. Dahiyat, Los Angeles, CA (US)

(73) Assignee: Xencor, Monrovia, CA (US)

( * ) Notice: Subject to any disclaimer, the term of this patent is extended or adjusted under 35 U.S.C. 154(b) by 0 days.

(21) Appl. No.: 09/570,856

(22) Filed: May 12, 2000

Related U.S. Application Data

(60) Provisional application No. 60/138,156, filed on Jun. 7, 1999, and provisional application No. 60/133,714, filed on May 12, 1999.

(51) Int. Cl.$^7$ .............................. C12N 9/00; C12N 9/24; C12N 9/42; C12N 15/09; C12N 1/20; C12N 15/00; C07H 21/04; C11D 3/00; C11D 7/42

(52) U.S. Cl. ........................ 435/209; 435/183; 435/200; 435/69.1; 435/252.3; 435/320.1; 536/23.2; 510/114; 510/392; 510/515

(58) Field of Search ..................... 435/183, 193, 435/200, 69.1, 252.3, 320.1, 209; 536/23.2; 510/114, 392, 515

(56) References Cited

U.S. PATENT DOCUMENTS

| 5,078,802 A | | 1/1992 | Imanaka et al. ............... 134/42 |
|---|---|---|---|
| 5,306,633 A | | 4/1994 | Gottschalk et al. ......... 435/200 |
| 5,405,769 A | * | 4/1995 | Campbell et al. |
| 5,736,384 A | | 4/1998 | Fukunaga et al. .......... 435/278 |
| 5,759,840 A | | 6/1998 | Sung et al. .................. 435/200 |

FOREIGN PATENT DOCUMENTS

| EP | 0828002 A | 3/1998 |
|---|---|---|
| EP | 828002 A2 * | 3/1998 |
| WO | 94/24270 | 10/1994 |
| WO | 98/47089 | 10/1998 |

OTHER PUBLICATIONS

Coutinho and Henrissat, "The Modular Structure of Cellulases and Other Carbohydrate–Active Enzymes: an Integrated Database Approach," In *Genetcs, Biochemistry and Ecology of Cellulose Degradation*, Ohimay et al., eds. Uni Publishers Co., Tokyo, pp. 15–23 (1999).
Henrissat, "A classification of glycosyl hydrolases based on amino acid sequence similarities", *Biochem, J.* 280:309–316 (1991).
Henrissat and Bairoch, "New families in the classification of glycosyl hydrolases based on amino acid sequence similarities", *Biochem. J.* 293:781–788 (1993).
Henrissat and Bairoch, "Updating the sequence–based classification of glycosyl hydrolases", *Biochem. J.* 316:695–696 (1996).
Davies and Henrissat, "Structures and mechanisms of glycosyl hydrolases", *Structure* 3:853–859 (1995).

Gilkes et al., "Domains in Microbial β–1, 4–Glycanases: Sequence Conservation, Function, and Enzyme Families", *Microbiol. Reviews* 55:303–315 (1991).
Morris, et al., "Cloning of a Family G Xylanase Gene (xynB) from the Extremely Thermophilic Bacterium *Dictyolglomus thermophilum* and Activity of the Gene Product on Kraft Pulp" in, *Enzymes for Pulp and Paper Processing*, eds. Jeffries and Viikari, ACS Symposium Series, vol. 655, pp. 101–115, American Chemical Society, Washington D.C. (1996).
Henrissat, "Analysis of hemicellulose sequences. Relationships to other gycanases" in *Xylans and Xylanases*, eds. Visser et al., Progress in Biotechnology, vol. 7, pp. 97–110, Amsterdam–London–New York–Tokyo (1992).
Puls and Schuseil, "Chemistry of the hemicelluloses: relationship between hemicellulose structure and enzymes required for hydrolysis" in *Hemicellulose and Hemicellulases*, eds. Coughlan & Hazelwood, pp. 1–28, Portland Press Ltd., London–Chapel Hill (1993).
Dominguez, et al., "A common protein fold and similar active site in two distinct families of beta–glycanases,", *Nat. Struc. Biol.* 2:569–576 (1995).
Torronen et al., "Three–dimensional structure of endo–1, 4–β–xylanase II from *Trichoderma reesei*: two conformational states in the active site," *EMBO J* 13(11):2493–2501 (1994).
Krengel and Dijkstra, "Three–dimensional structure of endo–1,4–β–xylanase I from *Aspergillus niger*: Molecular Basis for its Low pH Optimum", *J. Mol. Biol.* 263(1):70–78 (1996).
Ito, et al., "Cloning and Sequencing of the xynC Gene Encoding Acid Xylanase of *Aspergillus kawachii*," *Biosci. Biotechnol. Biochem.* 56–(8):1338–1340 (1992).
de Graaff et al., "Regulation of the sylanase–encoding xInA gene of *Aspergillus tubigensis*", *Mol. Microbiol.* 12(3):479–490 (1994).
Yang et al., "Nucleotide Sequence of a *Bacillus circulans* xylanase gene", *Nucl. Acids. Res.* 16:7187 (1988).
Fukusaki et al., "The complete nucleotide sequence of the xylanase gene (xynA) of *Bacillus pumilus*", *FEBS Lett.* 171:197–201 (1984).
Paice et al., "A xylanase gene from *Bacillus subtilis*: nucleotide sequence and comparison with *B. pumilus* gene", *Arch. Microbiol.* 144:201–202 (1986).
Nakai et al., "Nucleotide sequence and mutational analysis of the gene encoding the novel alkaline xylanase from alkaliphilic *Bacillus sp.* strain 41M–1", *Nucl. Acids Symp. Series* 31:235–236 (1994).
Zappe et al., "Nucleotide sequence of a *Clostridium acetobutylicum* P262 sylanase gene (xynB)", *Nucl. Acids Res.* 18(8):2179 (1990).

(List continued on next page.)

*Primary Examiner*—Manjunath Rao
(74) *Attorney, Agent, or Firm*—Dorsey & Whitney LLP; Robin M. Silva; Renee M. Kosslak

(57) ABSTRACT

The invention relates to novel xylanase activity (XA) proteins and nucleic acids. The invention further relates to the use of the XA proteins in the process of pulp bleaching.

4 Claims, 24 Drawing Sheets

OTHER PUBLICATIONS

Sakka et al., "Nucleotide Sequence of the *Clostridium stercorarium xynA* Gene Encoding Xylanase A: Identification of Catalytic and Cellulose Binding Domains", *Biosci. Biotechnol. Biochem.* 57(2):273–277 (1993).

Apel et al., "Cloning and targeted gene disruption of XYL1, a beta 1,4xylanse gene from the maize pathogen *Cochliobolus carbonum*", Mol. Plant Microbe Interact. 6(4):467–473 (1993).

Paradis et al., "The xynC Gene from *Fibrobacter succinogenes* S85 Codes for a Xylanase with Two Similar Catalytic Domains", *J. Bacteriol.* 175(23):7666–7672 (1993).

Gilbert et al., "Homologous catalytic domains in a rumen fungal xylanase evidence for gene duplication and prokaryotic origin", *Mol. Microbiol.* 6(15):2065–2072 (1992).

Eswaramoorthy, et al, "Crystallization and Preliminary X–ray Crystallographic Studies of Thermostable Xylanase Crystals Isolated from *Paecilomyces varioti*", *J. Mol. Biol.* 243(4):806–808 (1994).

Zhang and Flint, "A bifunctional xylanase encoded by the xynA Gene of the rumen cellulolytic bacterium *Ruminococcus flavefaciens* 17 comprises two dissimilar domains linked by an asparagine/glutamine–rich sequence", *Mol. Microbiol.* 6(8):1013–1023 (1992).

Yaguchi et al., "Amino Acid Sequence of the Low–Molecular–Weight Xylanase from *Trichoderma viride*", in *Xylans and Xylanases*, eds. Visser et al., Progress in Biotechnology vol. 7; pp 149–154, Amsterdam–London–New York–Tokyo (1992).

Shareck et al., "Sequence of three genes specifying xylanases in *Streptomyces lividans*", Gene 107(1):75–82 (1991).

Gruber et al., "Thermophilic Xylanase from *Thermomyces lanuginosus*: High–Resolution X–ray Structure and Modeling Studies", *Biochemistry* 37(39):13475–13485 (1998).

Campbell et al., "A comparison of the Structure of the 20 kd Xylanases from *Trichoderma harzianum* and *Bacillus circulans*", in *Proceedings of the second TRICEL symposium on Trichderma reesei cellulases and other hydrolases* (Suominen and Geinikainen, eds.), Espoo, Finland, Helsinki: Foundation for Biotechnological and Industrial Fermentation Research, pp 63–77 (1993).

Torronen and Rouvinen, "Structural Comparison of Two Major endo–1,4–Xylanases from *Trichoderma reesi*", *Biochemistry* 34:847 (1995).

Viikari et al., "Enzyme–Aided Bleaching of Kraft Pulps: Fundamental Mechanisms and Practical Applications," *Enzymes for Pulp and Paper Processing*, eds. Jeffries and Viikari, ACS Symposium Series, vol. 655, pp. 15–24, American Chemical Society, Washington D.C. (1996).

Paice and Jurasek, "Removing Hemicellulose From Pulps by Specific Enzymic Hydrolysis", *J. Wood Chem. Tech.* 4(2):187–198 (1984).

Luthi et al., "Xylanase from the Extremely Thermophilic Bacterium "*Caldocellum sacharolyticum*": Overexpression of the Gene in *Escherichia coli* and Characterization of the Gene Product" *Appl. Environ. Microbiol.* 56:2577–2683 (1990).

Winterhalter and Liebl, "Two Extremely Thermostable Xylanases of the Hyperthermophilic Bacterium *Thermotoga maritima* MSB8", *Appl. Environ. Microbiol.* 61:1810–1815 (1995).

Simpson et al., "An extremely thermostable xylanase fromt he thermophilic eubacterium Thermotoga", *Biochem. J.* 277:413–417 (1991).

Zeikus et al., "Thermostable Saccaradises", *ACS Symp. Ser.* 460:36–51 (1991).

Biely, "Biotechnological Potential and Production of Xylanolytic Systems Free of Cellulases", *ACS Symp. Ser.* 460:408–416 (1991).

Woodward, "Xylanases: Functions, Properties and Applications", *Top. Enzyme Ferment. Biotechnol.* 8:9–30 (1984).

McCleary, "Enzymatic modification of plant polysaccharides", *Int. J. Biol. Macromol.* 8:349–354 (1986).

Maat et al., "Xylanases and their application in bakery", *In Xylans and xylanases* (eds. Visser et al.), Elsevier Sci pub., Amsterdam. ISBN 0–444–894–772 (1992).

Krishnarau et al., "Enzyme Increase Loaf Volume of Bread Supplemented with Starch Tailings and Insoluble Pentosans", *J. Food Sci.* 59:1251–1254 (1994).

McCarter and Withers, "Mechanisms of enymatic glycoside hydrolysis", *Curr. Opin. Struc. Biol.* 4:885–892 (1994).

Arase et al., "Stabilization of xylanase by random mutagenesis", *FEB Lett.* 316(2):123–7 (1993).

Wakarchuk et al., "Mutational and crystallographic analyses of the active site residues of the *Ibacillus circulans xylanase*", *Protein Sci.* 3(3):467–75 (1994).

Wakarchuk, et al., "Thermostabilizaiton of the *Bacillus circulans* xylanase by the introduction of disulfide bonds," *Protein Eng.* 7(11):1379–86 (1994).

Hellinga et al., "Construction of New Ligand Binding Sites in Proteins of Known Structure; I. Computer–aided Modeling of Sites with Pre–defined Geometry", *J. Mol. Biol*, 222:763–785 (1991).

Hurley et al., "Design and Structural Analysis of Alternative Hydrophobic Core Packing Arrangements in Bacteriophage T4 Lysozyme", *J. Mol. Biol.* 224:1143–1154 (1992).

Desjarlais and Handel, "De novo design of the hydrophobic cores of proteins", *Protein Science* 4:2006–2018 (1995).

Harbury et al., "Repacing protein cores with backbone freedom: Structure prediction for coiled coils", *Proc. Natl. Acad. Sci.* USA 92:8408–8412 (1995).

Klemba et al., "Novel metal–binding proteins by design", *Struc. Biol.* 2(5):368–373 (1995).

Nautiyal, et al., "A Designed Heterotrimeric Coiled Coil", *Biochemistry* 34:11645–11651 (1995).

Betz and Grado, "Controlling Topology and Native–like Behavior fo de Novo–Designed Peptides: Design and Characerization of Antiparallel Four–Stranded Coiled Coils", *Biochemistry* 35:6955–6962 (1996).

Dahiyat and Mayo, "Protein Design automation", *Protein Science* 5:895–903 (1996).

Dahiyat and Mayo, "De Novo Protein Design: Fully Automated Sequence Selection", *Science* 278:82–87 (1997).

Dahayat et al., "De Novo Protein Design: Towards Fully Automated Sequence Selection", *J. Mol. Biol.* 273:789–796 (1997).

Dahiyat et al., "Automated design of the surface positions of protein helices", *Protein Science* 6:1333–1337 (1997).

Jones, "De novo protein design using pairwise potentials and a genetic algorith", *Protein Science* 3:567–574 (1994).

Kono and Doi, "Energy Minimization Method Using Automata Network for Sequence and Side–Chain Conformation Prediction From Given Backbone Geometry", *Proteins: Structure, Function and Genetics* 19:244–255 (1994).

Torronen et al., "Structural and functional properties of low molecular weight endo–1,4–β–xylanases," *J Biotechnology* 57:137–149 (1997).

\* cited by examiner

```
  1 MFKFKKNFLV GLSAALMSIS LFSATASAAS TDYWQNWTDG GGIVNAVNGS
 51 GGNYSVNWSN TGNFVVGKGW TTGSPFRTIN YNAGVWAPNG NGYLTLYGWT
101 RSPLIEYYVV DSWGTYRPTG TYKGTVKSDG GTYDIYTTTR YNAPSIDGDR
151 TTFTQYWSVR QSKRPTGSNA TITFTNHVNA WKSHGMNLGS NWAYQVMATE
201 GYQSSGSSNV TVW
```

FIG._1A

```
  1 ASTDYWQNWT DGGGIVNAVN GSGGNYSVNW SNTGNFVVGK GWTTGSPFRT
       EEEEEE   S SEEEEEE   STTEEEEEE  ES SEEEEE  EESS   TT E

51 INYNAGVWAP NGNGYLTLYG WTRSPLIEYY VVDSWGTYRP TGTYKGTVKS
     EEEEESEEEE ESSEEEEEEE EEETTEEEE  EE EESS       EE EEEEE

101 DGGTYDIYTT TRYNAPSIDG DRTTFTQYWS VRQSKRPTGS NATITFTNHV
     TTEEEEEEEE EESSEE TTS SEE EEEEEE EESS    SSS EEEEHHHHH

151 NAWKSHGMNL GSNWAYQVMA TEGYQSSGSS NVTVW
     HHHHHTT       SEE   EEEE EEEES EEEE EEEE
```

FIG._1B

```
    1 gaattcggtg atgatggatt cgatgcgctt tagttctgag gtgatcacgt tgaagtaaag
   61 ggcgtagtct ccctcgacac tccctttcag aagctgaatg aagcctttaa gagcagtcat
  121 cggatttctg atttcatgag caataccggc tgcgagttcg ccgacaacat gaagggtatc
  181 tgatttcgca ggcgctcctc caattctttt cgctctgtta cgtctttaaa gatagccaag
  241 ttcatatttt gaataatatt ccgtttaaat gagaattcgt ggtattatac tgaaggggac
  301 gatcaaaagc tttggcgtta gtaattaaaa atgttttaaa tgtatacgag tgctgcctca
  361 aagttggaaa aaatattata ggaggtaaca tatgtttaag tttaaaaaga atttcttagt
  421 tggattatcg gcagctttaa tgagtattag cttgttttcg caaccgcct ctgcagctag
  481 cacagactac tggcaaaatt ggactgatgg gggcggtata gtaaacgctg tcaatgggtc
  541 tggcgggaat acagtgtta attggtctaa taccggaaat tttgttgttg gtaaaggttg
  601 gactacaggt tcgccattta ggacgataaa ctataatgcc ggagtttggg cgccgaatgg
  661 caatggatat ttaactttat atggttggac gagatcacct ctcatagaat attatgtagt
  721 ggattcatgg ggtacttata gacctactgg aacgtataaa ggtactgtaa aaagtgatgg
  781 gggtacatat gacatatata caactacacg ttataacgca ccttccattg atggcgatcg
  841 cactactttt acgcagtact ggagtgttcg ccagtcgaag agaccaactg gaagcaacgc
  901 tacaatcact ttcacgaatc atgtgaacgc atggaagagc atggaatga atctgggcag
  961 taattgggct taccaagtca tggcgacaga aggatatcaa agtagtggaa gttctaacgt
 1021 aacagtgtgg taacagatca tccttaatca ggggtagcta acgggctgct gatcgttcct
 1081 tgagaagttt tataatcaat gattattaaa atcgttagta agggttaaag gttgttttct
 1141 actaggtgaa cggccttgca attgctggag gtagggtatt ctccatctgg ttttataact
 1201 tttcctatag gttaatagaa tggtatttaa atgagaatgc tacaatttt tctagtcagc
 1261 gcttgctcac aacagacacc tttacataac tcttctttat caaacataag ccttattcaa
 1321 aataaaaata tctagtagtt gacctgcag
```

FIG._1C

FIG._2A

FIG._2B
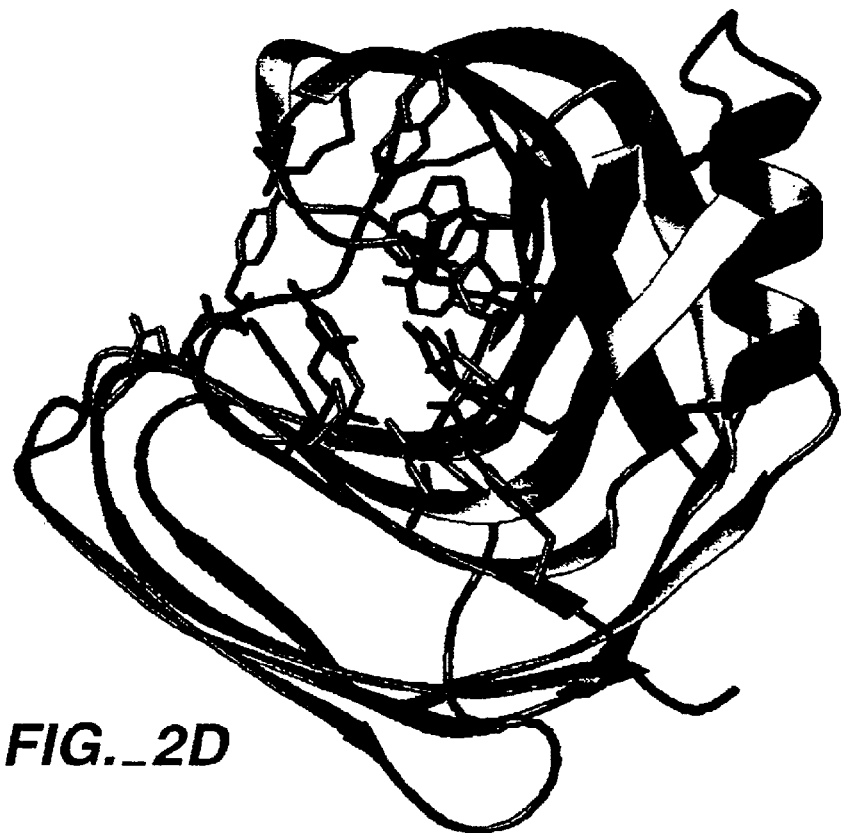
FIG._2D

FIG._2C

Bacillus circulans xylanase CORE

| 26 | 28 | 30 | 36 | 38 | 51 | 53 | 55 | 58 | 62 | 64 | 66 | 68 | 70 | 72 | 77 | 79 | 81 | 105 | 107 |
|---|---|---|---|---|---|---|---|---|---|---|---|---|---|---|---|---|---|---|---|
| Tyr | Val | Trp | Phe | Val | Ile | Tyr | Ala | Trp | Gly | Gly | Leu | Leu | Gly | Thr | Ile | Tyr | Val | Tyr | Ile |

| 130 | 142 | 144 | 146 | 153 | 169 | 171 | 173 | 176 | 178 | 180 | 182 | 184 |
|---|---|---|---|---|---|---|---|---|---|---|---|---|
| Ser | Ala | Ile | Phe | Trp | Met | Thr | Gly | Ser | Gly | Ser | Val | Val |

Bacillus circulans xylanase Region around D83 (a, b, e, f)

| 53 | 66 | 67 | 68 | 81 | 82 | 83 | 84 | 85 | 101 | 105 | 132 | 136 | 138 | 142 | 144 | 149 | 169 |
|---|---|---|---|---|---|---|---|---|---|---|---|---|---|---|---|---|---|
| Tyr | Leu | Thr | Leu | Val | Val | Asp | Ser | Trp | Asp | Tyr | Arg | Arg | Thr | Arg | Ala | Ile | His | Met |

Bacillus circulans xylanase Region around D83 (c, d)

| 53 | 66 | 68 | 81 | 83 | 84 | 101 | 105 | 132 | 136 | 138 | 142 | 144 | 149 | 169 |
|---|---|---|---|---|---|---|---|---|---|---|---|---|---|---|
| Tyr | Leu | Leu | Val | Asp | Ser | Asp | Tyr | Arg | Arg | Thr | Ala | Ile | His | Met |

Bacillus circulans xylanase Helix Region (a, b)

| 70 | 72 | 77 | 79 | 81 | 95 | 96 | 98 | 100 | 101 | 102 | 103 | 105 | 107 | 109 | 128 | 130 | 132 | 144 | 146 |
|---|---|---|---|---|---|---|---|---|---|---|---|---|---|---|---|---|---|---|---|
| Gly | Thr | Ile | Tyr | Val | Lys | Gly | Val | Ser | Asp | Gly | Tyr | Ile | Thr | Tyr | Tyr | Ser | Arg | Ile | Phe |

| 147 | 148 | 149 | 150 | 152 | 153 | 156 | 157 | 158 | 160 | 161 | 164 | 167 |
|---|---|---|---|---|---|---|---|---|---|---|---|---|
| Thr | Asn | His | Val | Ala | Trp | His | Gly | Met | Leu | Gly | Trp | Gln |

Bacillus circulans xylanase Helix Region (c)

| 70 | 72 | 77 | 79 | 81 | 95 | 96 | 98 | 100 | 101 | 105 | 107 | 109 | 128 | 130 | 132 | 144 | 146 |
|---|---|---|---|---|---|---|---|---|---|---|---|---|---|---|---|---|---|
| Gly | Thr | Ile | Tyr | Val | Lys | Gly | Val | Ser | Asp | Tyr | Ile | Thr | Tyr | Ser | Arg | Ile | Phe |

| 147 | 148 | 149 | 150 | 152 | 153 | 156 | 157 | 158 | 160 | 161 | 164 | 167 |
|---|---|---|---|---|---|---|---|---|---|---|---|---|
| Thr | Asn | His | Val | Ala | Trp | His | Gly | Met | Leu | Gly | Trp | Gln |

Bacillus circulans xylanase Active Site Region (a, b)

| 5 | 7 | 11 | 37 | 39 | 63 | 65 | 67 | 71 | 80 | 82 | 88 | 110 | 115 | 118 | 125 | 129 | 168 | 170 |
|---|---|---|---|---|---|---|---|---|---|---|---|---|---|---|---|---|---|---|
| Tyr | Gln | Asp | Val | Gly | Asp | Tyr | Thr | Trp | Tyr | Val | Tyr | Thr | Ala | Ile | Phe | Trp | Val | Ala |

FIG._3

|      | 26 | 28  | 30 | 36 | 38 | 51 | 53  | 55 | 58 | 62 | 64 |
|------|----|-----|----|----|----|----|-----|----|----|----|----|
| >90% | F  |     |    | F  |    |    | F   | A  | F  | G  | V  |
| >50% |    |     | F  |    | V  | I  |     |    |    |    |    |
| >30% |    | I,A |    |    | I  |    |     |    |    |    |    |
| >10% |    | V   | W  |    |    | L  |     |    |    |    |    |
| >1%  |    | S   |    | L  |    | V  | Y,W | S  | A  |    | A  |
| <1%  | Y  | L,W | Y  | Y  |    |    |     |    | S  |    |    |

|      | 66 | 68 | 70 | 72 | 77  | 79 | 81 | 105 | 107 | 130 | 142 |
|------|----|----|----|----|-----|----|----|-----|-----|-----|-----|
| >90% | L  | L  | G  | T  |     |    | V  |     | I   | S   |     |
| >50% |    |    |    |    | I   | F  |    | F   |     |     | L   |
| >30% |    |    |    |    |     |    |    |     |     |     | A   |
| >10% |    |    |    |    |     | W  |    | Y   |     |     |     |
| >1%  |    | V  |    |    | V,L | Y  | I  |     | V   | A   | S   |
| <1%  |    |    |    |    |     |    |    |     | L   |     | V   |

|      | 144 | 146 | 153 | 169 | 171 | 173 | 176 | 178 | 180 | 182 | 184 |
|------|-----|-----|-----|-----|-----|-----|-----|-----|-----|-----|-----|
| >90% |     | F   | W   |     | L   | G   | A   | G   |     |     | V   |
| >50% | I   |     |     | M   |     |     |     |     | A   | I   |     |
| >30% |     |     |     |     |     |     |     |     |     |     |     |
| >10% |     |     |     | L   |     |     |     |     | F   | V   |     |
| >1%  | V,L | I,Y |     |     | I   | A   | S   |     |     |     |     |
| <1%  |     |     | V   | L   | V   |     |     |     | S   | L   |     |

FIG._4A

```
  1 ASTDYWQNWT DGGGIVNAVN GSGGNFSINF SNTGNFVVGK GWTTGSPFRT
 51 INFNAGVFAP NGNVYLTLYG WTRSPLIEFY VVDSWGTYRP TGTYKGTVKS
101 DGGTFDIYTT TRYNAPSIDG DRTTFTQYWS VRQSKRPTGS NLTITFTNHV
151 NAWKSHGMNL GSNWAYQVMA LEGYQASGSA NITVW
```

FIG._4B

|      | 53 | 66 | 67  | 68 | 81 | 82  | 83 | 84    | 85 | 101 | 105 |
|------|----|----|-----|----|----|-----|----|-------|----|-----|-----|
| >90% | F  |    |     | L  | V  | V   | V  |       |    |     | F   |
| >50% |    | L  |     |    |    |     |    | V     | F  | D   |     |
| >30% |    |    | T   |    |    |     |    | A     | Y  |     |     |
| >10% |    | F  | A,D |    |    |     |    |       |    | N   |     |
| >1%  |    |    | S,N | V  | A  | L   | F  | S,T,D |    |     | Y   |
| <1%  |    |    |     | I  |    | T,D |    |       |    | A   |     |

|      | 132 | 136 | 138 | 142 | 144 | 149 | 169 |
|------|-----|-----|-----|-----|-----|-----|-----|
| >90% |     | M   |     |     | L   | F   | M   |
| >50% | M   |     | T   | L   |     |     |     |
| >30% |     |     |     |     |     |     |     |
| >10% | L,A |     | V,D | I   |     |     |     |
| >1%  |     | K   | L   | A,V | A,I | H   | L   |
| <1%  |     | L   | A   |     |     | Y   |     |

FIG._5A

```
  1 ASTDYWQNWT DGGGIVNAVN GSGGNYSVNW SNTGNFVVGK GWTTGSPFRT
 51 INFNAGVWAP NGNGYLTLYG WTRSPLIEYY VVVVFGTYRP TGTYKGTVKS
101 DGGTFDIYTT TRYNAPSIDG DRTTFTQYWS VMQSKMPTGS NLTLTFTNFV
151 NAWKSHGMNL GSNWAYQVMA TEGYQSSGSS NVTVW
```

FIG._5B

|      | 53 | 66 | 67  | 68 | 81 | 82  | 83  | 84    | 85 | 101 | 105 |
|------|----|----|-----|----|----|-----|-----|-------|----|-----|-----|
| >90% | F  |    |     | L  | V  | V   | V   |       |    |     | F   |
| >50% |    | L  |     |    |    |     |     |       | F  | D   |     |
| >30% |    |    | T   |    |    |     |     | A,V   | Y  |     |     |
| >10% |    | F  | A,D |    |    |     |     |       |    | N   |     |
| >1%  |    |    | S,N | V  | A  | L   | T,D | S,T,D |    |     | Y   |
| <1%  |    |    |     |    |    | T,D |     |       |    | A   |     |

|      | 132 | 136 | 138   | 142 | 144 | 149 | 169 |
|------|-----|-----|-------|-----|-----|-----|-----|
| >90% |     | M   |       |     | L   | F   | M   |
| >50% | M   |     | T     | L   |     |     |     |
| >30% |     |     |       |     |     |     |     |
| >10% | A,L |     | D,V   | I   |     |     |     |
| >1%  |     | L   | A,L,S | V,A | I   | H   | L   |
| <1%  | S   | K   | N     |     |     | Y   |     |

FIG._6A

```
  1 ASTDYWQNWT DGGGIVNAVN GSGGNYSVNW SNTGNFVVGK GWTTGSPFRT
 51 INFNAGVWAP NGNGYLTLYG WTRSPLIEYY VVVVFGTYRP TGTYKGTVKS
101 DGGTFDIYTT TRYNAPSIDG DRTTFTQYWS VMQSKMPTGS NLTLTFTNFV
151 NAWKSHGMNL GSNWAYQVMA TEGYQSSGSS NVTVW
```

FIG._6B

|      | 53 | 66 | 68  | 81 | 83 | 84  | 101 | 105 |
|------|----|----|-----|----|----|-----|-----|-----|
| >90% | F  |    | L   | V  | V  |     |     |     |
| >50% |    | L  |     |    |    |     | D   | F   |
| >30% |    |    |     |    |    | V,A |     |     |
| >10% |    | F  |     |    |    |     | N   | Y   |
| >1%  |    |    | V,I | A  | F  | S,T,D | A,S |   |
| <1%  | W  |    |     |    |    | M   |     |     |

|      | 132 | 136 | 138 | 142 | 144 | 149 | 169 |
|------|-----|-----|-----|-----|-----|-----|-----|
| >90% |     | M   |     |     |     |     | M   |
| >50% | M   |     | T   |     | L   | F   |     |
| >30% |     |     |     | L,I |     |     |     |
| >10% | L,A |     | V,D | A   | I   | H   |     |
| >1%  | S   | K,L | L,A | V   | A   | Y   | L   |
| <1%  | D,E | E,F | S,N |     |     |     |     |

FIG._7A

```
  1 ASTDYWQNWT DGGGIVNAVN GSGGNYSVNW SNTGNFVVGK GWTTGSPFRT
 51 INFNAGVWAP NGNGYLTLYG WTRSPLIEYY VVVVWGTYRP TGTYKGTVKS
101 DGGTFDIYTT TRYNAPSIDG DRTTFTQYWS VMQSKMPTGS NLTLTFTNFV
151 NAWKSHGMNL GSNWAYQVMA TEGYQSSGSS NVTVW
```

FIG._7B

|      | 53 | 66 | 68  | 81 | 83  | 84    | 101 | 105 |
|------|----|----|-----|----|-----|-------|-----|-----|
| >90% | F  |    |     | V  |     |       |     |     |
| >50% |    | L  | L   |    | V   |       | D   | F   |
| >30% |    |    |     |    | D   | A,V   |     |     |
| >10% |    | F  |     |    |     |       | N   | Y   |
| >1%  |    |    | V,I | A  | T   | S,T,D | A   |     |
| <1%  | W  |    |     |    | A,E |       | S   |     |

|      | 132 | 136 | 138   | 142 | 144 | 149 | 169 |
|------|-----|-----|-------|-----|-----|-----|-----|
| >90% |     | M   |       |     |     |     | M   |
| >50% | M   |     |       | L   | L   | F   |     |
| >30% |     |     | T     | I   |     |     |     |
| >10% | L,A |     | D,V   |     | I   | H   |     |
| >1%  | S   | K,L | A,L,S,N | V,A | V |     | L   |
| <1%  | D   |     | H     |     |     | Y   |     |

FIG._8A

```
  1 ASTDYWQNWT  DGGGIVNAVN  GSGGNYSVNW  SNTGNFVVGK  GWTTGSPFRT
 51 INFNAGVWAP  NGNGYLTLYG  WTRSPLIEYY  VVVVWGTYRP  TGTYKGTVKS
101 DGGTFDIYTT  TRYNAPSIDG  DRTTFTQYWS  VMQSKMPTGS  NLTLTFTNFV
151 NAWKSHGMNL  GSNWAYQVMA  TEGYQSSGSS  NVTVW
```

FIG._8B

|     | 53 | 66 | 67  | 68 | 81 | 82  | 83 | 84    | 85 | 101 | 105 |
|-----|----|----|-----|----|----|-----|----|-------|----|-----|-----|
| >90%| F  | L  |     | L  | V  | V   | V  |       |    |     |     |
| >50%|    |    |     |    |    |     |    | V     | F  | D   | F   |
| >30%|    |    | T   |    |    |     |    | A     | Y  |     |     |
| >10%|    |    | A,D |    |    |     | F  |       |    | N   |     |
| >1% | W  | F  | S,N | V  | A  | L,T |    | S,T,D |    | A   | Y   |
| <1% |    |    |     | I  |    | D   |    |       |    | S   |     |

|     | 132 | 136     | 138 | 142   | 144 | 149 | 169 |
|-----|-----|---------|-----|-------|-----|-----|-----|
| >90%|     |         |     |       |     | F   | M   |
| >50%| A   | L       | T   | L     | L   |     |     |
| >30%| L   |         |     |       |     |     |     |
| >10%|     | K       | V,D | I     |     |     |     |
| >1% | S   | I,F,E,A | A,L | V,A,F | A,I | H,Y | L   |
| <1% |     |         | S   |       |     |     |     |

FIG._9A

```
  1 ASTDYWQNWT DGGGIVNAVN GSGGNYSVNW SNTGNFVVGK GWTTGSPFRT
 51 INFNAGVWAP NGNGYLTLYG WTRSPLIEYY VVVVFGTYRP TGTYKGTVKS
101 DGGTFDIYTT TRYNAPSIDG DRTTFTQYWS VAQSKLPTGS NLTLTFTNFV
151 NAWKSHGMNL GSNWAYQVMA TEGYQSSGSS NVTVW
```

FIG._9B

|      | 53 | 66 | 67  | 68  | 81  | 82    | 83 | 84    | 85 | 101 | 105 |
|------|----|----|-----|-----|-----|-------|----|-------|----|-----|-----|
| >90% | F  | L  |     | L   | V   | V     | V  |       |    |     | F   |
| >50% |    |    |     |     |     |       |    | V     | F  | D   |     |
| >30% |    |    | T   |     |     |       |    | A     | Y  |     |     |
| >10% |    |    | A,D |     |     |       |    |       |    | N   |     |
| >1%  |    | F  | S,N | V,I | A   | L,T,D | D  | S,T,D |    | A   | Y   |
| <1%  | W  |    |     |     |     |       |    | T     |    | S   |     |

|      | 132 | 136  | 138   | 142 | 144 | 149 | 169 |
|------|-----|------|-------|-----|-----|-----|-----|
| >90% |     |      |       |     | L   | F   | M   |
| >50% | A   | L    |       | L   |     |     |     |
| >30% |     |      | T     |     |     |     |     |
| >10% | L   | I    | D,V   | I   |     |     |     |
| >1%  | S   | K,F,E| A,S,N | V,A | I   | H   | L   |
| <1%  |     | A    | L,Hsp | F   |     | Y   |     |

FIG._10A

```
  1 ASTDYWQNWT DGGGIVNAVN GSGGNYSVNW SNTGNFVVGK GWTTGSPFRT
 51 INFNAGVWAP NGNGYLTLYG WTRSPLIEYY VVVAFGTYRP TGTYKGTVKS
101 DGGTFDIYTT TRYNAPSIDG DRTTFTQYWS VAQSKLPTGS NLTLTFTNFV
151 NAWKSHGMNL GSNWAYQVMA TEGYQSSGSS NVTVW
```

FIG._10B

| | 70 | 72 | 77 | 79 | 81 | 95 | 96 | 98 | 100 | 101 | 102 |
|---|---|---|---|---|---|---|---|---|---|---|---|
| >90% | G | T | I | F | V | | S | | | D | D |
| >50% | | | | | | K | | T | V | | |
| >30% | | | | | | | | | | | |
| >10% | | | | | | L,I | | | V,D,A | A | |
| >1% | | | L,V | | I | E,Q,V | G | | | | |
| <1% | | | | | | R | | E | | | |

| | 103 | 105 | 107 | 109 | 128 | 130 | 132 | 144 | 146 | 147 | 148 |
|---|---|---|---|---|---|---|---|---|---|---|---|
| >90% | I | F | | | | A | A | L | F | | E |
| >50% | | | I | V | | | | | | I | |
| >30% | | | | V | I | | | | | D | |
| >10% | | | L | I,K,E | | | | | | | |
| >1% | | | | T,Q,L | | | | | | | |
| <1% | | | | D,R | L | | | I | | | Q |

| | 149 | 150 | 152 | 153 | 156 | 157 | 158 | 160 | 161 | 164 | 167 |
|---|---|---|---|---|---|---|---|---|---|---|---|
| >90% | F | I | | W | | G | | F | G | W | E |
| >50% | | | S | | | | I | | | | |
| >30% | | | | | Y | | | | | | |
| >10% | | | Y,A | | F,E | | L,M | | | | |
| >1% | | V | | F | V,I,L,Q,N | | V | L | | | |
| <1% | H | | W | | | | E | | | | |

FIG._11A

```
  1 ASTDYWQNWT DGGGIVNAVN GSGGNYSVNW SNTGNFVVGK GWTTGSPFRT
 51 INYNAGVWAP NGNGYLTLYG WTRSPLIEFY VVDSWGTYRP TGTYKSTTKV
101 DDITFDIYIT TRYNAPSIDG DRTTFTQVWA VAQSKRPTGS NATLTFIEFI
151 NSWKSYGINF GSNWAYEVMA TEGYQSSGSS NVTVW
```

FIG._11B

|      | 70 | 72 | 77 | 79 | 81 | 95  | 96 | 98 | 100 | 101 | 102 |
|------|----|----|----|----|----|-----|----|----|-----|-----|-----|
| >90% | G* | T  | I  | F  | V  | K   | G* |    | V   | D   | G*  |
| >50% |    |    |    |    |    |     |    | V  |     |     |     |
| >30% |    |    |    |    |    |     |    |    |     |     |     |
| >10% |    |    |    |    |    |     |    | E  |     |     |     |
| >1%  |    |    | V  |    |    | L,E |    | T  |     |     |     |
| <1%  |    |    |    |    |    | I   |    | L  |     |     |     |

|      | 103 | 105 | 107 | 109   | 128 | 130 | 132 | 144 | 146 | 147           | 148             |
|------|-----|-----|-----|-------|-----|-----|-----|-----|-----|---------------|-----------------|
| >90% | G   | Y*  |     |       |     | S*  | R*  |     | F   |               |                 |
| >50% |     |     | I   |       | V   |     |     | I   |     |               | E               |
| >30% |     |     |     | I,V   |     |     |     |     |     |               |                 |
| >10% |     |     | L   | E     | I   |     |     | V   |     | D,E,I         |                 |
| >1%  |     |     |     | K,T,Q |     |     |     |     |     | V,Q,L,A,K,N,S | Q,K,R,D,A       |
| <1%  |     |     |     | D     |     |     |     |     |     |               | S,L             |

|      | 149 | 150 | 152 | 153 | 156     | 157 | 158 | 160 | 161 | 164 | 167 |
|------|-----|-----|-----|-----|---------|-----|-----|-----|-----|-----|-----|
| >90% | H*  | I   |     | W*  |         | G   |     | F   | G   | W   | E   |
| >50% |     |     | A   |     |         |     | I   |     |     |     |     |
| >30% |     |     | S   |     | Y       |     |     |     |     |     |     |
| >10% |     |     |     |     | L,Q     |     |     |     |     |     |     |
| >1%  |     |     |     |     | F,N,E,K |     | M,L |     |     |     |     |
| <1%  |     | V   | D   |     | I       |     | V   | L   |     |     |     |

FIG._12A

```
  1 ASTDYWQNWT DGGGIVNAVN GSGGNYSVNW SNTGNFVVGK GWTTGSPFRT
 51 INYNAGVWAP NGNGYLTLYG WTRSPLIEFY VVDSWGTYRP TGTYKGTVKV
101 DGGTYDIYIT TRYNAPSIDG DRTTFTQVWS VRQSKRPTGS NATITFIEHI
151 NSWKSYGINF GSNWAYEVMA TEGYQSSGSS NVTVW
```

FIG._12B

|      | 70 | 72 | 77 | 79 | 81 | 95    | 96 | 98  | 100 | 101 |
|------|----|----|----|----|----|-------|-----|-----|-----|-----|
| >90% | G  | T  | I  | F  |    |       |    | S   |     | D   |
| >50% |    |    |    |    | V  | K     |    |     | V   |     |
| >30% |    |    |    |    |    |       |    | T   |     |     |
| >10% |    |    |    |    | I  |       |    | V,D | A   |     |
| >1%  |    |    | L  |    |    | I,L,E,Q | G | A,E |     |     |
| <1%  |    |    | V  |    |    | V     |    |     |     |     |

|      | 105 | 107 | 109  | 128 | 130 | 132 | 144 | 146 | 147 | 148 |
|------|-----|-----|------|-----|-----|-----|-----|-----|-----|-----|
| >90% | F   |     |      |     | A   | M   |     | F   |     | E   |
| >50% |     | I   |      | V   |     |     | L   |     | I   |     |
| >30% |     |     | V,I  |     |     |     |     |     | D   |     |
| >10% |     | L   | E    | I   |     |     | I   |     |     |     |
| >1%  |     |     | K,T,L,Q | L |     |     |     |     | Y   |     |
| <1%  |     | V   | R,D  |     |     |     |     |     |     |     |

|      | 149 | 150 | 152 | 153 | 156 | 157 | 158 | 160 | 161 | 164 | 167 |
|------|-----|-----|-----|-----|-----|-----|-----|-----|-----|-----|-----|
| >90% | F   | V   |     | W   |     | G   |     | L   | G   | W   | E   |
| >50% |     |     | S   |     | Y   |     | I   |     |     |     |     |
| >30% |     |     |     |     |     |     |     |     |     |     |     |
| >10% |     |     | Y,A |     | E,F |     |     |     |     |     |     |
| >1%  |     | H   | I   |     | F   | I,V,L,Q |   | L |     |     |     |
| <1%  |     |     | W   |     | N   |     | M,V |    |     |     |     |

FIG. 13A

```
  1 ASTDYWQNWT DGGGIVNAVN GSGGNYSVNW SNTGNFVVGK GWTTGSPFRT
 51 INYNAGVWAP NGNGYLTLYG WTRSPLIEFY VVDSWGTYRP TGTYKSTTKV
101 DGGTFDIYIT TRYNAPSIDG DRTTFTQVWA VMQSKRPTGS NATLTFIEFV
151 NSWKSYGINL GSNWAYEVMA TEGYQSSGSS NVTVW
```

FIG. 13B

| WT | PDA PROBABILITY DISTRIBUTION | | | | | |
|---|---|---|---|---|---|---|
| 5 Y | W 37.2% | F 25.8% | Y 22.9% | H 14.0% | | |
| 7 Q | E 69.1% | L 30.2% | | | | |
| 11 D | I 41.2% | D 10.7% | V 10.1% | M 7.9% | L 6.4% | E 5.3% | T 4.2% |
| | Q 3.8% | Y 2.6% | F 2.1% | N 1.9% | S 1.9% | A 1.1% |
| 37 V | D 29.9% | M 29.4% | V 21.4% | S 12.8% | I 4.1% | E 1.0% |
| 39 G | A 99.8% | | | | | |
| 63 N | W 91.2% | Q 6.7% | A 1.4% | | | |
| 65 Y | E 91.7% | L 4.9% | M 3.4% | | | |
| 67 T | E 81.0% | D 12.3% | L 3.9% | A 1.7% | | |
| 71 W | V 37.8% | F 35.5% | W 8.5% | M 6.0% | D 5.8% | E 4.3% | I 1.0% |
| 80 Y | M 32.4% | L 31.5% | F 19.0% | I 5.9% | Y 5.7% | E 3.7% |
| 82 V | V 88.6% | D 11.0% | | | | |
| 88 Y | N 91.1% | K 6.6% | W 1.3% | | | |
| 110 T | D 99.9% | | | | | |
| 115 A | A 35.6% | Y 27.8% | T 14.4% | D 10.2% | S 9.2% | F 2.6% |
| 118 I | E 92.2% | D 2.6% | I 2.0% | A 1.7% | | |
| 125 F | F 79.4% | Y 11.8% | M 7.3% | L 1.5% | | |
| 129 W | E 91.3% | S 8.6% | | | | |
| 168 V | D 98.1% | | | | | |
| 170 A | A 78.7% | S 17.6% | D 3.7% | | | |

FIG._14A

```
  1 ASTDWWENWT IGGGIVNAVN GSGGNYSVNW SNTGNFDVAK GWTTGSPFRT
 51 INYNAGVWAP NGWGELELYG WTRSPLIEYL VVDSWGTNRP TGTYKGTVKS
101 DGGTYDIYTD TRYNYPSEDG DRTTMTQYSS VRQSKRPTGS NATITFTNHV
151 NAWKSHGMNL GSNWAYQDMA TEGYQSSGSS NVTVW
```

FIG._14B

| WT | PDA PROBABILITY DISTRIBUTION | | | | | |
|---|---|---|---|---|---|---|
| 5 Y | Y 69.2% | W 17.0% | H 7.3% | F 6.0% | | |
| 7 Q | Q 78.1% | E 18.0% | L 3.9% | | | |
| 11 D | D 97.1% | | | | | |
| 37 V | V 50.9% | D 33.9% | S 5.4% | A 1.2% | L 1.0% | |
| 39 G | S 80.6% | A 19.4% | | | | |
| 63 N | W 92.2% | D 3.9% | Q 2.9% | | | |
| 65 Y | E 91.1% | L 8.7% | | | | |
| 67 T | E 92.8% | L 5.2% | | | | |
| 71 W | W 62.6% | E 13.3% | M 11.0% | S 6.9% | D 4.0% | |
| 80 Y | M 66.4% | F 13.6% | E 10.7% | I 6.0% | L 1.3% | |
| 82 V | V 86.0% | D 12.8% | | | | |
| 88 Y | W 55.1% | Y 15.9% | N 11.4% | F 9.5% | K 1.9% | Q 1.4% | D 1.4% |
| | | | | | | M 1.4% |
| 110 T | D 99.9% | | | | | |
| 115 A | D 47.1% | S 27.8% | T 17.1% | A 7.9% | | |
| 118 I | I 47.6% | D 43.0% | E 3.6% | V 2.5% | A 1.4% | |
| 125 F | Y 51.1% | F 43.3% | L 3.4% | M 2.0% | | |
| 129 W | L 63.2% | M 28.1% | E 7.5% | | | |
| 168 V | D 98.2% | | | | | |
| 170 A | T 92.3% | A 5.9% | | | | |

FIG._15A

```
  1 ASTDYWQNWT DGGGIVNAVN GSGGNYSVNW SNTGNFDVSK GWTTGSPFRT
 51 INYNAGVWAP NGWGELELYG WTRSPLIEYM VVDSWGTWRP TGTYKGTVKS
101 DGGTYDIYTD TRYNDPSIDG DRTTFTQYLS VRQSKRPTGS NATITFTNHV
151 NAWKSHGMNL GSNWAYQDMT TEGYQSSGSS NVTVW
```

FIG._15B

```
MFKFKKNFLV  GLSAALMSIS  LFSATASAAS  TDYWQNWTDG  GGIVNAVNGS  GGNYSVNWSN
TGNFVVGKGW  TTGSPFRTIN  YNAGVWAPNG  NGYLTLYGWT  RSPLIEYYVV  DSWGTYRPTG
TYKGTVKSDG  GTYDIYTTTR  YNAPSIDGDR  TTFTQYWSVR  QSKRPTGSNA  TITFTNHVNA
WKSHGMNLGS  NWAYQVMATE  GYQSSGSSNV  TVW
```

FIG._16A

```
mnlrklrllf  vmcigltlil  tavpaharti  tnnemgnhsg  ydyelwkdyg  ntsmtlnngg
afsagwnnig  nalfrkgkkf  dstrthhqlg  nisinynasf  npggnsylcv  ygwtqsplae
yyivdswgty  rptgaykgsf  yadggtydiy  ettrvnqpsi  igiatfkqyw  svrqtkrtsg
tvsvsahfrk  weslgmpmgk  myetaftveg  yqssgsanvm  tnqlfign
```

FIG._16B

```
mnllvqprrr  rrgpvtllvr  sawavalaal  aalmlpgtaq  adtvvttnqe  gtnngyyysf
wtdsqgtvsm  nmgsgggqyst swrntgnfva  gkgwanggrr  tvqysgsfnp  sgnaylalyg
wtsnplveyy  ivdnwgtyrp  tgeykgtvts  dggtydiykt  trvnkpsveg  trtfdqywsv
rqskrtggti  ttgnhfdawa  ragmplgnfs  yymimategy  qssgtssinv  ggtgggdsgg
gdnggggggc  tatvsagqkw  gdrynldvsv  sgasdwtvtm  nvpspakvls  nwnvnasyps
aqtltarlng  sgnnwgatiq  ananwtwpsv  scsag
```

FIG._16C

```
mqqdgtqqdr  ikqspaplng  msrrgflgga  gtlalatasg  lllpgtahaa  ttittnqtgt
dgmyysfwtd  gggsvsmtln  gggsystqwt  ncgnfvagkg  wstgdgnvry  ngyfnpvgng
ygclygwtsn  plveyyivdn  wgsyrptgty  kgtvssdggt  ydiyqttryn  apsvegtktf
qqywsvrqsk  vtsgsgtitt  gnhfdawara  gmnmgqfryy  mimategyqs  sgssnitvsg
```

FIG._16D

```
MLRRKVIFTV  LATLVMTSLT  IVDNTAFAAT  NLNTTESTFS  KEVLSTQKTY  SAFNTQAAPK
TITSNEIGVN  GGYDYELWKD  YGNTSMTLKN  GGAFSCQWSN  IGNALFRKGK  KFNDTQTYKQ
LGNISVNYDC  NYQPYGNSYL  CVYGWTSSPL  VEYYIVDSWG  SWRPPGGTSK  GTITVDGGIY
DIYETTRINQ  PSIQGNTTFK  QYWSVRRTKR  TSGTISVSKH  FAAWESKGMP  LGKMHETAFN
IEGYQSSGKA  DVNSMSINIG  K
```

FIG._16E

```
sgtpsstgtd  ggyyyswwtd  gagdatyqnn  gggsytltws  gnngnlvggk  gwnpgaasrs
isysgtyqpn  gnsylsvygw  trsslieyyi  vesygsydps  saashkgsvt  cngatydils
twrynapsid  gtqtfeqfws  vrnpkkapgg  sisgtvdvqc  hfdawkglgm  nlgsehnyqi
vategyqssg  tatitvt
```

FIG._16F

```
qtigpgtgfn  ngyfysywnd  ghggvtytng  pggqfsvnws  nsgnfvggkg  wqpgtknkvi
nfsgtynpng  nsylsvygws  rnplieyyiv  enfgtynpst  gatklgevts  dgsvydiyrt
qrvnqpsiig  tstfyqywsv  rrthrssgsv  ntanhfnawa  qqgltlgtmd  yqivavegyf
ssgsasitvs
```

FIG._16G

```
qtigpgtgys  ngyyysywnd  ghagvtytng  gggsftvnws  nsgnfvagkg  wqpgtknkvi
nfsgsynpng  nsylsiygws  rnplieyyiv  enfgtynpst  gatklgevts  dgsvydiyrt
qrvnqpsiig  tatfyqywsv  rrnhrssgsv  ntanhfnawa  shgltlgtmd  yqivavegyf
ssgsasitvs
```

FIG._16H

```
asinydqnyq  tggqvsysps  ntgfsvnwmt  qddfvvgvgw  ttgssapinf  ggsfsvnsgt
gllsvygwst  nplveyyime  dnhnypaqgt  vkgtvtsdga  tytiwentrv  nepsiqgtat
fnqyisvrns  prtsgtvtvq  nhfnawaslg  lhlgqmnyqv  vavegwggsg  sasqsvsn
```

FIG._16I

```
xtiqpgtgyn  ngyfysywnd  ghggvtytng  pggqfsvnws  nsgnfvggkg  wqpgtknkvi
nfsgsynpng  nsylsvygws  rnplieyyiv  enfgtynpst  gatklgevts  dgsvydiyrt
qrvnqpsiig  tatfyqywsv  rrnhrssgsv  ntanhfnawa  qqgltlgtmd  yqivavegyf
ssgsasitvs
```

FIG._16J

```
gttpnsegwh  dgyyyswwsd  gggdstytnn  sggtyeitwg  nggnlvggkg  wnpglnarai
hftgvyqpng  tsylsvygwt  rnplveyyiv  enfgssnpss  gstdlgtvsc  dgstytlgqs
trynapsidg  tqtfnqywsv  rqdkrssgtv  qtgchfdawa  saglnvtgdh  yyqivategy
fssgyaritv  advg
```

FIG._16K

```
xttpnsegwh  dgyyyswwsd  ggaqatytnl  eggtyeiswg  dggnlvggkg  wnpglnarai
hfegvyqpng  nsylavygwt  rnplveyyiv  enfgtydpss  gatdlgtvec  dgsiyrlgkt
trvnapsidg  tqtfdqywsv  rqdkrtsgtv  qtgchfdawa  raglnvngdh  yyqivategy
fssgyaritv  advg
```

FIG._16L

```
saginyvqny  ngnlgdftyd  esagtfsmyw  edgvssdfvv  glgwttgssn  aitysaeysa
sgsasylavy  gwvnypqaey  yivedygdyn  pcssatslgt  vysdgstyqv  ctdtrtneps
itgtstftqy  fsvrestrts  gtvtvanhfn  fwahhgfgns  dfnyqvvave  awsgagsasv
tiss
```

FIG._16M

```
MLTKNLLLCF AAAKAVLAVP HDSVVERSDA LHKLSERSTP SSTGENNGYY YSFWTDGGGD
VTYTNGNAGS YSVEWSNVGN FVGGKGWNPG SAKDITYSGN FTPSGNGYLS VYGWTTDPLI
EYYIVESYGD YNPGSGGTTR GNVSSDGSVY DIYTATRTNA PSIQGTATFS QYWSVRQNKR
VGGTVTTSNH FNAWAKLGMN LGTHNYQILA TEGYQSSGSS SITIQ
```

FIG._16N

```
mkvtaasagl  lghafaapvp  qpvlvsrsag  inyvqnyngn  ladftydesa  gtfsmywedg
vssdfvvglg  wttgssnais  ysaeysasgs  ssylavygwv  nypqaeyyiv  edygdynpcs
satslgtvys  dgstyqvctd  trtnepsitg  tstftqyfsv  restrtsgtv  tvanhfnfwa
qhgfgnsdfn  yqvmaveaws  gagsasvtis  s
```

FIG._16O

```
mrtikfffav  aiatvakaqw  ggggasagqr  ltvgngqtqh  kgvadgysye  iwldntggsg
smtlgsgatf  kaewnasvnr  gnflarrgld  fgsqkkatdy  syigldytat  yrqtgsasgn
srlcvygwfq  nrgvqgvplv  eyyiiedwvd  wvpdaqgrmv  tidgaqykif  qmdhtgptin
ggsetfkqyf  svrqqkrtsg  hitvsdhfke  wakqgwgign  lyevalnaeg  wqssgiadvt
kldvyttqkg  snpaptstgt  vpsssaggst  angkkftvgn  gqnqhkgvnd  gfsyeiwldn
tggngsmtlg  sgatfkaewn  aavnrgnfla  rrgldfgsqk  katdydyigl  dyaatykqta
sasgnsrlcv  ygwfqnrgln  gvplveyyii  edwvdwvpda  qgkmvtidga  qykifqmdht
gptinggset  fkqyfsvrqq  krtsghitvs  dhfkewakqg  wignlyeva   lnaegwqssg
vadvtlldvy  ttpkgsspat  saaprtttrt  ttrtkslptn  ynkcsarita  qgykccsdpn
cvvyytdedg  twgvenndwc  gcgveqcssk  itsqgykccs  dpncvvfytd  ddgkwgvenn
dwcgcgf
```

FIG._16P

```
mvsftsiita  avaatgalaa  patdvslvar  qntpngegth  ngcfwswwsd  ggaratytng
aggsysvswg  sggnlvggkg  wnpgtartit  ysgtynyngn  sylavygwtr  nplveyyvve
nfgtydpssq  sqnkgtvtsd  gssykiaqst  rtnqpsidgt  rtfqqywsvr  qnkrssgsvn
mkthfdawas  kgmnlgqhyy  qivategyfs  tgnaqitvnc  p
```

FIG._16Q

```
mkrkvkkmaa  matsiimaim  iilhsipvla  griiydnetg  thggydyelw  kdygntimel
ndggtfscqw  snignalfrk  grkfnsdkty  qelgdivvey  gcdynpngns  ylcvygwtrn
plveyyives  wgswrppgat  pkgtitqwma  gtyeiyettr  vnqpsidgta  tfqqywsvrt
skrtsgtisv  tehfkqwerm  gmrmgkmyev  altvegyqss  gyanvyknei  riganptpap
sqspirrdaf  siieaeeyns  tnsstlqvig  tpnngrgigy  iengntvtys  nidfgsgatg
fsatvatevn  tsiqirsdsp  tgtllgtlyv  sstgswntyq  tvstniskit  gvhdivlvfs
gpvnvdnfif  srsspvpapg  dntrdaysii  qaedydssyg  pnlqifslpg  ggsaigyien
gysttyknid  fgdgatsvta  rvatqnatti  qvrlgspsgt  llgtiyvgst  gsfdtyrdvs
atisntagvk  divlvfsgpv  nvdwfvfsks  gt
```

FIG._16R mklskikkvl sgtvsalmia saapvvasaa dqqtrgnvgg ydyemwnqng qgqasmnpga
gsftcswsni enflarmgkn ydsqkknyka fgnivltydv eytprgnsym cvygwtrnpl
meyyivegwg dwrppgndge vkgtvsangn tydirktmry nqpsldgtat fpqywsvrqt
sgsannqtny mkgtidvtkh fdawsaagld msgtlyevsl niegyrsngs anvksvsvtq
ggssdnggqq qnndwnqqnn nqqqnndwnn wgqqnndwnq wnnqgqqnnd wnnwgqqnnd
wnqwnnqgqq qnndwnnwgq qnndwnqwnn qgqqqnndwn nwgqqnndwn qwnnqgqqqn
ndwnnwgqqn ndwnqwnnqn nnqqnawngw dnnnnwnqnn qqqnnwdwnn qnnwnnnqqq
nndwnqwnnq nnwnnnqqqn ndwnqwnnqg qqnndwnqwn nqnnwnqnnn qqnawngwdn
nnnwnqwdqn nqwnnqqqnn twdwnnqnnw nnnqqnndwn qwnnqgqqqn ndwnqwnnqn
nnqnngwdwn nqnnwnqnnn qqnawngwdn nnnwnqwggq nndwnnqqqn ndwnqwnnqg
qqqnndwnnq nnwnqgqqnn nnsagssdsl kgafskyfki gtsvspheln sgadflkkhy
nsitpenelk pesildqgac qqkgnnvntq islsraaqtl kfceqngial rghtfvwysq
tpdwffrenf sqngayvskd imnqrlesmi kntfaalksq ypnldvysyd vcnelflnng
ggmrgadnsn wvkiygddsf vinafkyarq yapagcklyl ndyneyipak tndiynmamk
lkqlgyidgi gmqshlatny pdantyetal kkflstglev qiteldictc nsaeqadlye
kifklamqns aqipavtiwg tqdtvswrss qnpllfsagy qpkpaydrvm alak

FIG._16S mktfsvtkss vvfamalgma stafaqdfcs naqhsgqkvt itsnqtgkig digyelwden
ghggsatfys dgsmdcnitg akdylcragl slgsnktyke lggdmiaefk lvksgaqnvg
ysyigiygwm egvsgtpsql veyyvidntl andmpgswig nerkgtitvd ggtyivyrnt
rtgpaiknsg nvtfyqyfsv rtsprdcgti nisehmrqwe kmgltmgkly eakvlgeagn
vngevrgghm dfphakvyvk ngsdpvssss vksssstdap ksssskgngn vsgkidackd
vmghegketr tqgqnnssvt gnvgsspyhy eiwyqggnns mtfydngtyk aswngtndfl
arvgfkydek htyeelgpid ayykwskqgs aggynyigiy gwtvdplvey yivddwfnkp
ganllgqrkg eftvdgdtye iwqntrvqqp sikgtqtfpq yfsvrksars cghiditahm
kkweelgmkm gkmyeakvlv eagggsgsfd vtyfkmtdka hplaqpepes ssseakvess
sstvalhaap kmelksgnfq vfdmqgrflg tvkldagasv aqvlkanfkn agiymvkqgn
fmqrvavk

FIG._16T mkvtaafagl lvtafaapap epdlvsrsag inyvqnyngn lgdftydesa gtfsmywedg
vssdfvvglg wttgssnait ysaeysasgs asylavygwv nypqaeyyiv edygdynpcs
satslgtvys dgstyqvctd trtnepsitg tstftqyfsv restrtsgtv tvanhfnfwa
hhgfgnsdfn yqvvaveaws gagsasvtis s

FIG._16U mkqvkimflm tmflgigllf fsenaeaait sneigthdgy dyefwkdsgg sgsmtlnsgg
tfsaqwsnvn nilfrkgkkf detqthqqig nmsinygaty npngnsyltv ygwtvdplve
fyivdswgtw rppggtpkgt invdggtyqi yettrynqps ikgtatfqqy wsvrtskrts
gtisvsehfr aweslgmnmg nmyevaltve gyqssgsanv ysntltiggq sggeqatrve
aesmtkggpy tsnitspfng valyangdnv sfnhsftkan ssfslrgasn nsnmarvdlr
iggqnrgtfy fgdqypavyt inninhgign qlvelivtad dgtwdayldy leir

FIG._16V

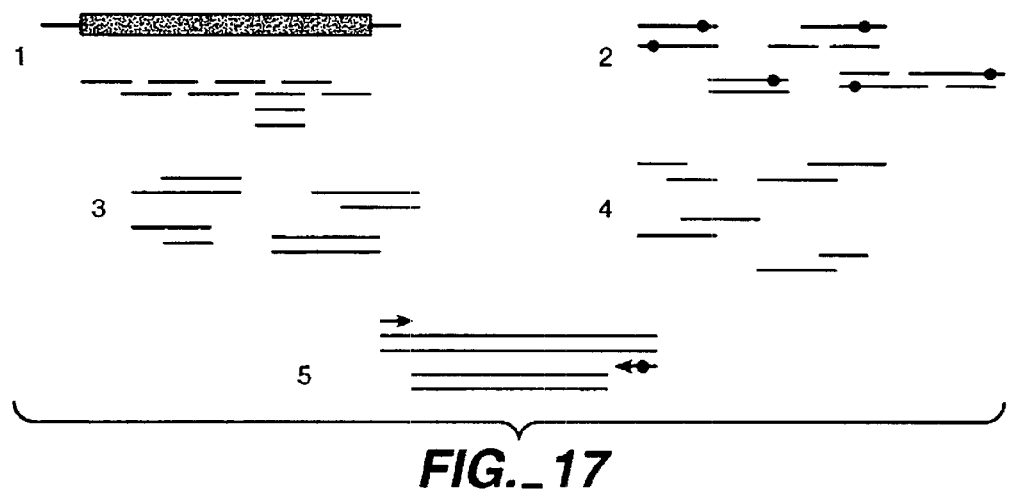
FIG._17
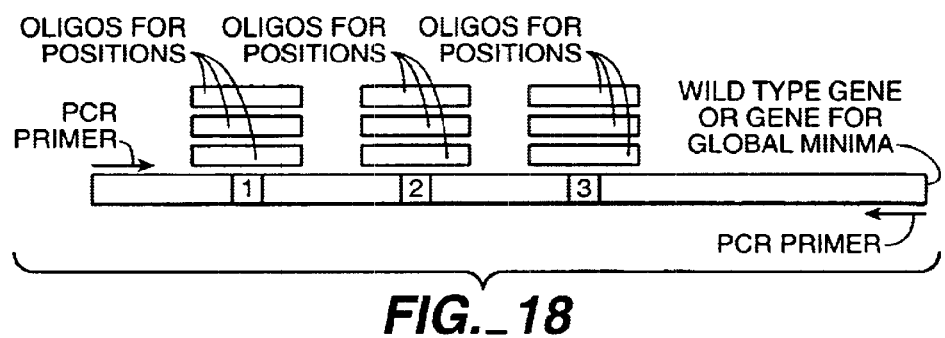
FIG._18

BLACK BOX = REGION TO BE MUTATED
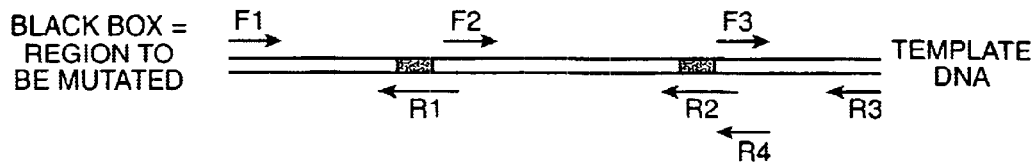
TEMPLATE DNA
STEP 1: SET UP 3 PCR REACTIONS:
  PRODUCTS:
TUBE 1: 
TUBE 2: 
TUBE 3: 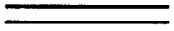
STEP 2: SET UP PCR REACTION WITH PRODUCTS OF TUBE 1 + PRODUCTS TUBE 2 + F1 + R4.
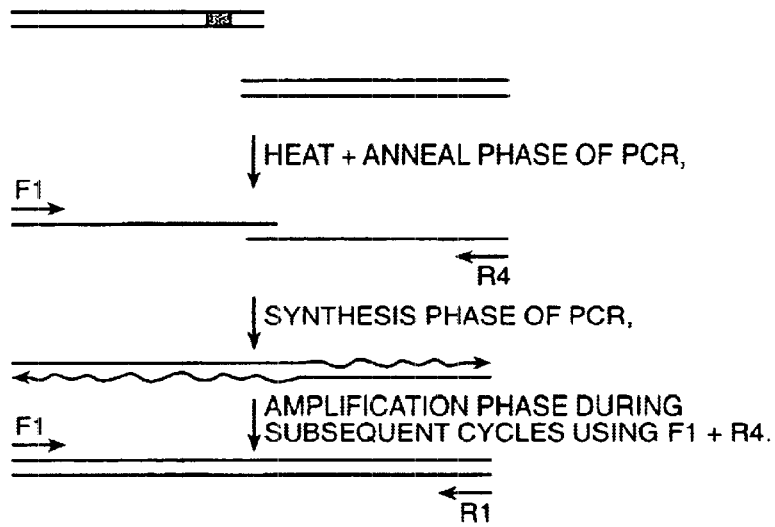
STEP 3: REPEAT STEP 2 USING PRODUCT FROM STEP 2 + PRODUCT FROM STEP 1, TUBE 3 + PRIMERS F1 + R3.
FIG._19

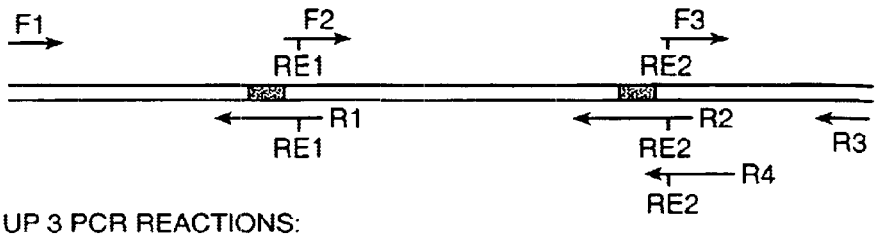

STEP 1: SET UP 3 PCR REACTIONS:

TUBE 1: 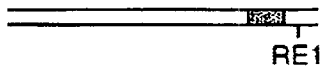

TUBE 2: 

TUBE 3: 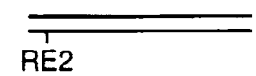

STEP 2: DIGEST PRODUCTS FROM STEP 1 WITH SUITABLE RESTRICTION ENDONUCLEASES.

STEP 3: LIGATE DIGESTED PRODUCT FROM STEP 2, TUBE 2 WITH DIGESTED PRODUCT FROM STEP 2, TUBE 1.

STEP 4: AMPLIFY VIA PCR LIGATED PRODUCTS OF STEP 3 WITH F1 + R4.

STEP 5: DIGEST AMPLIFIED PRODUCT OF STEP 4 WITH RESTRICTION ENDONUCLEASE #2.

STEP 6: LIGATE PRODUCT FROM STEP 5 WITH PRODUCT FROM STEP 2, TUBE 3.

STEP 7: AMPLIFY PRODUCT FROM STEP 6 WITH F1 + R3.

FIG._20

DIAGRAM 3

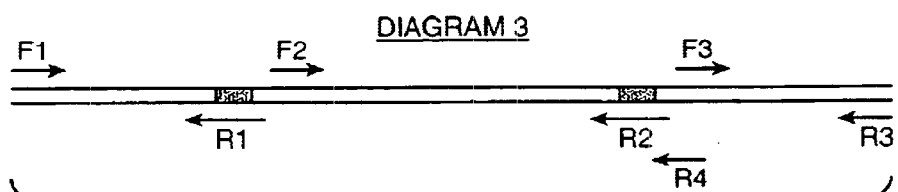

FIG._21

SEQUENCE LISTING

```
<160> NUMBER OF SEQ ID NOS: 34

<210> SEQ ID NO 1
<211> LENGTH: 213
<212> TYPE: PRT
<213> ORGANISM: Bacillus circulans
<220> FEATURE:
<221> NAME/KEY: SIGNAL
<222> LOCATION: (1)..(28)
<223> OTHER INFORMATION:
<220> FEATURE:
<221> NAME/KEY: mat_peptide
<222> LOCATION: (29)..()
<223> OTHER INFORMATION:

<400> SEQUENCE: 1

Met Phe Lys Phe Lys Lys Asn Phe Leu Val Gly Leu Ser Ala Ala Leu
            -25                 -20                 -15

Met Ser Ile Ser Leu Phe Ser Ala Thr Ala Ser Ala Ala Ser Thr Asp
        -10                  -5                  -1   1

Tyr Trp Gln Asn Trp Thr Asp Gly Gly Gly Ile Val Asn Ala Val Asn
  5                  10                  15                  20

Gly Ser Gly Gly Asn Tyr Ser Val Asn Trp Ser Asn Thr Gly Asn Phe
                 25                  30                  35

Val Val Gly Lys Gly Trp Thr Thr Gly Ser Pro Phe Arg Thr Ile Asn
             40                  45                  50

Tyr Asn Ala Gly Val Trp Ala Pro Asn Gly Asn Gly Tyr Leu Thr Leu
         55                  60                  65

Tyr Gly Trp Thr Arg Ser Pro Leu Ile Glu Tyr Tyr Val Val Asp Ser
     70                  75                  80

Trp Gly Thr Tyr Arg Pro Thr Gly Thr Tyr Lys Gly Thr Val Lys Ser
 85                  90                  95                 100

Asp Gly Gly Thr Tyr Asp Ile Tyr Thr Thr Thr Arg Tyr Asn Ala Pro
                105                 110                 115

Ser Ile Asp Gly Asp Arg Thr Thr Phe Thr Gln Tyr Trp Ser Val Arg
                120                 125                 130

Gln Ser Lys Arg Pro Thr Gly Ser Asn Ala Thr Ile Thr Phe Thr Asn
                135                 140                 145
```

His Val Asn Ala Trp Lys Ser His Gly Met Asn Leu Gly Ser Asn Trp
    150                 155                 160

Ala Tyr Gln Val Met Ala Thr Glu Gly Tyr Gln Ser Ser Gly Ser Ser
165                 170                 175                 180

Asn Val Thr Val Trp
            185

<210> SEQ ID NO 2
<211> LENGTH: 1349
<212> TYPE: DNA
<213> ORGANISM: Bacillus circulans

<400> SEQUENCE: 2

| | | | | | | |
|---|---|---|---|---|---|---|
| gaattcggtg | atgatggatt | cgatgcgctt | tagttctgag | gtgatcacgt | tgaagtaaag | 60 |
| ggcgtagtct | ccctcgacac | tccctttcag | aagctgaatg | aagcctttaa | gagcagtcat | 120 |
| cggatttctg | atttcatgag | caataccggc | tgcgagttcg | ccgacaacat | gaagggtatc | 180 |
| tgatttcgca | ggcgctcctc | caattctttt | cgctctgtta | cgtctttaaa | gatagccaag | 240 |
| ttcatatttt | gaataatatt | ccgtttaaat | gagaattcgt | ggtattatac | tgaaggggac | 300 |
| gatcaaaagc | tttggcgtta | gtaattaaaa | atgttttaaa | tgtatacgag | tgctgcctca | 360 |
| aagttggaaa | aaatattata | ggaggtaaca | tatgtttaag | tttaaaagaa | atttcttagt | 420 |
| tggattatcg | gcagctttaa | tgagtattag | cttgttttcg | gcaaccgcct | ctgcagctag | 480 |
| cacagactac | tggcaaaatt | ggactgatgg | gggcggtata | gtaaacgctg | tcaatgggtc | 540 |
| tggcgggaat | tacagtgtta | attggtctaa | taccggaaat | tttgttgttg | gtaaaggttg | 600 |
| gactacaggt | tcgccattta | ggacgataaa | ctataatgcc | ggagtttggg | cgccgaatgg | 660 |
| caatggatat | ttaactttat | atggttggac | gagatcacct | ctcatagaat | attatgtagt | 720 |
| ggattcatgg | gtacttata | gacctactgg | aacgtataaa | ggtactgtaa | aaagtgatgg | 780 |
| gggtacatat | gacatatata | caactacacg | ttataacgca | ccttccattg | atggcgatcg | 840 |
| cactactttt | acgcagtact | ggagtgttcg | ccagtcgaag | agaccaactg | gaagcaacgc | 900 |
| tacaatcact | ttcacgaatc | atgtgaacgc | atggaagagc | catggaatga | atctgggcag | 960 |
| taattgggct | taccaagtca | tggcgacaga | aggatatcaa | agtagtggaa | gttctaacgt | 1020 |
| aacagtgtgg | taacagatca | tccttaatca | ggggtagcta | acgggctgct | gatcgttcct | 1080 |
| tgagaagttt | tataatcaat | gattattaaa | atcgttagta | agggttaaag | gttgttttct | 1140 |
| actaggtgaa | cggccttgca | attgctggag | gtagggtatt | ctccatctgg | ttttataact | 1200 |
| tttcctatag | gttaatagaa | tggtatttaa | atgagaatgc | tacaattttt | tctagtcagc | 1260 |
| gcttgctcac | aacagacacc | tttacataac | tcttctttat | caaacataag | ccttattcaa | 1320 |
| aataaaaata | tctagtagtt | gacctgcag | | | | 1349 |

<210> SEQ ID NO 3
<211> LENGTH: 185
<212> TYPE: PRT
<213> ORGANISM: Artificial Sequence
<220> FEATURE:
<223> OTHER INFORMATION: synthetic

<400> SEQUENCE: 3

Ala Ser Thr Asp Tyr Trp Gln Asn Trp Thr Asp Gly Gly Gly Ile Val
1               5                   10                  15

Asn Ala Val Asn Gly Ser Gly Gly Asn Phe Ser Ile Asn Phe Ser Asn
            20                  25                  30

-continued

Thr Gly Asn Phe Val Val Gly Lys Gly Trp Thr Thr Gly Ser Pro Phe
             35                  40                  45

Arg Thr Ile Asn Phe Asn Ala Gly Val Phe Ala Pro Asn Gly Asn Val
 50                  55                  60

Tyr Leu Thr Leu Tyr Gly Trp Thr Arg Ser Pro Leu Ile Glu Phe Tyr
 65                  70                  75                  80

Val Val Asp Ser Trp Gly Thr Tyr Arg Pro Thr Gly Thr Tyr Lys Gly
                 85                  90                  95

Thr Val Lys Ser Asp Gly Gly Thr Phe Asp Ile Tyr Thr Thr Thr Arg
            100                 105                 110

Tyr Asn Ala Pro Ser Ile Asp Gly Asp Arg Thr Thr Phe Thr Gln Tyr
            115                 120                 125

Trp Ser Val Arg Gln Ser Lys Arg Pro Thr Gly Ser Asn Leu Thr Ile
130                 135                 140

Thr Phe Thr Asn His Val Asn Ala Trp Lys Ser His Gly Met Asn Leu
145                 150                 155                 160

Gly Ser Asn Trp Ala Tyr Gln Val Met Ala Leu Glu Gly Tyr Gln Ala
                165                 170                 175

Ser Gly Ser Ala Asn Ile Thr Val Trp
            180                 185

<210> SEQ ID NO 4
<211> LENGTH: 185
<212> TYPE: PRT
<213> ORGANISM: Artificial Sequence
<220> FEATURE:
<223> OTHER INFORMATION: synthetic

<400> SEQUENCE: 4

Ala Ser Thr Asp Tyr Trp Gln Asn Trp Thr Asp Gly Gly Gly Ile Val
 1               5                  10                  15

Asn Ala Val Asn Gly Ser Gly Gly Asn Tyr Ser Val Asn Trp Ser Asn
             20                  25                  30

Thr Gly Asn Phe Val Val Gly Lys Gly Trp Thr Thr Gly Ser Pro Phe
             35                  40                  45

Arg Thr Ile Asn Phe Asn Ala Gly Val Trp Ala Pro Asn Gly Asn Gly
 50                  55                  60

Tyr Leu Thr Leu Tyr Gly Trp Thr Arg Ser Pro Leu Ile Glu Tyr Tyr
 65                  70                  75                  80

Val Val Val Val Phe Gly Thr Tyr Arg Pro Thr Gly Thr Tyr Lys Gly
                 85                  90                  95

Thr Val Lys Ser Asp Gly Gly Thr Phe Asp Ile Tyr Thr Thr Thr Arg
            100                 105                 110

Tyr Asn Ala Pro Ser Ile Asp Gly Asp Arg Thr Thr Phe Thr Gln Tyr
            115                 120                 125

Trp Ser Val Met Gln Ser Lys Met Pro Thr Gly Ser Asn Leu Thr Leu
130                 135                 140

Thr Phe Thr Asn Phe Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 5

```
<211> LENGTH: 185
<212> TYPE: PRT
<213> ORGANISM: Artificial Sequence
<220> FEATURE:
<223> OTHER INFORMATION: synthetic

<400> SEQUENCE: 5

Ala Ser Thr Asp Tyr Trp Gln Asn Trp Thr Asp Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
                35                  40                  45

Arg Thr Ile Asn Phe Asn Ala Gly Val Trp Ala Pro Asn Gly Asn Gly
        50                  55                  60

Tyr Leu Thr Leu Tyr Gly Trp Thr Arg Ser Pro Leu Ile Glu Tyr Tyr
65                  70                  75                  80

Val Val Val Val Trp Gly Thr Tyr Arg Pro Thr Gly Thr Tyr Lys Gly
                85                  90                  95

Thr Val Lys Ser Asp Gly Thr Phe Asp Ile Tyr Thr Thr Thr Arg
                100                 105                 110

Tyr Asn Ala Pro Ser Ile Asp Gly Asp Arg Thr Thr Phe Thr Gln Tyr
            115                 120                 125

Trp Ser Val Met Gln Ser Lys Met Pro Thr Gly Ser Asn Leu Thr Leu
130                 135                 140

Thr Phe Thr Asn Phe Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 6
<211> LENGTH: 185
<212> TYPE: PRT
<213> ORGANISM: Artificial Sequence
<220> FEATURE:
<223> OTHER INFORMATION: synthetic

<400> SEQUENCE: 6

Ala Ser Thr Asp Tyr Trp Gln Asn Trp Thr Asp Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
                35                  40                  45

Arg Thr Ile Asn Phe Asn Ala Gly Val Trp Ala Pro Asn Gly Asn Gly
        50                  55                  60

Tyr Leu Thr Leu Tyr Gly Trp Thr Arg Ser Pro Leu Ile Glu Tyr Tyr
65                  70                  75                  80

Val Val Val Val Phe Gly Thr Tyr Arg Pro Thr Gly Thr Tyr Lys Gly
                85                  90                  95

Thr Val Lys Ser Asp Gly Thr Phe Asp Ile Tyr Thr Thr Thr Arg
                100                 105                 110

Tyr Asn Ala Pro Ser Ile Asp Gly Asp Arg Thr Thr Phe Thr Gln Tyr
            115                 120                 125

Trp Ser Val Ala Gln Ser Lys Leu Pro Thr Gly Ser Asn Leu Thr Leu
```

```
                   130                 135                 140
Thr Phe Thr Asn Phe Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 7
<211> LENGTH: 185
<212> TYPE: PRT
<213> ORGANISM: Artificial Sequence
<220> FEATURE:
<223> OTHER INFORMATION: synthetic

<400> SEQUENCE: 7

Ala Ser Thr Asp Tyr Trp Gln Asn Trp Thr Asp Gly Gly Gly Ile Val
1               5                  10                  15

Asn Ala Val Asn Gly Ser Gly Gly Asn Tyr Ser Val Asn Trp Ser Asn
                20                  25                  30

Thr Gly Asn Phe Val Val Gly Lys Gly Trp Thr Thr Gly Ser Pro Phe
            35                  40                  45

Arg Thr Ile Asn Phe Asn Ala Gly Val Trp Ala Pro Asn Gly Asn Gly
50                  55                  60

Tyr Leu Thr Leu Tyr Gly Trp Thr Arg Ser Pro Leu Ile Glu Tyr Tyr
65                  70                  75                  80

Val Val Val Ala Phe Gly Thr Tyr Arg Pro Thr Gly Thr Tyr Lys Gly
                85                  90                  95

Thr Val Lys Ser Asp Gly Gly Thr Phe Asp Ile Tyr Thr Thr Thr Arg
            100                 105                 110

Tyr Asn Ala Pro Ser Ile Asp Gly Asp Arg Thr Thr Phe Thr Gln Tyr
        115                 120                 125

Trp Ser Val Ala Gln Ser Lys Leu Pro Thr Gly Ser Asn Leu Thr Leu
130                 135                 140

Thr Phe Thr Asn Phe Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 8
<211> LENGTH: 185
<212> TYPE: PRT
<213> ORGANISM: Artificial Sequence
<220> FEATURE:
<223> OTHER INFORMATION: synthetic

<400> SEQUENCE: 8

Ala Ser Thr Asp Tyr Trp Gln Asn Trp Thr Asp Gly Gly Gly Ile Val
1               5                  10                  15

Asn Ala Val Asn Gly Ser Gly Gly Asn Tyr Ser Val Asn Trp Ser Asn
                20                  25                  30

Thr Gly Asn Phe Val Val Gly Lys Gly Trp Thr Thr Gly Ser Pro Phe
            35                  40                  45

Arg Thr Ile Asn Tyr Asn Ala Gly Val Trp Ala Pro Asn Gly Asn Gly
50                  55                  60
```

Tyr Leu Thr Leu Tyr Gly Trp Thr Arg Ser Pro Leu Ile Glu Phe Tyr
65                  70                  75                  80

Val Val Asp Ser Trp Gly Thr Tyr Arg Pro Thr Gly Thr Tyr Lys Ser
                85                  90                  95

Thr Thr Lys Val Asp Asp Ile Thr Phe Asp Ile Tyr Ile Thr Thr Arg
            100                 105                 110

Tyr Asn Ala Pro Ser Ile Asp Gly Asp Arg Thr Thr Phe Thr Gln Val
            115                 120                 125

Trp Ala Val Ala Gln Ser Lys Arg Pro Thr Gly Ser Asn Ala Thr Leu
130                 135                 140

Thr Phe Ile Glu Phe Ile Asn Ser Trp Lys Ser Tyr Gly Ile Asn Phe
145                 150                 155                 160

Gly Ser Asn Trp Ala Tyr Glu Val Met Ala Thr Glu Gly Tyr Gln Ser
                165                 170                 175

Ser Gly Ser Ser Asn Val Thr Val Trp
            180                 185

<210> SEQ ID NO 9
<211> LENGTH: 185
<212> TYPE: PRT
<213> ORGANISM: Artificial Sequence
<220> FEATURE:
<223> OTHER INFORMATION: synthetic

<400> SEQUENCE: 9

Ala Ser Thr Asp Tyr Trp Gln Asn Trp Thr Asp Gly Gly Gly Ile Val
1               5                   10                  15

Asn Ala Val Asn Gly Ser Gly Gly Asn Tyr Ser Val Asn Trp Ser Asn
                20                  25                  30

Thr Gly Asn Phe Val Val Gly Lys Gly Trp Thr Thr Gly Ser Pro Phe
            35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Phe Tyr
65                  70                  75                  80

Val Val Asp Ser Trp Gly Thr Tyr Arg Pro Thr Gly Thr Tyr Lys Gly
                85                  90                  95

Thr Val Lys Val Asp Gly Gly Thr Tyr Asp Ile Tyr Ile Thr Thr Arg
            100                 105                 110

Tyr Asn Ala Pro Ser Ile Asp Gly Asp Arg Thr Thr Phe Thr Gln Val
            115                 120                 125

Trp Ser Val Arg Gln Ser Lys Arg Pro Thr Gly Ser Asn Ala Thr Ile
130                 135                 140

Thr Phe Ile Glu His Ile Asn Ser Trp Lys Ser Tyr Gly Ile Asn Phe
145                 150                 155                 160

Gly Ser Asn Trp Ala Tyr Glu Val Met Ala Thr Glu Gly Tyr Gln Ser
                165                 170                 175

Ser Gly Ser Ser Asn Val Thr Val Trp
            180                 185

<210> SEQ ID NO 10
<211> LENGTH: 185
<212> TYPE: PRT
<213> ORGANISM: Artificial Sequence
<220> FEATURE:
<223> OTHER INFORMATION: synthetic

<400> SEQUENCE: 10

```
Ala Ser Thr Asp Tyr Trp Gln Asn Trp Thr Asp Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
            35                  40                  45

Arg Thr Ile Asn Tyr Asn Ala Gly Val Trp Ala Pro Asn Gly Asn Gly
        50                  55                  60

Tyr Leu Thr Leu Tyr Gly Trp Thr Arg Ser Pro Leu Ile Glu Phe Tyr
65                  70                  75                  80

Val Val Asp Ser Trp Gly Thr Tyr Arg Pro Thr Gly Thr Tyr Lys Ser
                85                  90                  95

Thr Thr Lys Val Asp Gly Gly Thr Phe Asp Ile Tyr Ile Thr Thr Arg
                100                 105                 110

Tyr Asn Ala Pro Ser Ile Asp Gly Asp Arg Thr Thr Phe Thr Gln Val
                115                 120                 125

Trp Ala Val Met Gln Ser Lys Arg Pro Thr Gly Ser Asn Ala Thr Leu
    130                 135                 140

Thr Phe Ile Glu Phe Val Asn Ser Trp Lys Ser Tyr Gly Ile Asn Leu
145                 150                 155                 160

Gly Ser Asn Trp Ala Tyr Glu Val Met Ala Thr Glu Gly Tyr Gln Ser
                165                 170                 175

Ser Gly Ser Ser Asn Val Thr Val Trp
            180                 185

<210> SEQ ID NO 11
<211> LENGTH: 185
<212> TYPE: PRT
<213> ORGANISM: Artificial Sequence
<220> FEATURE:
<223> OTHER INFORMATION: synthetic

<400> SEQUENCE: 11

Ala Ser Thr Asp Trp Trp Glu Asn Trp Thr Ile Gly Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Asp Val Ala Lys Gly Trp Thr Thr Gly Ser Pro Phe
            35                  40                  45

Arg Thr Ile Asn Tyr Asn Ala Gly Val Trp Ala Pro Asn Gly Trp Gly
        50                  55                  60

Glu Leu Glu Leu Tyr Gly Trp Thr Arg Ser Pro Leu Ile Glu Tyr Leu
65                  70                  75                  80

Val Val Asp Ser Trp Gly Thr Asn Arg Pro Thr Gly Thr Tyr Lys Gly
                85                  90                  95

Thr Val Lys Ser Asp Gly Gly Thr Tyr Asp Ile Tyr Thr Asp Thr Arg
                100                 105                 110

Tyr Asn Tyr Pro Ser Glu Asp Gly Asp Arg Thr Thr Met Thr Gln Tyr
                115                 120                 125

Ser Ser Val Arg Gln Ser Lys Arg Pro Thr Gly Ser Asn Ala Thr Ile
    130                 135                 140

Thr Phe Thr Asn His Val Asn Ala Trp Lys Ser His Gly Met Asn Leu
145                 150                 155                 160

Gly Ser Asn Trp Ala Tyr Gln Asp Met Ala Thr Glu Gly Tyr Gln Ser
                165                 170                 175
```

-continued

Ser Gly Ser Ser Asn Val Thr Val Trp
            180                 185

<210> SEQ ID NO 12
<211> LENGTH: 185
<212> TYPE: PRT
<213> ORGANISM: Artificial Sequence
<220> FEATURE:
<223> OTHER INFORMATION: synthetic

<400> SEQUENCE: 12

Ala Ser Thr Asp Tyr Trp Gln Asn Trp Thr Asp Gly Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Asp Val Ser Lys Gly Trp Thr Thr Gly Ser Pro Phe
        35                  40                  45

Arg Thr Ile Asn Tyr Asn Ala Gly Val Trp Ala Pro Asn Gly Trp Gly
    50                  55                  60

Glu Leu Glu Leu Tyr Gly Trp Thr Arg Ser Pro Leu Ile Glu Tyr Met
65                  70                  75                  80

Val Val Asp Ser Trp Gly Thr Trp Arg Pro Thr Gly Thr Tyr Lys Gly
                85                  90                  95

Thr Val Lys Ser Asp Gly Gly Thr Tyr Asp Ile Tyr Thr Asp Thr Arg
            100                 105                 110

Tyr Asn Asp Pro Ser Ile Asp Gly Asp Arg Thr Thr Phe Thr Gln Tyr
        115                 120                 125

Leu Ser Val Arg Gln Ser Lys Arg Pro Thr Gly Ser Asn Ala Thr Ile
    130                 135                 140

Thr Phe Thr Asn His Val Asn Ala Trp Lys Ser His Gly Met Asn Leu
145                 150                 155                 160

Gly Ser Asn Trp Ala Tyr Gln Asp Met Thr Thr Glu Gly Tyr Gln Ser
                165                 170                 175

Ser Gly Ser Ser Asn Val Thr Val Trp
            180                 185

<210> SEQ ID NO 13
<211> LENGTH: 213
<212> TYPE: PRT
<213> ORGANISM: Bacillus subtilis
<220> FEATURE:
<221> NAME/KEY: SIGNAL
<222> LOCATION: (1)..(28)
<223> OTHER INFORMATION:
<220> FEATURE:
<221> NAME/KEY: mat_peptide
<222> LOCATION: (29)..()
<223> OTHER INFORMATION:

<400> SEQUENCE: 13

Met Phe Lys Phe Lys Lys Asn Phe Leu Val Gly Leu Ser Ala Ala Leu
            -25                 -20                 -15

Met Ser Ile Ser Leu Phe Ser Ala Thr Ala Ser Ala Ala Ser Thr Asp
        -10                 -5                  -1  1

Tyr Trp Gln Asn Trp Thr Asp Gly Gly Gly Ile Val Asn Ala Val Asn
5                   10                  15                  20

Gly Ser Gly Gly Asn Tyr Ser Val Asn Trp Ser Asn Thr Gly Asn Phe
            25                  30                  35

Val Val Gly Lys Gly Trp Thr Thr Gly Ser Pro Phe Arg Thr Ile Asn

```
                40                  45                  50
Tyr Asn Ala Gly Val Trp Ala Pro Asn Gly Asn Gly Tyr Leu Thr Leu
             55                  60                  65

Tyr Gly Trp Thr Arg Ser Pro Leu Ile Glu Tyr Tyr Val Val Asp Ser
 70                  75                  80

Trp Gly Thr Tyr Arg Pro Thr Gly Thr Tyr Lys Gly Thr Val Lys Ser
 85                  90                  95                 100

Asp Gly Gly Thr Tyr Asp Ile Tyr Thr Thr Arg Tyr Asn Ala Pro
                100                 110                 115

Ser Ile Asp Gly Asp Arg Thr Thr Phe Thr Gln Tyr Trp Ser Val Arg
             120                 125                 130

Gln Ser Lys Arg Pro Thr Gly Ser Asn Ala Thr Ile Thr Phe Thr Asn
             135                 140                 145

His Val Asn Ala Trp Lys Ser His Gly Met Asn Leu Gly Ser Asn Trp
 150                 155                 160

Ala Tyr Gln Val Met Ala Thr Glu Gly Tyr Gln Ser Ser Gly Ser Ser
165                 170                 175                 180

Asn Val Thr Val Trp
                185

<210> SEQ ID NO 14
<211> LENGTH: 228
<212> TYPE: PRT
<213> ORGANISM: Bacillus pumilus

<400> SEQUENCE: 14

Met Asn Leu Arg Lys Leu Arg Leu Leu Phe Val Met Cys Ile Gly Leu
 1               5                  10                  15

Thr Leu Ile Leu Thr Ala Val Pro Ala His Ala Arg Thr Ile Thr Asn
             20                  25                  30

Asn Glu Met Gly Asn His Ser Gly Tyr Asp Tyr Glu Leu Trp Lys Asp
             35                  40                  45

Tyr Gly Asn Thr Ser Met Thr Leu Asn Asn Gly Gly Ala Phe Ser Ala
 50                  55                  60

Gly Trp Asn Asn Ile Gly Asn Ala Leu Phe Arg Lys Gly Lys Lys Phe
65                  70                  75                  80

Asp Ser Thr Arg Thr His His Gln Leu Gly Asn Ile Ser Ile Asn Tyr
             85                  90                  95

Asn Ala Ser Phe Asn Pro Gly Gly Asn Ser Tyr Leu Cys Val Tyr Gly
             100                 105                 110

Trp Thr Gln Ser Pro Leu Ala Glu Tyr Tyr Ile Val Asp Ser Trp Gly
             115                 120                 125

Thr Tyr Arg Pro Thr Gly Ala Tyr Lys Gly Ser Phe Tyr Ala Asp Gly
             130                 135                 140

Gly Thr Tyr Asp Ile Tyr Glu Thr Thr Arg Val Asn Gln Pro Ser Ile
145                 150                 155                 160

Ile Gly Ile Ala Thr Phe Lys Gln Tyr Trp Ser Val Arg Gln Thr Lys
             165                 170                 175

Arg Thr Ser Gly Thr Val Ser Val Ser Ala His Phe Arg Lys Trp Glu
             180                 185                 190

Ser Leu Gly Met Pro Met Gly Lys Met Tyr Glu Thr Ala Phe Thr Val
             195                 200                 205

Glu Gly Tyr Gln Ser Ser Gly Ser Ala Asn Val Met Thr Asn Gln Leu
 210                 215                 220
```

```
Phe Ile Gly Asn
225

<210> SEQ ID NO 15
<211> LENGTH: 335
<212> TYPE: PRT
<213> ORGANISM: Streptomyces lividans

<400> SEQUENCE: 15

Met Asn Leu Leu Val Gln Pro Arg Arg Arg Gly Pro Val Thr
1               5                   10                  15

Leu Leu Val Arg Ser Ala Trp Ala Val Ala Leu Ala Ala Leu Ala Ala
                20                  25                  30

Leu Met Leu Pro Gly Thr Ala Gln Ala Asp Thr Val Thr Thr Asn
        35                  40                  45

Gln Glu Gly Thr Asn Asn Gly Tyr Tyr Tyr Ser Phe Trp Thr Asp Ser
        50                  55                  60

Gln Gly Thr Val Ser Met Asn Met Gly Ser Gly Gln Tyr Ser Thr
65                  70                  75                  80

Ser Trp Arg Asn Thr Gly Asn Phe Val Ala Gly Lys Gly Trp Ala Asn
                85                  90                  95

Gly Gly Arg Arg Thr Val Gln Tyr Ser Gly Ser Phe Asn Pro Ser Gly
                100                 105                 110

Asn Ala Tyr Leu Ala Leu Tyr Gly Trp Thr Ser Asn Pro Leu Val Glu
                115                 120                 125

Tyr Tyr Ile Val Asp Asn Trp Gly Thr Tyr Arg Pro Thr Gly Glu Tyr
130                 135                 140

Lys Gly Thr Val Thr Ser Asp Gly Gly Thr Tyr Asp Ile Tyr Lys Thr
145                 150                 155                 160

Thr Arg Val Asn Lys Pro Ser Val Glu Gly Thr Arg Thr Phe Asp Gln
                165                 170                 175

Tyr Trp Ser Val Arg Gln Ser Lys Arg Thr Gly Gly Thr Ile Thr Thr
                180                 185                 190

Gly Asn His Phe Asp Ala Trp Ala Arg Ala Gly Met Pro Leu Gly Asn
                195                 200                 205

Phe Ser Tyr Tyr Met Ile Met Ala Thr Glu Gly Tyr Gln Ser Ser Gly
210                 215                 220

Thr Ser Ser Ile Asn Val Gly Gly Thr Gly Gly Asp Ser Gly Gly
225                 230                 235                 240

Gly Asp Asn Gly Gly Gly Gly Gly Cys Thr Ala Thr Val Ser Ala
                245                 250                 255

Gly Gln Lys Trp Gly Asp Arg Tyr Asn Leu Asp Val Ser Val Ser Gly
                260                 265                 270

Ala Ser Asp Trp Thr Val Thr Met Asn Val Pro Ser Pro Ala Lys Val
                275                 280                 285

Leu Ser Asn Trp Asn Val Asn Ala Ser Tyr Pro Ser Ala Gln Thr Leu
                290                 295                 300

Thr Ala Arg Leu Asn Gly Ser Gly Asn Asn Trp Gly Ala Thr Ile Gln
305                 310                 315                 320

Ala Asn Ala Asn Trp Thr Trp Pro Ser Val Ser Cys Ser Ala Gly
                325                 330                 335

<210> SEQ ID NO 16
<211> LENGTH: 240
<212> TYPE: PRT
<213> ORGANISM: Streptomyces lividans
```

<400> SEQUENCE: 16

```
Met Gln Gln Asp Gly Thr Gln Asp Arg Ile Lys Gln Ser Pro Ala
1               5                   10                  15

Pro Leu Asn Gly Met Ser Arg Arg Gly Phe Leu Gly Gly Ala Gly Thr
            20                  25                  30

Leu Ala Leu Ala Thr Ala Ser Gly Leu Leu Pro Gly Thr Ala His
        35                  40                  45

Ala Ala Thr Thr Ile Thr Thr Asn Gln Thr Gly Thr Asp Gly Met Tyr
    50                  55                  60

Tyr Ser Phe Trp Thr Asp Gly Gly Ser Val Ser Met Thr Leu Asn
65              70                  75                  80

Gly Gly Gly Ser Tyr Ser Thr Gln Trp Thr Asn Cys Gly Asn Phe Val
                85                  90                  95

Ala Gly Lys Gly Trp Ser Thr Gly Asp Gly Asn Val Arg Tyr Asn Gly
            100                 105                 110

Tyr Phe Asn Pro Val Gly Asn Gly Tyr Gly Cys Leu Tyr Gly Trp Thr
        115                 120                 125

Ser Asn Pro Leu Val Glu Tyr Tyr Ile Val Asp Asn Trp Gly Ser Tyr
    130                 135                 140

Arg Pro Thr Gly Thr Tyr Lys Gly Thr Val Ser Ser Asp Gly Gly Thr
145             150                 155                 160

Tyr Asp Ile Tyr Gln Thr Thr Arg Tyr Asn Ala Pro Ser Val Glu Gly
                165                 170                 175

Thr Lys Thr Phe Gln Gln Tyr Trp Ser Val Arg Gln Ser Lys Val Thr
            180                 185                 190

Ser Gly Ser Gly Thr Ile Thr Thr Gly Asn His Phe Asp Ala Trp Ala
        195                 200                 205

Arg Ala Gly Met Asn Met Gly Gln Phe Arg Tyr Tyr Met Ile Met Ala
    210                 215                 220

Thr Glu Gly Tyr Gln Ser Ser Gly Ser Ser Asn Ile Thr Val Ser Gly
225             230                 235                 240
```

<210> SEQ ID NO 17
<211> LENGTH: 261
<212> TYPE: PRT
<213> ORGANISM: Clostridium acetobutylicum

<400> SEQUENCE: 17

```
Met Leu Arg Arg Lys Val Ile Phe Thr Val Leu Ala Thr Leu Val Met
1               5                   10                  15

Thr Ser Leu Thr Ile Val Asp Asn Thr Ala Phe Ala Ala Thr Asn Leu
            20                  25                  30

Asn Thr Thr Glu Ser Thr Phe Ser Lys Glu Val Leu Ser Thr Gln Lys
        35                  40                  45

Thr Tyr Ser Ala Phe Asn Thr Gln Ala Ala Pro Lys Thr Ile Thr Ser
    50                  55                  60

Asn Glu Ile Gly Val Asn Gly Gly Tyr Asp Tyr Glu Leu Trp Lys Asp
65              70                  75                  80

Tyr Gly Asn Thr Ser Met Thr Leu Lys Asn Gly Gly Ala Phe Ser Cys
                85                  90                  95

Gln Trp Ser Asn Ile Gly Asn Ala Leu Phe Arg Lys Gly Lys Lys Phe
            100                 105                 110

Asn Asp Thr Gln Thr Tyr Lys Gln Leu Gly Asn Ile Ser Val Asn Tyr
        115                 120                 125
```

```
Asp Cys Asn Tyr Gln Pro Tyr Gly Asn Ser Tyr Leu Cys Val Tyr Gly
        130                 135                 140

Trp Thr Ser Ser Pro Leu Val Glu Tyr Tyr Ile Val Asp Ser Trp Gly
145                 150                 155                 160

Ser Trp Arg Pro Pro Gly Gly Thr Ser Lys Gly Thr Ile Thr Val Asp
                165                 170                 175

Gly Gly Ile Tyr Asp Ile Tyr Glu Thr Thr Arg Ile Asn Gln Pro Ser
            180                 185                 190

Ile Gln Gly Asn Thr Thr Phe Lys Gln Tyr Trp Ser Val Arg Arg Thr
        195                 200                 205

Lys Arg Thr Ser Gly Thr Ile Ser Val Ser Lys His Phe Ala Ala Trp
210                 215                 220

Glu Ser Lys Gly Met Pro Leu Gly Lys Met His Glu Thr Ala Phe Asn
225                 230                 235                 240

Ile Glu Gly Tyr Gln Ser Ser Gly Lys Ala Asp Val Asn Ser Met Ser
            245                 250                 255

Ile Asn Ile Gly Lys
            260

<210> SEQ ID NO 18
<211> LENGTH: 197
<212> TYPE: PRT
<213> ORGANISM: Schizophyllum commune

<400> SEQUENCE: 18

Ser Gly Thr Pro Ser Ser Thr Gly Thr Asp Gly Gly Tyr Tyr Tyr Ser
1               5                   10                  15

Trp Trp Thr Asp Gly Ala Gly Asp Ala Thr Tyr Gln Asn Asn Gly Gly
                20                  25                  30

Gly Ser Tyr Thr Leu Thr Trp Ser Gly Asn Asn Gly Asn Leu Val Gly
            35                  40                  45

Gly Lys Gly Trp Asn Pro Gly Ala Ala Ser Arg Ser Ile Ser Tyr Ser
        50                  55                  60

Gly Thr Tyr Gln Pro Asn Gly Asn Ser Tyr Leu Ser Val Tyr Gly Trp
65                  70                  75                  80

Thr Arg Ser Ser Leu Ile Glu Tyr Tyr Ile Val Glu Ser Tyr Gly Ser
                85                  90                  95

Tyr Asp Pro Ser Ser Ala Ala Ser His Lys Gly Ser Val Thr Cys Asn
                100                 105                 110

Gly Ala Thr Tyr Asp Ile Leu Ser Thr Trp Arg Tyr Asn Ala Pro Ser
            115                 120                 125

Ile Asp Gly Thr Gln Thr Phe Glu Gln Phe Trp Ser Val Arg Asn Pro
        130                 135                 140

Lys Lys Ala Pro Gly Gly Ser Ile Ser Gly Thr Val Asp Val Gln Cys
145                 150                 155                 160

His Phe Asp Ala Trp Lys Gly Leu Gly Met Asn Leu Gly Ser Glu His
                165                 170                 175

Asn Tyr Gln Ile Val Ala Thr Glu Gly Tyr Gln Ser Ser Gly Thr Ala
                180                 185                 190

Thr Ile Thr Val Thr
            195

<210> SEQ ID NO 19
<211> LENGTH: 190
<212> TYPE: PRT
```

```
<213> ORGANISM: Trichoderma viride

<400> SEQUENCE: 19

Gln Thr Ile Gly Pro Gly Thr Gly Phe Asn Asn Gly Tyr Phe Tyr Ser
1               5                   10                  15

Tyr Trp Asn Asp Gly His Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Thr Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ser Thr Phe Tyr Gln Tyr Trp Ser Val Arg Arg Thr His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 20
<211> LENGTH: 190
<212> TYPE: PRT
<213> ORGANISM: Trichoderma harzianum

<400> SEQUENCE: 20

Gln Thr Ile Gly Pro Gly Thr Gly Tyr Ser Asn Gly Tyr Tyr Tyr Ser
1               5                   10                  15

Tyr Trp Asn Asp Gly His Ala Gly Val Thr Tyr Thr Asn Gly Gly Gly
            20                  25                  30

Gly Ser Phe Thr Val Asn Trp Ser Asn Ser Gly Asn Phe Val Ala Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Ile Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Ser His Gly Leu Thr Leu Gly Thr Met Asp Tyr Gln Ile Val Ala Val
```

```
                    165                 170                 175
Glu Gly Tyr Phe Ser Ser Gly Ser Ala Ser Ile Thr Val Ser
                180                 185                 190

<210> SEQ ID NO 21
<211> LENGTH: 178
<212> TYPE: PRT
<213> ORGANISM: Trichoderma reesei

<400> SEQUENCE: 21

Ala Ser Ile Asn Tyr Asp Gln Asn Tyr Gln Thr Gly Gly Gln Val Ser
1               5                   10                  15

Tyr Ser Pro Ser Asn Thr Gly Phe Ser Val Asn Trp Asn Thr Gln Asp
            20                  25                  30

Asp Phe Val Val Gly Val Gly Trp Thr Thr Gly Ser Ser Ala Pro Ile
        35                  40                  45

Asn Phe Gly Gly Ser Phe Ser Val Asn Ser Gly Thr Gly Leu Leu Ser
    50                  55                  60

Val Tyr Gly Trp Ser Thr Asn Pro Leu Val Glu Tyr Tyr Ile Met Glu
65                  70                  75                  80

Asp Asn His Asn Tyr Pro Ala Gln Gly Thr Val Lys Gly Thr Val Thr
                85                  90                  95

Ser Asp Gly Ala Thr Tyr Thr Ile Trp Glu Asn Thr Arg Val Asn Glu
            100                 105                 110

Pro Ser Ile Gln Gly Thr Ala Thr Phe Asn Gln Tyr Ile Ser Val Arg
        115                 120                 125

Asn Ser Pro Arg Thr Ser Gly Thr Val Thr Val Gln Asn His Phe Asn
    130                 135                 140

Ala Trp Ala Ser Leu Gly Leu His Leu Gly Gln Met Asn Tyr Gln Val
145                 150                 155                 160

Val Ala Val Glu Gly Trp Gly Gly Ser Gly Ser Ala Ser Gln Ser Val
                165                 170                 175

Ser Asn

<210> SEQ ID NO 22
<211> LENGTH: 190
<212> TYPE: PRT
<213> ORGANISM: Trichoderma reesei
<220> FEATURE:
<221> NAME/KEY: MISC_FEATURE
<222> LOCATION: (1)..(1)
<223> OTHER INFORMATION: "Xaa" at position 1 is non-std-residue "PCA
      NH3+"

<400> SEQUENCE: 22

Xaa Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95
```

-continued

Asn Pro Ser Thr Gly Ala Thr Lys Leu Gly Glu Val Thr Ser Asp Gly
             100                 105                 110

Ser Val Tyr Asp Ile Tyr Arg Thr Gln Arg Val Asn Gln Pro Ser Ile
         115                 120                 125

Ile Gly Thr Ala Thr Phe Tyr Gln Tyr Trp Ser Val Arg Arg Asn His
     130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                 165                 170                 175

Glu Gly Tyr Phe Ser Ser Gly Ser Ala Ser Ile Thr Val Ser
             180                 185                 190

<210> SEQ ID NO 23
<211> LENGTH: 194
<212> TYPE: PRT
<213> ORGANISM: Paecilomyces variotii

<400> SEQUENCE: 23

Gly Thr Thr Pro Asn Ser Glu Gly Trp His Asp Gly Tyr Tyr Tyr Ser
1               5                   10                  15

Trp Trp Ser Asp Gly Gly Gly Asp Ser Thr Tyr Thr Asn Asn Ser Gly
             20                  25                  30

Gly Thr Tyr Glu Ile Thr Trp Gly Asn Gly Gly Asn Leu Val Gly Gly
         35                  40                  45

Lys Gly Trp Asn Pro Gly Leu Asn Ala Arg Ala Ile His Phe Thr Gly
     50                  55                  60

Val Tyr Gln Pro Asn Gly Thr Ser Tyr Leu Ser Val Tyr Gly Trp Thr
65                   70                  75                  80

Arg Asn Pro Leu Val Glu Tyr Tyr Ile Val Glu Asn Phe Gly Ser Ser
                 85                  90                  95

Asn Pro Ser Ser Gly Ser Thr Asp Leu Gly Thr Val Ser Cys Asp Gly
             100                 105                 110

Ser Thr Tyr Thr Leu Gly Gln Ser Thr Arg Tyr Asn Ala Pro Ser Ile
         115                 120                 125

Asp Gly Thr Gln Thr Phe Asn Gln Tyr Trp Ser Val Arg Gln Asp Lys
     130                 135                 140

Arg Ser Ser Gly Thr Val Gln Thr Gly Cys His Phe Asp Ala Trp Ala
145                 150                 155                 160

Ser Ala Gly Leu Asn Val Thr Gly Asp His Tyr Tyr Gln Ile Val Ala
                 165                 170                 175

Thr Glu Gly Tyr Phe Ser Ser Gly Tyr Ala Arg Ile Thr Val Ala Asp
             180                 185                 190

Val Gly

<210> SEQ ID NO 24
<211> LENGTH: 194
<212> TYPE: PRT
<213> ORGANISM: Thermomyces lanuginosus
<220> FEATURE:
<221> NAME/KEY: MISC_FEATURE
<222> LOCATION: (1)..(1)
<223> OTHER INFORMATION: "Xaa" at position 1 is non-std-residue "PCA
      NH3+"

<400> SEQUENCE: 24

Xaa Thr Thr Pro Asn Ser Glu Gly Trp His Asp Gly Tyr Tyr Tyr Ser
1               5                   10                  15

-continued

```
Trp Trp Ser Asp Gly Gly Ala Gln Ala Thr Tyr Thr Asn Leu Glu Gly
             20                  25                  30

Gly Thr Tyr Glu Ile Ser Trp Gly Asp Gly Gly Asn Leu Val Gly Gly
         35                  40                  45

Lys Gly Trp Asn Pro Gly Leu Asn Ala Arg Ala Ile His Phe Glu Gly
 50                  55                  60

Val Tyr Gln Pro Asn Gly Asn Ser Tyr Leu Ala Val Tyr Gly Trp Thr
 65                  70                  75                  80

Arg Asn Pro Leu Val Glu Tyr Tyr Ile Val Glu Asn Phe Gly Thr Tyr
                 85                  90                  95

Asp Pro Ser Ser Gly Ala Thr Asp Leu Gly Thr Val Glu Cys Asp Gly
                100                 105                 110

Ser Ile Tyr Arg Leu Gly Lys Thr Thr Arg Val Asn Ala Pro Ser Ile
            115                 120                 125

Asp Gly Thr Gln Thr Phe Asp Gln Tyr Trp Ser Val Arg Gln Asp Lys
        130                 135                 140

Arg Thr Ser Gly Thr Val Gln Thr Gly Cys His Phe Asp Ala Trp Ala
145                 150                 155                 160

Arg Ala Gly Leu Asn Val Asn Gly Asp His Tyr Tyr Gln Ile Val Ala
                165                 170                 175

Thr Glu Gly Tyr Phe Ser Ser Gly Tyr Ala Arg Ile Thr Val Ala Asp
                180                 185                 190

Val Gly

<210> SEQ ID NO 25
<211> LENGTH: 184
<212> TYPE: PRT
<213> ORGANISM: Aspergillus niger

<400> SEQUENCE: 25

Ser Ala Gly Ile Asn Tyr Val Gln Asn Tyr Asn Gly Asn Leu Gly Asp
1               5                  10                  15

Phe Thr Tyr Asp Glu Ser Ala Gly Thr Phe Ser Met Tyr Trp Glu Asp
            20                  25                  30

Gly Val Ser Ser Asp Phe Val Val Gly Leu Gly Trp Thr Thr Gly Ser
         35                  40                  45

Ser Asn Ala Ile Thr Tyr Ser Ala Glu Tyr Ser Ala Ser Gly Ser Ala
     50                  55                  60

Ser Tyr Leu Ala Val Tyr Gly Trp Val Asn Tyr Pro Gln Ala Glu Tyr
 65                  70                  75                  80

Tyr Ile Val Glu Asp Tyr Gly Asp Tyr Asn Pro Cys Ser Ser Ala Thr
                 85                  90                  95

Ser Leu Gly Thr Val Tyr Ser Asp Gly Ser Thr Tyr Gln Val Cys Thr
            100                 105                 110

Asp Thr Arg Thr Asn Glu Pro Ser Ile Thr Gly Thr Ser Thr Phe Thr
        115                 120                 125

Gln Tyr Phe Ser Val Arg Glu Ser Thr Arg Thr Ser Gly Thr Val Thr
    130                 135                 140

Val Ala Asn His Phe Asn Phe Trp Ala His His Gly Phe Gly Asn Ser
145                 150                 155                 160

Asp Phe Asn Tyr Gln Val Val Ala Val Glu Ala Trp Ser Gly Ala Gly
                165                 170                 175

Ser Ala Ser Val Thr Ile Ser Ser
            180
```

<210> SEQ ID NO 26
<211> LENGTH: 225
<212> TYPE: PRT
<213> ORGANISM: Aspergillus awamori var. kawachi

<400> SEQUENCE: 26

Met Leu Thr Lys Asn Leu Leu Cys Phe Ala Ala Lys Ala Val
1               5                   10                  15

Leu Ala Val Pro His Asp Ser Val Val Glu Arg Ser Asp Ala Leu His
            20                  25                  30

Lys Leu Ser Glu Arg Ser Thr Pro Ser Ser Thr Gly Glu Asn Asn Gly
            35                  40                  45

Tyr Tyr Tyr Ser Phe Trp Thr Asp Gly Gly Asp Val Thr Tyr Thr
50                  55                  60

Asn Gly Asn Ala Gly Ser Tyr Ser Val Glu Trp Ser Asn Val Gly Asn
65                  70                  75                  80

Phe Val Gly Gly Lys Gly Trp Asn Pro Gly Ser Ala Lys Asp Ile Thr
                85                  90                  95

Tyr Ser Gly Asn Phe Thr Pro Ser Gly Asn Gly Tyr Leu Ser Val Tyr
                100                 105                 110

Gly Trp Thr Thr Asp Pro Leu Ile Glu Tyr Tyr Ile Val Glu Ser Tyr
            115                 120                 125

Gly Asp Tyr Asn Pro Gly Ser Gly Gly Thr Thr Arg Gly Asn Val Ser
130                 135                 140

Ser Asp Gly Ser Val Tyr Asp Ile Tyr Thr Ala Thr Arg Thr Asn Ala
145                 150                 155                 160

Pro Ser Ile Gln Gly Thr Ala Thr Phe Ser Gln Tyr Trp Ser Val Arg
                165                 170                 175

Gln Asn Lys Arg Val Gly Gly Thr Val Thr Thr Ser Asn His Phe Asn
                180                 185                 190

Ala Trp Ala Lys Leu Gly Met Asn Leu Gly Thr His Asn Tyr Gln Ile
            195                 200                 205

Leu Ala Thr Glu Gly Tyr Gln Ser Ser Gly Ser Ser Ser Ile Thr Ile
    210                 215                 220

Gln
225

<210> SEQ ID NO 27
<211> LENGTH: 211
<212> TYPE: PRT
<213> ORGANISM: Aspergillus awamori var. kawachi

<400> SEQUENCE: 27

Met Lys Val Thr Ala Ala Ser Ala Gly Leu Leu Gly His Ala Phe Ala
1               5                   10                  15

Ala Pro Val Pro Gln Pro Val Leu Val Ser Arg Ser Ala Gly Ile Asn
            20                  25                  30

Tyr Val Gln Asn Tyr Asn Gly Asn Leu Ala Asp Phe Thr Tyr Asp Glu
            35                  40                  45

Ser Ala Gly Thr Phe Ser Met Tyr Trp Glu Asp Gly Val Ser Ser Asp
    50                  55                  60

Phe Val Val Gly Leu Gly Trp Thr Thr Gly Ser Ser Asn Ala Ile Ser
65                  70                  75                  80

Tyr Ser Ala Glu Tyr Ser Ala Ser Gly Ser Ser Tyr Leu Ala Val
                85                  90                  95

-continued

Tyr Gly Trp Val Asn Tyr Pro Gln Ala Glu Tyr Tyr Ile Val Glu Asp
                100                 105                 110

Tyr Gly Asp Tyr Asn Pro Cys Ser Ser Ala Thr Ser Leu Gly Thr Val
            115                 120                 125

Tyr Ser Asp Gly Ser Thr Tyr Gln Val Cys Thr Asp Thr Arg Thr Asn
        130                 135                 140

Glu Pro Ser Ile Thr Gly Thr Ser Thr Phe Thr Gln Tyr Phe Ser Val
145                 150                 155                 160

Arg Glu Ser Thr Arg Thr Ser Gly Thr Val Thr Val Ala Asn His Phe
                165                 170                 175

Asn Phe Trp Ala Gln His Gly Phe Gly Asn Ser Asp Phe Asn Tyr Gln
            180                 185                 190

Val Met Ala Val Glu Ala Trp Ser Gly Ala Gly Ser Ala Ser Val Thr
        195                 200                 205

Ile Ser Ser
    210

<210> SEQ ID NO 28
<211> LENGTH: 607
<212> TYPE: PRT
<213> ORGANISM: Neocallimastix patriciarum

<400> SEQUENCE: 28

Met Arg Thr Ile Lys Phe Phe Ala Val Ala Ile Ala Thr Val Ala
1               5                   10                  15

Lys Ala Gln Trp Gly Gly Gly Ala Ser Ala Gly Gln Arg Leu Thr
                20                  25                  30

Val Gly Asn Gly Gln Thr Gln His Lys Gly Val Ala Asp Gly Tyr Ser
            35                  40                  45

Tyr Glu Ile Trp Leu Asp Asn Thr Gly Gly Ser Gly Ser Met Thr Leu
        50                  55                  60

Gly Ser Gly Ala Thr Phe Lys Ala Glu Trp Asn Ala Ser Val Asn Arg
65                  70                  75                  80

Gly Asn Phe Leu Ala Arg Arg Gly Leu Asp Phe Gly Ser Gln Lys Lys
                85                  90                  95

Ala Thr Asp Tyr Ser Tyr Ile Gly Leu Asp Tyr Thr Ala Thr Tyr Arg
                100                 105                 110

Gln Thr Gly Ser Ala Ser Gly Asn Ser Arg Leu Cys Val Tyr Gly Trp
            115                 120                 125

Phe Gln Asn Arg Gly Val Gln Gly Val Pro Leu Val Glu Tyr Tyr Ile
        130                 135                 140

Ile Glu Asp Trp Val Asp Trp Val Pro Asp Ala Gln Gly Arg Met Val
145                 150                 155                 160

Thr Ile Asp Gly Ala Gln Tyr Lys Ile Phe Gln Met Asp His Thr Gly
                165                 170                 175

Pro Thr Ile Asn Gly Gly Ser Glu Thr Phe Lys Gln Tyr Phe Ser Val
            180                 185                 190

Arg Gln Gln Lys Arg Thr Ser Gly His Ile Thr Val Ser Asp His Phe
        195                 200                 205

Lys Glu Trp Ala Lys Gln Gly Trp Gly Ile Gly Asn Leu Tyr Glu Val
        210                 215                 220

Ala Leu Asn Ala Glu Gly Trp Gln Ser Ser Gly Ile Ala Asp Val Thr
225                 230                 235                 240

Lys Leu Asp Val Tyr Thr Thr Gln Lys Gly Ser Asn Pro Ala Pro Thr

```
                        245                 250                     255
        Ser Thr Gly Thr Val Pro Ser Ser Ala Gly Ser Thr Ala Asn
                        260                 265                 270

Gly Lys Lys Phe Thr Val Gly Asn Gly Gln Asn Gln His Lys Gly Val
                    275                 280                 285

Asn Asp Gly Phe Ser Tyr Glu Ile Trp Leu Asp Asn Thr Gly Gly Asn
                    290                 295                 300

Gly Ser Met Thr Leu Gly Ser Gly Ala Thr Phe Lys Ala Glu Trp Asn
        305                 310                 315                 320

Ala Ala Val Asn Arg Gly Asn Phe Leu Ala Arg Arg Gly Leu Asp Phe
                        325                 330                 335

Gly Ser Gln Lys Lys Ala Thr Asp Tyr Asp Tyr Ile Gly Leu Asp Tyr
                    340                 345                 350

Ala Ala Thr Tyr Lys Gln Thr Ala Ser Ala Ser Gly Asn Ser Arg Leu
                    355                 360                 365

Cys Val Tyr Gly Trp Phe Gln Asn Arg Gly Leu Asn Gly Val Pro Leu
                370                 375                 380

Val Glu Tyr Tyr Ile Ile Glu Asp Trp Val Asp Trp Val Pro Asp Ala
        385                 390                 395                 400

Gln Gly Lys Met Val Thr Ile Asp Gly Ala Gln Tyr Lys Ile Phe Gln
                        405                 410                 415

Met Asp His Thr Gly Pro Thr Ile Asn Gly Gly Ser Glu Thr Phe Lys
                    420                 425                 430

Gln Tyr Phe Ser Val Arg Gln Gln Lys Arg Thr Ser Gly His Ile Thr
                435                 440                 445

Val Ser Asp His Phe Lys Glu Trp Ala Lys Gln Gly Trp Gly Ile Gly
                450                 455                 460

Asn Leu Tyr Glu Val Ala Leu Asn Ala Glu Gly Trp Gln Ser Ser Gly
        465                 470                 475                 480

Val Ala Asp Val Thr Leu Leu Asp Val Tyr Thr Thr Pro Lys Gly Ser
                        485                 490                 495

Ser Pro Ala Thr Ser Ala Ala Pro Arg Thr Thr Thr Arg Thr Thr Thr
                    500                 505                 510

Arg Thr Lys Ser Leu Pro Thr Asn Tyr Asn Lys Cys Ser Ala Arg Ile
                    515                 520                 525

Thr Ala Gln Gly Tyr Lys Cys Cys Ser Asp Pro Asn Cys Val Val Tyr
                530                 535                 540

Tyr Thr Asp Glu Asp Gly Thr Trp Gly Val Glu Asn Asn Asp Trp Cys
        545                 550                 555                 560

Gly Cys Gly Val Glu Gln Cys Ser Ser Lys Ile Thr Ser Gln Gly Tyr
                        565                 570                 575

Lys Cys Cys Ser Asp Pro Asn Cys Val Val Phe Tyr Thr Asp Asp Asp
                    580                 585                 590

Gly Lys Trp Gly Val Glu Asn Asn Asp Trp Cys Gly Cys Gly Phe
                    595                 600                 605

<210> SEQ ID NO 29
<211> LENGTH: 221
<212> TYPE: PRT
<213> ORGANISM: Cochliobolus carbonum

<400> SEQUENCE: 29

Met Val Ser Phe Thr Ser Ile Ile Thr Ala Ala Val Ala Ala Thr Gly
        1               5                   10                  15
```

```
Ala Leu Ala Ala Pro Ala Thr Asp Val Ser Leu Val Ala Arg Gln Asn
             20                  25                  30

Thr Pro Asn Gly Glu Gly Thr His Asn Gly Cys Phe Trp Ser Trp Trp
         35                  40                  45

Ser Asp Gly Gly Ala Arg Ala Thr Tyr Thr Asn Gly Ala Gly Gly Ser
     50                  55                  60

Tyr Ser Val Ser Trp Gly Ser Gly Asn Leu Val Gly Gly Lys Gly
 65                  70                  75                  80

Trp Asn Pro Gly Thr Ala Arg Thr Ile Thr Tyr Ser Gly Thr Tyr Asn
                 85                  90                  95

Tyr Asn Gly Asn Ser Tyr Leu Ala Val Tyr Gly Trp Thr Arg Asn Pro
             100                 105                 110

Leu Val Glu Tyr Tyr Val Val Glu Asn Phe Gly Thr Tyr Asp Pro Ser
         115                 120                 125

Ser Gln Ser Gln Asn Lys Gly Thr Val Thr Ser Asp Gly Ser Ser Tyr
     130                 135                 140

Lys Ile Ala Gln Ser Thr Arg Thr Asn Gln Pro Ser Ile Asp Gly Thr
145                 150                 155                 160

Arg Thr Phe Gln Gln Tyr Trp Ser Val Arg Gln Asn Lys Arg Ser Ser
                 165                 170                 175

Gly Ser Val Asn Met Lys Thr His Phe Asp Ala Trp Ala Ser Lys Gly
             180                 185                 190

Met Asn Leu Gly Gln His Tyr Tyr Gln Ile Val Ala Thr Glu Gly Tyr
         195                 200                 205

Phe Ser Thr Gly Asn Ala Gln Ile Thr Val Asn Cys Pro
     210                 215                 220

<210> SEQ ID NO 30
<211> LENGTH: 512
<212> TYPE: PRT
<213> ORGANISM: Clostridium stercorarium

<400> SEQUENCE: 30

Met Lys Arg Lys Val Lys Lys Met Ala Ala Met Ala Thr Ser Ile Ile
 1               5                  10                  15

Met Ala Ile Met Ile Ile Leu His Ser Ile Pro Val Leu Ala Gly Arg
             20                  25                  30

Ile Ile Tyr Asp Asn Glu Thr Gly Thr His Gly Gly Tyr Asp Tyr Glu
         35                  40                  45

Leu Trp Lys Asp Tyr Gly Asn Thr Ile Met Glu Leu Asn Asp Gly Gly
     50                  55                  60

Thr Phe Ser Cys Gln Trp Ser Asn Ile Gly Asn Ala Leu Phe Arg Lys
 65                  70                  75                  80

Gly Arg Lys Phe Asn Ser Asp Lys Thr Tyr Gln Glu Leu Gly Asp Ile
                 85                  90                  95

Val Val Glu Tyr Gly Cys Asp Tyr Asn Pro Asn Gly Asn Ser Tyr Leu
             100                 105                 110

Cys Val Tyr Gly Trp Thr Arg Asn Pro Leu Val Glu Tyr Tyr Ile Val
         115                 120                 125

Glu Ser Trp Gly Ser Trp Arg Pro Pro Gly Ala Thr Pro Lys Gly Thr
     130                 135                 140

Ile Thr Gln Trp Met Ala Gly Thr Tyr Glu Ile Tyr Glu Thr Thr Arg
145                 150                 155                 160

Val Asn Gln Pro Ser Ile Asp Gly Thr Ala Thr Phe Gln Gln Tyr Trp
                 165                 170                 175
```

```
Ser Val Arg Thr Ser Lys Arg Thr Ser Gly Thr Ile Ser Val Thr Glu
                180                 185                 190

His Phe Lys Gln Trp Glu Arg Met Gly Met Arg Met Gly Lys Met Tyr
            195                 200                 205

Glu Val Ala Leu Thr Val Glu Gly Tyr Gln Ser Ser Gly Tyr Ala Asn
        210                 215                 220

Val Tyr Lys Asn Glu Ile Arg Ile Gly Ala Asn Pro Thr Pro Ala Pro
225                 230                 235                 240

Ser Gln Ser Pro Ile Arg Arg Asp Ala Phe Ser Ile Ile Glu Ala Glu
                245                 250                 255

Glu Tyr Asn Ser Thr Asn Ser Ser Thr Leu Gln Val Ile Gly Thr Pro
            260                 265                 270

Asn Asn Gly Arg Gly Ile Gly Tyr Ile Glu Asn Gly Asn Thr Val Thr
        275                 280                 285

Tyr Ser Asn Ile Asp Phe Gly Ser Gly Ala Thr Gly Phe Ser Ala Thr
        290                 295                 300

Val Ala Thr Glu Val Asn Thr Ser Ile Gln Ile Arg Ser Asp Ser Pro
305                 310                 315                 320

Thr Gly Thr Leu Leu Gly Thr Leu Tyr Val Ser Ser Thr Gly Ser Trp
                325                 330                 335

Asn Thr Tyr Gln Thr Val Ser Thr Asn Ile Ser Lys Ile Thr Gly Val
            340                 345                 350

His Asp Ile Val Leu Val Phe Ser Gly Pro Val Asn Val Asp Asn Phe
        355                 360                 365

Ile Phe Ser Arg Ser Ser Pro Val Pro Ala Pro Gly Asp Asn Thr Arg
        370                 375                 380

Asp Ala Tyr Ser Ile Ile Gln Ala Glu Asp Tyr Asp Ser Ser Tyr Gly
385                 390                 395                 400

Pro Asn Leu Gln Ile Phe Ser Leu Pro Gly Gly Ser Ala Ile Gly
                405                 410                 415

Tyr Ile Glu Asn Gly Tyr Ser Thr Thr Tyr Lys Asn Ile Asp Phe Gly
            420                 425                 430

Asp Gly Ala Thr Ser Val Thr Ala Arg Val Ala Thr Gln Asn Ala Thr
        435                 440                 445

Thr Ile Gln Val Arg Leu Gly Ser Pro Ser Gly Thr Leu Leu Gly Thr
        450                 455                 460

Ile Tyr Val Gly Ser Thr Gly Ser Phe Asp Thr Tyr Arg Asp Val Ser
465                 470                 475                 480

Ala Thr Ile Ser Asn Thr Ala Gly Val Lys Asp Ile Val Leu Val Phe
                485                 490                 495

Ser Gly Pro Val Asn Val Asp Trp Phe Val Phe Ser Lys Ser Gly Thr
            500                 505                 510

<210> SEQ ID NO 31
<211> LENGTH: 954
<212> TYPE: PRT
<213> ORGANISM: Ruminococcus flavefaciens

<400> SEQUENCE: 31

Met Lys Leu Ser Lys Ile Lys Lys Val Leu Ser Gly Thr Val Ser Ala
1               5                   10                  15

Leu Met Ile Ala Ser Ala Ala Pro Val Val Ala Ser Ala Ala Asp Gln
            20                  25                  30

Gln Thr Arg Gly Asn Val Gly Gly Tyr Asp Tyr Glu Met Trp Asn Gln
```

-continued

```
             35                  40                  45
Asn Gly Gln Gly Gln Ala Ser Met Asn Pro Gly Ala Gly Ser Phe Thr
 50                  55                  60

Cys Ser Trp Ser Asn Ile Glu Asn Phe Leu Ala Arg Met Gly Lys Asn
 65                  70                  75                  80

Tyr Asp Ser Gln Lys Lys Asn Tyr Lys Ala Phe Gly Asn Ile Val Leu
                 85                  90                  95

Thr Tyr Asp Val Glu Tyr Thr Pro Arg Gly Asn Ser Tyr Met Cys Val
            100                 105                 110

Tyr Gly Trp Thr Arg Asn Pro Leu Met Glu Tyr Tyr Ile Val Glu Gly
            115                 120                 125

Trp Gly Asp Trp Arg Pro Pro Gly Asn Asp Gly Glu Val Lys Gly Thr
130                 135                 140

Val Ser Ala Asn Gly Asn Thr Tyr Asp Ile Arg Lys Thr Met Arg Tyr
145                 150                 155                 160

Asn Gln Pro Ser Leu Asp Gly Thr Ala Thr Phe Pro Gln Tyr Trp Ser
                165                 170                 175

Val Arg Gln Thr Ser Gly Ser Ala Asn Asn Gln Thr Asn Tyr Met Lys
            180                 185                 190

Gly Thr Ile Asp Val Thr Lys His Phe Asp Ala Trp Ser Ala Ala Gly
            195                 200                 205

Leu Asp Met Ser Gly Thr Leu Tyr Glu Val Ser Leu Asn Ile Glu Gly
210                 215                 220

Tyr Arg Ser Asn Gly Ser Ala Asn Val Lys Ser Val Ser Val Thr Gln
225                 230                 235                 240

Gly Gly Ser Ser Asp Asn Gly Gln Gln Gln Asn Asn Asp Trp Asn
                245                 250                 255

Gln Gln Asn Asn Asn Gln Gln Gln Asn Asn Asp Trp Asn Asn Trp Gly
            260                 265                 270

Gln Gln Asn Asn Asp Trp Asn Gln Trp Asn Asn Gln Gly Gln Gln Asn
            275                 280                 285

Asn Asp Trp Asn Asn Trp Gly Gln Gln Asn Asn Asp Trp Asn Gln Trp
            290                 295                 300

Asn Asn Gln Gly Gln Gln Asn Asn Asp Trp Asn Asn Trp Gly Gln
305                 310                 315                 320

Gln Asn Asn Asp Trp Asn Gln Trp Asn Asn Gln Gly Gln Gln Asn
            325                 330                 335

Asn Asp Trp Asn Asn Trp Gly Gln Gln Asn Asn Asp Trp Asn Gln Trp
            340                 345                 350

Asn Asn Gln Gly Gln Gln Asn Asn Asp Trp Asn Asn Trp Gly Gln
            355                 360                 365

Gln Asn Asn Asp Trp Asn Gln Trp Asn Asn Gln Asn Asn Gln Gln
            370                 375                 380

Asn Ala Trp Asn Gly Trp Asp Asn Asn Asn Trp Asn Gln Asn Asn
385                 390                 395                 400

Gln Gln Gln Asn Asn Trp Asp Trp Asn Asn Gln Asn Trp Asn Asn
                405                 410                 415

Asn Gln Gln Gln Asn Asn Asp Trp Asn Gln Trp Asn Asn Gln Asn Asn
            420                 425                 430

Trp Asn Asn Asn Gln Gln Gln Asn Asn Asp Trp Asn Gln Trp Asn Asn
            435                 440                 445

Gln Gly Gln Gln Asn Asn Asp Trp Asn Gln Trp Asn Asn Gln Asn Asn
450                 455                 460
```

-continued

```
Trp Asn Gln Asn Asn Gln Gln Asn Ala Trp Asn Gly Trp Asp Asn
465                 470                 475                 480

Asn Asn Asn Trp Asn Gln Trp Asp Gln Asn Asn Gln Trp Asn Gln
            485                 490                 495

Gln Gln Asn Asn Thr Trp Asp Trp Asn Asn Gln Asn Asn Trp Asn Asn
                500                 505                 510

Asn Gln Gln Asn Asn Asp Trp Asn Gln Trp Asn Asn Gln Gly Gln Gln
                515                 520                 525

Gln Asn Asn Asp Trp Asn Gln Trp Asn Gln Asn Asn Asn Gln Asn
530                 535                 540

Asn Gly Trp Asp Trp Asn Asn Gln Asn Trp Asn Gln Asn Asn Asn
545                 550                 555                 560

Gln Gln Asn Ala Trp Asn Gly Trp Asp Asn Asn Asn Trp Asn Gln
                565                 570                 575

Trp Gly Gly Gln Asn Asn Asp Trp Asn Gln Gln Gln Asn Asn Asp
                580                 585                 590

Trp Asn Gln Trp Asn Asn Gln Gly Gln Gln Gln Asn Asn Asp Trp Asn
                595                 600                 605

Asn Gln Asn Asn Trp Asn Gln Gly Gln Gln Asn Asn Asn Asn Ser Ala
610                 615                 620

Gly Ser Ser Asp Ser Leu Lys Gly Ala Phe Ser Lys Tyr Phe Lys Ile
625                 630                 635                 640

Gly Thr Ser Val Ser Pro His Glu Leu Asn Ser Gly Ala Asp Phe Leu
                645                 650                 655

Lys Lys His Tyr Asn Ser Ile Thr Pro Glu Asn Glu Leu Lys Pro Glu
                660                 665                 670

Ser Ile Leu Asp Gln Gly Ala Cys Gln Gln Lys Gly Asn Asn Val Asn
                675                 680                 685

Thr Gln Ile Ser Leu Ser Arg Ala Ala Gln Thr Leu Lys Phe Cys Glu
                690                 695                 700

Gln Asn Gly Ile Ala Leu Arg Gly His Thr Phe Val Trp Tyr Ser Gln
705                 710                 715                 720

Thr Pro Asp Trp Phe Phe Arg Glu Asn Phe Ser Gln Asn Gly Ala Tyr
                725                 730                 735

Val Ser Lys Asp Ile Met Asn Gln Arg Leu Glu Ser Met Ile Lys Asn
                740                 745                 750

Thr Phe Ala Ala Leu Lys Ser Gln Tyr Pro Asn Leu Asp Val Tyr Ser
                755                 760                 765

Tyr Asp Val Cys Asn Glu Leu Phe Leu Asn Asn Gly Gly Met Arg
770                 775                 780

Gly Ala Asp Asn Ser Asn Trp Val Lys Ile Tyr Gly Asp Asp Ser Phe
785                 790                 795                 800

Val Ile Asn Ala Phe Lys Tyr Ala Arg Gln Tyr Ala Pro Ala Gly Cys
                805                 810                 815

Lys Leu Tyr Leu Asn Asp Tyr Asn Glu Tyr Ile Pro Ala Lys Thr Asn
                820                 825                 830

Asp Ile Tyr Asn Met Ala Met Lys Leu Lys Gln Leu Gly Tyr Ile Asp
                835                 840                 845

Gly Ile Gly Met Gln Ser His Leu Ala Thr Asn Tyr Pro Asp Ala Asn
                850                 855                 860

Thr Tyr Glu Thr Ala Leu Lys Lys Phe Leu Ser Thr Gly Leu Glu Val
865                 870                 875                 880
```

-continued

```
Gln Ile Thr Glu Leu Asp Ile Thr Cys Thr Asn Ser Ala Glu Gln Ala
                885                 890                 895

Asp Leu Tyr Glu Lys Ile Phe Lys Leu Ala Met Gln Asn Ser Ala Gln
            900                 905                 910

Ile Pro Ala Val Thr Ile Trp Gly Thr Gln Asp Thr Val Ser Trp Arg
        915                 920                 925

Ser Ser Gln Asn Pro Leu Leu Phe Ser Ala Gly Tyr Gln Pro Lys Pro
    930                 935                 940

Ala Tyr Asp Arg Val Met Ala Leu Ala Lys
945                 950

<210> SEQ ID NO 32
<211> LENGTH: 608
<212> TYPE: PRT
<213> ORGANISM: Fibrobacter succinogenes

<400> SEQUENCE: 32

Met Lys Thr Phe Ser Val Thr Lys Ser Ser Val Val Phe Ala Met Ala
1               5                   10                  15

Leu Gly Met Ala Ser Thr Ala Phe Ala Gln Asp Phe Cys Ser Asn Ala
            20                  25                  30

Gln His Ser Gly Gln Lys Val Thr Ile Thr Ser Asn Gln Thr Gly Lys
        35                  40                  45

Ile Gly Asp Ile Gly Tyr Glu Leu Trp Asp Glu Asn Gly His Gly Gly
    50                  55                  60

Ser Ala Thr Phe Tyr Ser Asp Gly Ser Met Asp Cys Asn Ile Thr Gly
65                  70                  75                  80

Ala Lys Asp Tyr Leu Cys Arg Ala Gly Leu Ser Leu Gly Ser Asn Lys
                85                  90                  95

Thr Tyr Lys Glu Leu Gly Gly Asp Met Ile Ala Glu Phe Lys Leu Val
            100                 105                 110

Lys Ser Gly Ala Gln Asn Val Gly Tyr Ser Tyr Ile Gly Ile Tyr Gly
        115                 120                 125

Trp Met Glu Gly Val Ser Gly Thr Pro Ser Gln Leu Val Glu Tyr Tyr
    130                 135                 140

Val Ile Asp Asn Thr Leu Ala Asn Asp Met Pro Gly Ser Trp Ile Gly
145                 150                 155                 160

Asn Glu Arg Lys Gly Thr Ile Thr Val Asp Gly Gly Thr Tyr Ile Val
                165                 170                 175

Tyr Arg Asn Thr Arg Thr Gly Pro Ala Ile Lys Asn Ser Gly Asn Val
            180                 185                 190

Thr Phe Tyr Gln Tyr Phe Ser Val Arg Thr Ser Pro Arg Asp Cys Gly
        195                 200                 205

Thr Ile Asn Ile Ser Glu His Met Arg Gln Trp Glu Lys Met Gly Leu
    210                 215                 220

Thr Met Gly Lys Leu Tyr Glu Ala Lys Val Leu Gly Glu Ala Gly Asn
225                 230                 235                 240

Val Asn Gly Glu Val Arg Gly Gly His Met Asp Phe Pro His Ala Lys
                245                 250                 255

Val Tyr Val Lys Asn Gly Ser Asp Pro Val Ser Ser Ser Val Lys
            260                 265                 270

Ser Ser Ser Ser Thr Asp Ala Pro Lys Ser Ser Ser Lys Gly Asn
        275                 280                 285

Gly Asn Val Ser Gly Lys Ile Asp Ala Cys Lys Asp Val Met Gly His
    290                 295                 300
```

```
Glu Gly Lys Glu Thr Arg Thr Gln Gly Gln Asn Asn Ser Ser Val Thr
305                 310                 315                 320

Gly Asn Val Gly Ser Ser Pro Tyr His Tyr Glu Ile Trp Tyr Gln Gly
            325                 330                 335

Gly Asn Asn Ser Met Thr Phe Tyr Asp Asn Gly Thr Tyr Lys Ala Ser
            340                 345                 350

Trp Asn Gly Thr Asn Asp Phe Leu Ala Arg Val Gly Phe Lys Tyr Asp
            355                 360                 365

Glu Lys His Thr Tyr Glu Glu Leu Gly Pro Ile Asp Ala Tyr Tyr Lys
            370                 375                 380

Trp Ser Lys Gln Gly Ser Ala Gly Gly Tyr Asn Tyr Ile Gly Ile Tyr
385                 390                 395                 400

Gly Trp Thr Val Asp Pro Leu Val Glu Tyr Tyr Ile Val Asp Asp Trp
                405                 410                 415

Phe Asn Lys Pro Gly Ala Asn Leu Leu Gly Gln Arg Lys Gly Glu Phe
                420                 425                 430

Thr Val Asp Gly Asp Thr Tyr Glu Ile Trp Gln Asn Thr Arg Val Gln
                435                 440                 445

Gln Pro Ser Ile Lys Gly Thr Gln Thr Phe Pro Gln Tyr Phe Ser Val
        450                 455                 460

Arg Lys Ser Ala Arg Ser Cys Gly His Ile Asp Ile Thr Ala His Met
465                 470                 475                 480

Lys Lys Trp Glu Glu Leu Gly Met Lys Met Gly Lys Met Tyr Glu Ala
                485                 490                 495

Lys Val Leu Val Glu Ala Gly Gly Ser Gly Ser Phe Asp Val Thr
                500                 505                 510

Tyr Phe Lys Met Thr Asp Lys Ala His Pro Leu Ala Gln Pro Glu Pro
        515                 520                 525

Glu Ser Ser Ser Glu Ala Lys Val Glu Ser Ser Ser Thr Val
        530                 535                 540

Ala Leu His Ala Ala Pro Lys Met Glu Leu Lys Ser Gly Asn Phe Gln
545                 550                 555                 560

Val Phe Asp Met Gln Gly Arg Phe Leu Gly Thr Val Lys Leu Asp Ala
                565                 570                 575

Gly Ala Ser Val Ala Gln Val Leu Lys Ala Asn Phe Lys Asn Ala Gly
            580                 585                 590

Ile Tyr Met Val Lys Gln Gly Asn Phe Met Gln Arg Val Ala Val Lys
        595                 600                 605

<210> SEQ ID NO 33
<211> LENGTH: 211
<212> TYPE: PRT
<213> ORGANISM: Aspergillus tubingensis

<400> SEQUENCE: 33

Met Lys Val Thr Ala Ala Phe Ala Gly Leu Leu Val Thr Ala Phe Ala
1               5                   10                  15

Ala Pro Ala Pro Glu Pro Asp Leu Val Ser Arg Ser Ala Gly Ile Asn
            20                  25                  30

Tyr Val Gln Asn Tyr Asn Gly Asn Leu Gly Asp Phe Thr Tyr Asp Glu
        35                  40                  45

Ser Ala Gly Thr Phe Ser Met Tyr Trp Glu Asp Gly Val Ser Ser Asp
    50                  55                  60

Phe Val Val Gly Leu Gly Trp Thr Thr Gly Ser Ser Asn Ala Ile Thr
```

```
                 65                  70                  75                  80
Tyr Ser Ala Glu Tyr Ser Ala Ser Gly Ser Ala Ser Tyr Leu Ala Val
                 85                  90                  95

Tyr Gly Trp Val Asn Tyr Pro Gln Ala Glu Tyr Ile Val Glu Asp
                100                 105                 110

Tyr Gly Asp Tyr Asn Pro Cys Ser Ser Ala Thr Ser Leu Gly Thr Val
                115                 120                 125

Tyr Ser Asp Gly Ser Thr Tyr Gln Val Cys Thr Asp Thr Arg Thr Asn
                130                 135                 140

Glu Pro Ser Ile Thr Gly Thr Ser Thr Phe Thr Gln Tyr Phe Ser Val
145                 150                 155                 160

Arg Glu Ser Thr Arg Thr Ser Gly Thr Val Thr Val Ala Asn His Phe
                165                 170                 175

Asn Phe Trp Ala His His Gly Phe Gly Asn Ser Asp Phe Asn Tyr Gln
                180                 185                 190

Val Val Ala Val Glu Ala Trp Ser Gly Ala Gly Ser Ala Ser Val Thr
                195                 200                 205

Ile Ser Ser
        210

<210> SEQ ID NO 34
<211> LENGTH: 354
<212> TYPE: PRT
<213> ORGANISM: Bacillus sp. 41M-1

<400> SEQUENCE: 34

Met Lys Gln Val Lys Ile Met Phe Leu Met Thr Met Phe Leu Gly Ile
1               5                  10                  15

Gly Leu Leu Phe Phe Ser Glu Asn Ala Glu Ala Ile Thr Ser Asn
                20                  25                  30

Glu Ile Gly Thr His Asp Gly Tyr Asp Tyr Glu Phe Trp Lys Asp Ser
            35                  40                  45

Gly Gly Ser Gly Ser Met Thr Leu Asn Ser Gly Thr Phe Ser Ala
        50                  55                  60

Gln Trp Ser Asn Val Asn Asn Ile Leu Phe Arg Lys Gly Lys Lys Phe
65                  70                  75                  80

Asp Glu Thr Gln Thr His Gln Gln Ile Gly Asn Met Ser Ile Asn Tyr
                85                  90                  95

Gly Ala Thr Tyr Asn Pro Asn Gly Asn Ser Tyr Leu Thr Val Tyr Gly
                100                 105                 110

Trp Thr Val Asp Pro Leu Val Glu Phe Tyr Ile Val Asp Ser Trp Gly
                115                 120                 125

Thr Trp Arg Pro Pro Gly Gly Thr Pro Lys Gly Thr Ile Asn Val Asp
            130                 135                 140

Gly Gly Thr Tyr Gln Ile Tyr Glu Thr Thr Arg Tyr Asn Gln Pro Ser
145                 150                 155                 160

Ile Lys Gly Thr Ala Thr Phe Gln Gln Tyr Trp Ser Val Arg Thr Ser
                165                 170                 175

Lys Arg Thr Ser Gly Thr Ile Ser Val Ser Glu His Phe Arg Ala Trp
                180                 185                 190

Glu Ser Leu Gly Met Asn Met Gly Asn Met Tyr Glu Val Ala Leu Thr
                195                 200                 205

Val Glu Gly Tyr Gln Ser Ser Gly Ser Ala Asn Val Tyr Ser Asn Thr
                210                 215                 220
```

```
Leu Thr Ile Gly Gly Gln Ser Gly Gly Glu Gln Ala Thr Arg Val Glu
225             230                 235                 240

Ala Glu Ser Met Thr Lys Gly Gly Pro Tyr Thr Ser Asn Ile Thr Ser
            245                 250                 255

Pro Phe Asn Gly Val Ala Leu Tyr Ala Asn Gly Asp Asn Val Ser Phe
            260             265                 270

Asn His Ser Phe Thr Lys Ala Asn Ser Ser Phe Ser Leu Arg Gly Ala
        275             280                 285

Ser Asn Asn Ser Asn Met Ala Arg Val Asp Leu Arg Ile Gly Gly Gln
    290             295                 300

Asn Arg Gly Thr Phe Tyr Phe Gly Asp Gln Tyr Pro Ala Val Tyr Thr
305             310                 315                 320

Ile Asn Asn Ile Asn His Gly Ile Gly Asn Gln Leu Val Glu Leu Ile
            325                 330                 335

Val Thr Ala Asp Asp Gly Thr Trp Asp Ala Tyr Leu Asp Tyr Leu Glu
            340                 345                 350

Ile Arg
```

THERMOSTABLE ALKALIPHILIC XYLANASE

This application is a continuing application of U.S. Ser. No. 60/133,714, filed May 12, 1999 and U.S. Ser. No. 60/138,156, filed Jun. 7, 1999.

FIELD OF THE INVENTION

The invention relates to xylanase activity (XA) proteins and nucleic acids. The invention further relates to the use of the XA proteins in the bleaching process of pulp and in the food and animal feed industry.

BACKGROUND OF THE INVENTION

Glycosyl hydrolase enzymes have been classified into more than 60 families that include xylanases (Xyn), cellulases, mannanases, amylases, beta-glucanases, and other carbohydrases [Henrissat, Biochem. J. 280:309–316 (1991); Henrissat and Bairoch, Biochem. J. 293:781–788 (1993); Henrissat and Bairoch, Biochem. J. 316:695–696 (1996); Davies and Henrissat, Structure 3:853–859 (1995); Coutinho and Henrissat, in Genetics, Biochemistry and Ecology of Cellulose Degradation, eds. Ohmiya et al., Uni Publishers Co., Tokyo, pp 15–23 (1999)]. These enzymes are classified based on amino acid sequence, the three dimensional structure and the geometry of the catalytic site [Gilkes et al., Microbiol. Reviews 55:303–315 (1991)]. Xylanases are produced by many organisms of bacterial and fungal origin (*Enzymes for Pulp and Paper Processing*, eds. Jeffries and Viikari; ACS Symposium Series Vol.655, American Chemical Society, Washington, D.C. (1996); and Xylans and Xylanases, eds. Visser et al., Progress in Biotechnology Vol. 7; Amsterdam-London-New York-Tokyo (1992)] and are used to hydrolyze the polysaccharide xylan, which is a major component of the plant cell walls [*Hemicellulose and Hemicellulases*, eds. Coughlan & Hazelwood; Portland Press Ltd, London-Chapel Hill, (1993)].

The endo-beta-1,4-xylanases (EC 3.2.1.8) belong either to the family 10 xylanases, formerly known as F, or to the family 11 xylanases, also known as G. The family 10 have an $(\alpha/\beta)_8$ barrel fold [Dominguez et al., Nat. Struc. Biol. 2:29–35 (1995)], whereas the family 11 xylanases are mostly β-sheet and the overall structure resembles that of a right hand [Torronen et al., EMBO J. 13:2493–2501 (1994)]. The *Bacillus circulans* xylanase belongs to the family 11.

Family 11 xylanases have been reported from varies microorganism (bacteria, yeast and fungi), including *Aspergillus awamori* var. *kawachi* xyn A [Ito, Swiss prot. Entry P48824]; *Aspergillus niger* Xyn A [Krengel and Dijkstra, J. Mol. Biol. 263(1):70–78 (1996); PDB entry 1 ukr]; *Aspergillus kawachii* Xyn C [Ito et al., Biosci. Biotechnol. Biochem. 56(8):1338–1340 (1992)]; *Aspergillus tubigensis* Xyn A [de Graaff et al., Mol. Microbiol. 12(3): 479–490 (1994)]; *Bacillus circulans* Xyn A [Yang et al., Nucl. Acids. Res., 16:7187 (1988)]; *Bacillus pumilus* Xyn A [Fukusaki et al., FEBS Lett. 171:197–201 (1984); *Bacillus subtilis* Xyn A [Paice et al., Arch, Microbiol. 144:201–202 (1986)]; Bacillus sp. strain 41M-1 [Ryuichiro et al., Nucl. Acids Symp. Series 31:235–236 (1994)]; *Cellulomonas fimi* Xyn D; Chainia spp. Xyn; *Clostridium acetobutylicum* Xyn B [Zappe et al., Nucl. Acids Res. 18(8):2179 (1990); *Clostridium stercorarium*; Xyn A [Sakka et al., Biosci. Biotechnol. Biochem. 57(2):273–277 (1993)]; *Cochliobolus carbonum* [Apel et al., Mol. Plant Microbe Interact. 6(4): 467–473 (1993)]; *Fibrobacter succinogenes* Xyn C [Paradis et al., J. Bacteriol. 175(23):7666–7672 (1993)]; *Neocallimastix patriciarum* Xyn A [Gilbert et al., Mol. Microbiol. 6(15):2065–2072 (1992)]; *Nocardiopsis dassonvillei* Xyn II; *Paecilomyces varotii* [J. Mol. Biol. 243(4):806–808 (1994); PDB entry 1 PVX]; *Ruminococcus flavefaciens* Xyn A Zhang and Flint, Mol. Microbiol. 6(8):1013–1023 (1992)]; *Schizophyllum commune* Xyn [Yaguchi et al., in Xylans and Xylanases, eds. Visser et al., Progress in Biotechnology Vol. 7; pp 149–154, Amsterdam-London-New York-Tokyo (1992); *Streptomyces lividans* Xyn B [Shareck et al., Gene 107(1):75–82 (1991)]; *Streptomyces lividans* Xyn C [Shareck et al., Gene 107(1):75–82 (1991)]; Streptomyces sp. No. 36a Xyn [Nagashima et al., Trends Actinomycetoligia 91–96 (1989)]; *Streptomyces thermoviolaceus* Xyn II; *Thermomonospora fusca* Xyn A; *Thermomyces lanuginosus* [Gruber et al., Biochemistry 37(39):13475–13485 (1998)]; *Trichoderma harzianum* Xyn [Campbell et al., PDB entry 1XND]; *Trichoderma reesei* Xyn I [Torronen and Rouvinen, Biochemistry 34:847 (1995); PDB entry 1XYN]; *Trichoderma reesei* Xyn II [Torronen et al., EMBO J. 13(11): 2493–2501 (1994); PDB entry 1 ENX]; *Trichoderma viride* Xyn [Yaguchi, GenBank accession #A44594; (gi:627019)].

In recent years, xylanases have become more and more used in the pulp and paper industry in a process called kraft pulp bleaching [*Enzymes for Pulp and Paper Processing*, eds. Jeffries and Viikari; ACS Symposium Series Vol. 655, American Chemical Society, Washington, D.C. (1996)]. These enzymes are added to the pulp before the pulp is bleached, to enhance the bleaching process and to remove a portion of the xylan in the pulp [Paice and Jurasek, J. Wood Chem. Tech. 4(2):187–198 (1984)]. This enzymatic pretreatment allows the subsequent bleaching chemicals, including chlorine, chlorine dioxide, hydrogen peroxide, oxygen, ozone, and sodium hydroxide, to bleach the pulp more efficiently than in the absence of xylanase treatment. The enhanced efficiency of bleaching has allowed mills to reduce the amount of chlorine-based chemicals used, thereby decreasing the amount of toxic by-products, which are environmental pollutants. In addition, less bleaching chemicals are used, lowering the chemical costs.

The Family 11 xylanases have several advantages over other xylanases in pulp bleaching applications. Most of the Family 11 xylanases are smaller than xylanases in other families. The small size relative to other xylanases is probably beneficial in penetrating the pulp fibers to release xylan from the pulp and enhance the bleaching. The Family 11 xylanases are also "pure" xylanases in terms of their catalytic activity. Unlike the xylanase enzymes in other families, these enzymes hydrolyze only xylan and do not hydrolyze cellulose. Cellulose hydrolysis damages the pulp and is unacceptable in a commercial mill.

In spite of the advantages of Family 11 xylanases in pulp bleaching, these enzymes have significant drawbacks. The range of temperature and pH that the enzymes exhibits activity on pulp are 45° C. to 55° C. and pH 5.0 to 7.5. A small proportion of mills have operated historically within these ranges. However, the step in the process where xylanase is applied is after a hot alkali treatment, so that the pulp is very basic and hot, typically having a temperature of 60° C. to 70° C. and a pH of 10 to 12. Both of these conditions are sub-optimal for xylanase enzymatic activity. For example, the *Bacillus circulans* wild type xylanase has a temperature optimum of 55° C. and a pH optimum of 5.5. In some mills the adjustment of temperature and pH are acceptable and routine, albeit energy intensive and costly. In many mills achieving the desired treatment conditions causes severe problems. Therefore, the intrinsic properties of the enzyme, such as thermostability and activity at elevated pH are critical parameters for their use in the bio-bleaching processes.

Among naturally occurring xylanases, thermostable enzymes have been isolated from thermophilic microbes, such as *Caldocellum saccharolyticum, Thermatoga maritima* and Thermatoga sp. strain FjSS3-B.1, all of which grow at 80° C. to 100° C. [(Luthi et al. Appl. Environ. Microbiol. 56:2677–2683 (1990); Winterhalter and Liebl, Appl. Environ. Microbiol. 61:1810–1815 (1995); Simpson et al., Biochem. J. 277:413–417 (1991)]. However, all are relatively large in size with high molecular mass of 35–120 kDa (320–1100 residues) and as such, their penetration into the pulp fibers might be limited. Some of these xylanases (e.g., *C. saccharolyticum* xylanase A) belong to families other than Family 11, and have both xylanase and cellulase activities (Luthi, et al., supra). Such cellulase activity is undesirable for pulp bleaching. Furthermore, hyperthermostable xylanases which function normally at extremely high temperatures have low activity at the comparatively lower temperatures for pulp bleaching.

It is well known in the art that xylanase also has uses in non-pulp applications. For example, xylanases have been reported to be useful in clarifying juice and wine [Zeikus et al., ACS Symp. Ser. 460:36–51 (1991); Beily, ACS Symp. Ser. 460:408–416 (1991); Woodward, Top Enzyme Ferment. Biotechnol. 8:9–30 (1984)]; extracting coffee, plant oils and starch [Beily, supra; Woodward supra; McCleary, Int. J. Biol. Macromol. 8:349–354 (1986)]; for the production of food thickeners (Zeikus et al., supra); altering texture in bakery products, e.g., improving the quality of dough, help bread rise and processing of wheat and corn for starch production (Maat et al. In *Xylans and xylanases*, eds. Visseret al., Elsevier Sci pub., Amsterdam. ISBN 0-444-894-772 (1992); McCleary, supra; Krishnarau et al., J. Food Sci. 59:1251–1254 (1994); U.S. Pat. No. 5,306,633); for use as animal food additives to aid in the digestibility of feedstuffs; and in the washing of super precision devices and semiconductors [Takayuki et al., U.S. Pat. No. 5,078,802). Several of these application could benefit from a thermostable xylanase, for example, food processing at elevated temperatures.

The active site of the *Bacillus circulans* xylanase is a wide cleft with two catalytic glutamates, E78 and E172, on either side and several aromatic tryptophan and tyrosine residues which act as binding sites for the substrate. The enzymatic mechanism consists of a nucleophilic attack of E78 on the 1,4-glycoside bond that is followed by a proton transfer from the acid/base catalyst E172 and a subsequent attack of a solvent water molecule where E172 now acts as a base. The enzymatic reaction results in retention of the configuration at the anomeric carbon [McCarter and Withers, Curr. Opin. Struc. Biol. 4:885–892 (1994)].

To this end, variants of xylanase (Xyn) sequences, applications and production procedures are known; see for example U.S. Pat. Nos.5,405,769; 5,736,384; 5,759,840; Arase et al. [FEB Lett. 316(2):123–7 (1993)]; Wakarchuket al.[Protein Sci. 3(3):467–75 (1994); Protein Eng. 7(11): 1379–86 (1994)]; and references cited therein.

Recently, the crystal structures of recombinant *Bacillus circulans* xylanase [PDB entry 1XNB; Campbell et al., in Suominen and Geinikainen , eds. Proceedings of the second *TRICEL symposium on Trichdema reesei cellulases and other hydrolases*, Espoo, Finland, Helsinki: Foundation for Biotechnological and Industrial Fermentation Research, pp 63–77 (1993)1; expressly incorporated by reference) have been solved. In addition, structures for xylanases from *Aspergillus niger* Xyn A[Krengel and Dijkstra, J. Mol. Biol. 263(1):70–78 (1996); PDB entry 1ukr]; *Paecilomyces varotii* [J. Mo Biol. 243(4):806–808 (1994); PDB entry 1 PVX]; *Trichoderma harzianum* [Campbell et al., PDB entry 1XND]; *Trichoderma reesei* [Torronene and Rouvinen, Biochemistry 34:847 (1995); PDB entry 1XYN]; *Trichoderma reesei* [Torronene et al., EMBO J. 13(11):2493–2501 (1994); PDB entry 1ENX], all of which are expressly incorporated by reference. The three-dimensional structure of *Bacillus circulans* xylenase is composed of three beta-sheets and one alpha-helix. The first two beta-sheets (I and II) are roughly parallel, while the third one (sheet III) is at about a 90 degree angle to sheet II. Sheets I and II are each composed of five strands, while sheet III contains six strands. The alpha-helix lies across the back of sheet III and the last two strands of sheet III fold over one edge of the alpha-helix. The active site lies in the cleft between sheets II and III (PDB entry 1XNB; U.S. Pat. No. 5,405,769, herewith expressly incorporated as reference).

When carrying out protein engineering to modify protein properties, usually one had to select from the following options: (i) site-specific mutagenesis and (ii) random mutagenesis of the nucleic acid encoding the protein, or (iii) post-translational chemical modifications. No matter which method of protein engineering is used, a key aspect is determining which amino acids to modify, because few choices will improve the properties of the protein. The available crystal structure of xylanase allows a completely different approach by using computational protein design and the generation of more stable proteins or protein variants with an altered activity. Several groups have applied and experimentally tested systematic, quantitative methods to protein design with the goal of developing general design algorithms (Hellinga et al., J. Mol. Biol. 222: 763–785 (1991); Hurley et al., J. Mol. Biol. 224:1143–1154 (1992); Desjarlaisl et al., Protein Science 4:2006–2018 (1995); Harbury et al., Proc. Natl. Acad. Sci. U.S.A. 92:8408–8412 (1995); Klemba et al., Nat. Struc. Biol. 2:368–373 (1995); Nautiyal etal., Biochemistry 34:11645–11651 (1995); Betzo etal., Biochemistry 35:6955–6962 (1996); Dahiyat et al., Protein Science 5:895–903 (1996); Dahiyat et al., Science 278:82–87 (1997); Dahiyat et. al., J. Mol. Biol. 273:789–96; Dahiyat et al., Protein Sci. 6:1333–1337 (1997); Jones, Protein Science 3:567–574 (1994); Konoi, et al., Proteins: Structure, Function and Genetics 19:244–255 (1994)). These algorithms consider the spatial positioning and steric complementarity of side chains by explicitly modeling the atoms of sequences under consideration. In particular, WO98/47089, and U.S. Ser. No. 09/127,926 describe a system for protein design; both are expressly incorporated by reference.

A need still exists for xylanase enzymes exhibiting both significant thermostability, thermophilicity, alkalophilicity and xylanase activity. It is therefore an object of this invention, to provide novel xylanase activity (XA) proteins that are active at higher pH and temperature ranges as the naturally occurring xylanases. The novel XA proteins may find wider application in the pre-treatment of kraft pulp and other applications.

SUMMARY OF THE INVENTION

In accordance with the objects outlined above, the present invention provides non-naturally occurring xylanase activity (XA) proteins (e.g. the proteins are not found in nature) comprising amino acid sequences that are less than about 97% identical to *Bacillus circulans* xylanase. The XA proteins have at least one altered biological property when compared to *Bacillus circulans* xylanase; for example, the XA proteins will be more alkalophilic or more thermophilic or more thermostable or hydrolyze a substrate more efficiently than *Bacillus circulans* xylanase. Thus, the invention provides XA proteins with amino acid sequences that have at least about 3–5 amino acid substitutions as compared to the *Bacillus circulans* xylanase sequence shown in FIG. 1 (SEQ ID NO:1).

In a further aspect, the present invention provides non-naturally occurring XA conformers that have three dimensional backbone structures that substantially correspond to the three dimensional backbone structure of *Bacillus circulans* xylanase. The amino acid sequence of the XA conformer and the amino acid sequence of *Bacillus circulans* xylanase are less than about 97% identical. In one aspect, at least about 90% of the non-identical amino acids are in a core region of the conformer. In other aspects, the conformer have at least about 100% of the non-identical amino acids are in a core region of the conformer.

In an additional aspect, the changes are selected from the amino acid residues at positions selected from positions 7, 26, 28, 30, 39, 53, 58, 63, 64, 65, 67, 79, 80, 83, 84, 85, 88, 96, 98, 100, 102, 103, 105, 109, 110, 118, 128, 129, 130, 132, 136, 142, 144, 147, 148, 149, 150, 152, 156, 158, 160, 167, 168, 171, 176, 180, and 182. In a preferred aspect, the changes are selected from the amino acid residues at positions selected from positions 26, 28, 30, 53, 58, 64, 79, 105, 142, 171, 176, 180, and 182. In one aspect, the changes are selected from the amino acid residues at positions selected from positions 53, 83, 84, 85 105, 132, 136, 142, 144, and 149. In another aspect, the changes are selected from the amino acid residues at positions selected from positions 79, 96, 98, 100, 102, 103, 105, 109, 128, 130, 132, 144, 147, 148, 149, 150, 152, 156, 158, 160, and 167. In another aspect, the changes are selected from the amino acid residues at positions selected from positions 7, 39, 63, 65, 67, 88, 110, 118, 129, and 168. Preferred embodiments include at least about 3–5 variations.

In a further aspect, the invention provides recombinant nucleic acids encoding the non-naturally occurring XA proteins, expression vectors comprising the recombinant nucleic acids, and host cells comprising the recombinant nucleic acids and expression vectors.

In an additional aspect, the invention provides methods of producing the XA proteins of the invention comprising culturing host cells comprising the recombinant nucleic acids under conditions suitable for expression of the nucleic acids. The proteins may optionally be recovered.

In a further aspect, the invention provides a bleaching agent comprising as an active ingredient an XA protein.

In an additional aspect of the invention, the invention provides a method for bleaching pulp, said method comprising the step of contacting pulp to be bleached with the bleaching agent. The method may further comprise the step of chemical bleaching and/or an alkali extraction before, after or during said step of contacting pulp with said bleaching agent.

BRIEF DESCRIPTION OF THE DRAWINGS

FIG. 1A (SEQ ID NO:1) depicts the amino acid sequence of the endo-1,4-beta xylanase precursor (Xylanase; /1,4-beta-D-xylan xylanohydrolase; E.C. 3.2.1.8) as deposited under GenBank accession numbers P09850 and CAA30553 [see also Yang et al., Nucleic Acids Res. 16 (14B):7187 (1988)]. Amino acid residues 1–28 correspond to the signal peptide and amino acid residues 29–213 correspond to the mature protein.

FIG. 1B (SEQ ID NO:1) depicts the amino acid sequence of *Bacillus circulans* xylanase as used in the determination of the crystal structure [PDB and GerBank # 1XNB; Campbell et al., in Suominen and Geinikainen, eds. *Proceedings of the second TRICEL symposium on Trichderma reesei cellulases and other hydrolases*, Espoo, Finland, Helsinki: Foundation for Biotechnological and Industrial Fermentation Research, pp 63–77 (1993)] and secondary structure elements. Secondary structure element legend: H, alpha helix (4-helix); B, residue in isolated beta bridge; E, extended strand, participates in beta ladder; G, 310 helix (3-helix); I, pi helix (5-helix); T, hydrogen bonded turn; S, bend. Amino acid residues 1 to 185 correspond to amino acid residues 29–213 of the amino acid sequence of FIG. 1A (SEQ ID NO:1). The amino acid numbers shown were used as the amino acid numbers in the design of XA proteins.

FIG. 1C (SEQ ID NO:2) depicts the complete DNA sequence encoding wild type *Bacillus circulans*xylanase (Yang et al., Nucleic Acids Res. 16 (14B):7187 (1988); GenBank accession number X07723). The encoded sequence consists of the signaling sequence, MFKFKKN-FLVGLSAALMSISLFSATASA (positions −28 to −1 of SEQ ID NO:1), and the 185 amino acids that constitute the actual protein (see FIGS. 1A and 1B) (SEQ ID NO:1). The DNA sequence of 1349 nucleotides includes this coding sequence and non-translated 5' and 3' sequences. Bases 392 to 1033 encode wild type *Bacillus circulans* xylanase (213 amino acid residues).

FIG. 2A depicts the structure of wild type *Bacillus circulans* xylanase (PDB structure 1XNB). The side chains are drawn for those residues that are included in a PDA CORE design.

FIG. 2B depicts the structure of wild type *Bacillus circulans* xylanase (PDB structure 1XNB). The side chains are drawn for those residues that are included in a PDA design of the area around the buried polar residue D83.

FIG. 2C depicts the structure of wild type *Bacillus circulans* xylanase (PDB structure 1XNB.) The side chains are drawn for those residues that are included in a PDA design of the area around the helix.

FIG. 2D depicts the active site of *B. circulans* xylanase based on PDB entry 1XNB. Those positions included in the PDA design of the active site are shown by their side chain representation. In black are wild type residues, (their conformation was allowed to change, but not their amino acid identity). In grey are positions whose conformation and identity were allowed to change (to any amino acid except proline, cysteine and glycine).

FIG. 3 depicts the residues of the wild type *bacillus circulans* xylanase sequence that are selected for the indicated PDA designs as indicated: for the CORE region, the region around D83, the region around the helix, and the region around the active site. The individual sets are described in detail herein.

FIG. 4A depicts the mutation pattern of XA protein CORE sequences based on the analysis of the lowest 1000 protein sequences generated by Monte Carlo analysis of XA protein core sequences. The probability table shows only the amino acid residues of positions 26, 28, 30, 36, 38, 51, 53, 55, 58, 62, 64, 66, 68, 70, 72, 77, 79, 81, 105, 107, 130, 142, 144, 146, 153, 169, 171, 173, 176, 178, 180, 182, and 184. The presence of each amino acid residue at a given position is indicated as %. For example, at position 26, the *Bacillus circulans* xylanase amino acid is tyrosine (see FIG. 1) (SEQ ID NO:1); in XA proteins, >90% of the top 1000 sequences had phenylalanine at this position, and only <1% of the sequences had tyrosine.

FIG. 4B (SEQ ID NO:3) depicts a preferred XA protein sequence based on the PDA analysis of Example 2. Amino acid residues different from the *Bacillus circulans* xylanase (see FIG. 1) (SEQ ID NO:1) are shown in bold and are underlined.

FIG. 5A depicts the mutation pattern of XA protein sequences analyzed at the 'Region around D83'. The analysis is based on the calculation parameters described in Example 3(a) and on the analysis of the lowest 1000 protein sequences generated by Monte Carlo analysis of XA protein 'Region around D83' sequences. The probability table shows only the amino acid residues of positions 53, 66, 67, 68, 81, 82, 83, 84, 85, 101, 105, 132, 136, 138, 142, 144, 149, and 169. The occurrence of each amino acid residue at a given position is indicated as %. For example, at position 53, the *Bacillus circulans* xylanase amino acid is tyrosine (see FIG. 1) (SEQ ID NO:1); in XA proteins, all of the top 1000 sequences had phenylalanine at this position.

FIG. 5B (SEQ ID NO:4) depicts a preferred XA protein sequence based on the PDA analysis of Example 3(a). Amino acid residues different from the *Bacillus circulans* xylanase (see FIG. 1) (SEQ ID NO:1) are shown in bold and are underlined.

FIG. 6A depicts the mutation pattern of XA protein sequences analyzed at the 'Region around D83'. This analysis is based on the calculation parameters described in Example 3(b) and on the analysis of the lowest 1000 protein sequences generated by Monte Carlo analysis of XA protein 'Region around D83' sequences. See legend of FIG. 5A for further details.

FIG. 6B (SEQ ID NO:4) depicts a preferred XA protein sequence based on the PDA analysis of Example 3(b). Amino acid residues different from the *Bacillus circulans* xylanase (see FIG. 1) (SEQ ID NO:1) are shown in bold and are underlined.

FIG. 7A depicts the mutation pattern of XA protein sequences analyzed at the 'Region around D83'. The analysis is based on the calculation parameters described in Example 3(c), and on the analysis of the lowest 1000 protein sequences generated by Monte Carlo analysis of XA protein 'Region around D83' sequences. The probability table shows only the amino acid residues of positions 53, 66, 68, 81, 83, 84, 101, 105, 132, 136, 138, 142, 144, 149, and 169. The occurrence of each amino acid residue at a given position is indicated as %. For example, at position 136, the *Bacillus circulans* xylanase amino acid is arginine (see FIG. 1) (SEQ ID NO:1); in XA proteins, of the top 1000 sequences >90% had methionine at this position and some XA proteins had lysine, leucine, glutamic acid and phenylalanine. None of the XA proteins had arginine at this posibon.

FIG. 7B (SEQ ID NO:5) depicts a preferred XA protein sequence based on the PDA analysis of Example 3(c). Amino acid residues different from the *Bacillus circulans* xylanase (see FIG. 1) (SEQ ID NO:1) are shown in bold and are underlined.

FIG. 8A depicts the mutation pattern of XA protein sequences analyzed at the 'Region around D83'. This analysis is based on the calculation parameters described in Example 3(d) and on the analysis of the lowest 1000 protein sequences generated by Monte Carlo analysis of XA protein 'Region around D83' sequences. See legend of FIG. 7A for further details.

FIG. 8B (SEQ ID NO:5) depicts a preferred XA protein sequence based on the PDA analysis of Example 3(d). Amino acid residues different from the *Bacillus circulans* xylanase (see FIG. 1) (SEQ ID NO:1) are shown in bold and are underlined.

FIG. 9A depicts the mutation pattern of XA protein sequences analyzed at the 'Region around D83'. This analysis is based on the calculation parameters described in Example 3(e) and on the analysis of the lowest 1000 protein sequences generated by Monte Carlo analysis of XA protein 'Region around D83' sequences. See legend of FIG. 5A for further details.

FIG. 9B (SEQ ID NO:6) depicts a preferred XA protein sequence based on the PDA analysis of Example 3(e). Amino acid residues different from the *Bacillus circulans* xylanase (see FIG. 1) (SEQ ID NO:1) are shown in bold and are underlined.

FIG. 10A depicts the mutation pattern of XA protein sequences analyzed at the 'Region around D83'. This analysis is based on the calculation parameters described in Example 3(f) and on the analysis of the lowest 1000 protein sequences generated by Monte Carlo analysis of XA protein 'Region around D83' sequences. See legend of FIG. 5A for further details.

FIG. 10B (SEQ ID NO:7) depicts a preferred XA protein sequence based on the PDA analysis of Example 3(f). Amino acid residues different from the *Bacillus circulans* xylanase (see FIG. 1) (SEQ ID NO:1) are shown in bold and are underlined.

FIG. 11A depicts the mutation pattern of XA protein sequences analyzed at the 'Helix Region'. The analysis is based on the calculation parameters described in Example 4(a) and on the analysis of the lowest 1000 protein sequences generated by Monte Carlo analysis of XA protein 'Helix Region' sequences. The probability table shows only the amino acid residues of positions 70, 72, 77, 79, 81, 95, 96, 98, 100, 101, 102, 103, 105, 107, 109, 128, 130, 132, 144, 146, 147, 148, 149, 150, 152, 153, 156, 157, 158, 160, 161, 164, and 167. The occurrence of each amino acid residue at a given position is indicated as %. For example, at position 79, the *Bacillus circulans* xylanase amino acid is tyrosine (see FIG. 1) (SEQ ID NO:1); in XA proteins, all of the top 1000 sequences had phenylalanine at this position.

FIG. 11B (SEQ ID NO:8) depicts a preferred XA protein sequence based on the PDA analysis of Example 4(a). Amino acid residues different from the *Bacillus circulans* xylanase (see FIG. 1) (SEQ ID NO:1) are shown in bold and are underlined.

FIG. 12A depicts the mutation pattern of XA protein sequences analyzed at the 'Helix Region'. This analysis is based on the calculation parameters described in Example 4(b) and on the analysis of the lowest 1000 protein sequences generated by Monte Carlo analysis of XA protein 'Helix Region' sequences. Asterisks indicate wild type residues that are included in the PDA calculation but cannot change their identity. See legend of FIG. 11A for further details.

FIG. 12B (SEQ ID NO:9) depicts a preferred XA protein sequence based on the PDA analysis of Example 4(b). Amino acid residues different from the *Bacillus circulans* xylanase (see FIG. 1) (SEQ ID NO:1) are shown in bold and are underlined.

FIG. 13A depicts the mutation pattern of XA protein sequences analyzed at the 'Helix Region'. This analysis is based on the calculation parameters described in Example 4(c) and on the analysis of the lowest 1000 protein sequences generated by Monte Carlo analysis of XA protein 'Helix Region' sequences. See legend of FIG. 10A for further details.

FIG. 13B (SEQ ID NO: 10) depicts a preferred XA protein sequence based on the PDA analysis of Example 4(c). Amino acid residues different from the *Bacillus circulans* xylanase (see FIG. 1) (SEQ ID NO:1) are shown in bold and are underlined.

FIG. 14A depicts the mutation pattern of XA protein sequences analyzed at the 'Active Site Region'. The analysis is based on the calculation parameters described in Example 5(a) and on the analysis of the lowest 10,000 protein sequences generated by Monte Carlo analysis of XA protein 'Active Site Region' sequences. The probability table shows only the amino acid residues of positions 5, 7, 11, 37, 39, 63, 65, 67, 71, 80, 82, 88, 110, 115, 118, 125, 129, 168, and 170. The occurrence of each amino acid residue at a given position is indicated as %. Only those amino acids with a probability greater than 1% are shown. For example, at position 110, the *Bacillus circulans* xylanase amino acid is threonine (see FIG. 1) (SEQ ID NO:1); in XA proteins, within the top 1000 sequences aspartic acid is the preferred amino acid at this position (99.9%).

FIG. 14B (SEQ ID NO:11) depicts a preferred XA protein sequence based on the PDA analysis of Example 5(a). Amino acid residues different from the *Bacillus circulans* xylanase (see FIG. 1) (SEQ ID NO:1) are shown in bold and are underlined.

FIG. 15A depicts the mutation pattern of XA protein sequences analyzed at the 'Active Site Region with Substrate'. This analysis is based on the calculation parameters described in Example 5(b) and on the analysis of the lowest 10,000 protein sequences generated by Monte Carlo analysis of XA protein 'Active Site Region with Substrate' sequences. See legend of FIG. 14A for further details.

FIG. 15B (SEQ ID NO:12) depicts a preferred XA protein sequence based on the PDA analysis of Example 5(b). Amino acid residues different from the *Bacillus circulans* xylanase (see FIG. 1) (SEQ ID NO:1) are shown in bold and are underlined.

FIG. 16A (SEQ ID NO:13) depicts the amino acid sequence of *Bacillus subtilis* xylanase.

FIG. 16B (SEQ ID NO:14) depicts the amino acid sequence of *Bacillus pumilus* xylanase.

FIG. 16C (SEQ ID NO:15) depicts the amino acid sequence of *Streptomyces lividans* xylanase B.

FIG. 16D (SEQ ID NO:16) depicts the amino acid sequence of *Streptomyces lividans* xylanase C.

FIG. 16E (SEQ ID NO:17) depicts the amino acid sequence of *Clostridium acetobutyliticum* xylanase.

FIG. 16F (SEQ ID NO:18) depicts the amino acid sequence of *Schizophyllum commune* xylanase.

FIG. 16G (SEQ ID NO:19) depicts the amino acid sequence of *Trichoderma viride* xylanase.

FIG. 16H (SEQ ID NO:20) depicts the amino acid sequence of *Trichoderma harzianum* xylanase.

FIG. 16I (SEQ ID NO:21) depicts the amino acid sequence of *Trichoderma reesei* xyn I xylanase.

FIG. 16J (SEQ ID NO:22) depicts the amino acid sequence of *Trichoderma reesei* xyn II xylanase.

FIG. 16K (SEQ ID NO:23) depicts the amino acid sequence of *Paecilomyces variotii* xylanase.

FIG. 16L (SEQ ID NO:24) depicts the amino acid sequence of *Thermomyces lanuginosus* xylanase.

FIG. 16M (SEQ ID NO:25) depicts the amino acid sequence of *Aspergillus niger* xylanase.

FIG. 16N (SEQ ID NO:26) depicts the amino acid sequence of *Aspergillus awamori* var. *kawachi*xylanase A.

FIG. 16O (SEQ ID NO:27) depicts the amino acid sequence of *Aspergillus awamori* var. *kawachi* xylanase FIG. 16P (SEQ ID NO:28) depicts the amino acid sequence of *Neocahlimaslix patriciarum* xylanase.

FIG. 16Q (SEQ ID NO:29) depicts the amino acid sequence of *Cochijobolus carbonum* xylanase.

FIG. 16R (SEQ ID NO:30) depicts the amino acid sequence of *Clostridium stercorarium* xylanase.

FIG. 16S (SEQ ID NO:31) depicts the amino acid sequence of *Ruminococcus flavefaciens* xylanase.

FIG. 16T (SEQ ID NO:32) depicts the amino acid sequence of *Fibrobacter succinogenes* xylanase.

FIG. 16U (SEQ ID NO:33) depicts the amino acid sequence of *Aspergillus tubigensis* xylanase.

FIG. 16V (SEQ ID NO:34) depicts the amino acid sequence of Bacillus sp. strain 41M-1 xylanase.

FIG. 17 depicts the synthesis of a full-length gene and all possible mutations by PCR. Overlapping oligonucleotides corresponding to the full-length gene (black bar, Step 1) and comprising one or more desired mutations are synthesized, heated and annealed. Addition of DNA polymerase to the annealed oligonucleotides results in the 5' to 3' synthesis of DNA (Step 2) to produce longer DNA fragments (Step 3). Repeated cycles of heating, annealing, and DNA synthesis (Step 4) result in the production of longer DNA, including some full-length molecules. These can be selected by a second round of PCR using primers (indicated by arrows) corresponding to the end of the full-length gene (Step 5).

FIG. 18 depicts a preferred scheme for synthesizing a XA protein library of the invention. The wild type gene, or any starting gene, such as the gene for the global minima gene, can be used. Oligonucleotides comprising sequences that encode different amino acids at the different variant positions (indicated in the Figure by box 1, box 2, and box 3) can be used during PCR. Those primers can be used in combination with standard primers. This generally requires fewer oligonucleotides and can result in fewer errors.

FIGS. 19A and 19B depict an overlapping extension method. At the top of FIG. 19A is the template DNA showing the locations of the regions to be mutated (black boxes) and the binding sites of the relevant primers (arrows). The primers R1 and R2 represent a pool of primers, each containing a different mutation; as described herein, this may be done using different ratios of primers if desired. The variant position is flanked by regions of homology sufficient to get hybridization. Thus, as shown in this example, oligos R1 and F2 comprise a region of homology and so do oligos R2 and F3. In this example, three separate PCR reactions are done for step 1. The first reaction contains the template plus oligos F1 and R1. The second reaction contains template plus oligos F2 and R2, and the third contains the template and oligos F3 and R3. The reaction products are shown. In Step 2, the products from Step 1 tube 1 and Step 1 tube 2 are taken. After purification away from the primers, these are added to a fresh PCR reaction together with F1 and R4. During the denaturation phase of the PCR, the overlapping regions anneal and the second strand is synthesized. The product is then amplified by the outside primers, F1 and R4. In Step 3, the purified product from Step 2 is used in a third PCR reaction, together with the product of Step 1, tube 3 and the primers F1 and R3. The final product corresponds to the full length gene and contains the required mutations. Alternatively, Step 2 and Step 3 can be performed in one PCR reaction.

FIGS. 20A and 20B depict a ligation of PCR reaction products to synthesize the libraries of the invention. In this technique, the primers also contain an endonuclease restriction site (RE), either generating blunt ends, 5' overhanging ends or 3' overhanging ends. We set up three separate PCR reactions for Step 1. The first reaction contains the template plus oligos F1 and R1. The second reaction contains template plus oligos F2 and R2, and the third contains the template and oligos F3 and R3. The reaction products are shown. In Step 2, the products of Step 1 are purified and then digested with the appropriate restriction endonuclease. The digestion products from Step 2, tube 1 and Step 2, tube 2 are ligated togther with DNA ligase (Step 3). The products are then amplified in Step 4 using oligos F1 and R4. The whole process is then repeated by digesting the amplified products, ligating them to the digested products of Step 2, tube 3, and then amplifying the final product using oligos F1 and R3. It would also be possible to ligate all three PCR products from Step 1 together in one reaction, providing the two restriction sites (RE1 and RE2) were different.

FIG. 21 depicts blunt end ligation of PCR products. In this technique, oligos such as F2 and R1 or R2 and F3 do not overlap, but they abut. Again three separate PCR reactions are performed. The products from tube 1 and tube 2 (see FIG. 20A, Step 1) are ligated, and then amplified with outside primers F1 and R4. This product is then ligated with the product from Step 1, tube 3. The final products are then amplified with primers F1 and R3.

DETAILED DESCRIPTION OF THE INVENTION

The present invention is directed to novel proteins and nucleic acids possessing xylanase activity (sometimes referred to herein as "XA proteins" and "XA nucleic acids"). The proteins are generated using a system previously described in WO98/47089 and U.S. Ser. Nos. 09/058,459, 09/127,926, 60/104,612, 60/158,700, 09/419,351, 60/181,630, 60/186,904, 60/132,475, 60/133,714, U.S. patent application, entitled Protein Design Automation For Protein Libraries (Filed: Apr. 14, 2000; Inventor: Bassil Dahiyat), and PCT US98/07254, all of which are expressly incorporated by reference in their entirety, that is a computational modeling system that allows the generation of extremely stable proteins without necessarily disturbing the biological functions of the protein itself. In this way, novel XA proteins and nucleic acids are generated, that can have a plurality of mutations in comparison to the wild-type enzyme yet retain significant activity.

Generally, there are a variety of computational methods that can be used to generate the XA proteins of the invention. In a preferred embodiment, sequence based methods are used. Alternatively, structure based methods, such as PDA, described in detail below, are used.

Similarly, molecular dynamics calculations can be used to computationally screen sequences by individually calculating mutant sequence scores and compiling a rank ordered list.

In a preferred embodiment, residue pair potentials can be used to score sequences (Miyazawa et al., Macromolecules 18(3):534–552 (1985), expressly incorporated by reference) during computational screening.

In a preferred embodiment, sequence profile scores (Bowie et al., Science 253(5016):164–70 (1991), incorporated by reference) and/or potentials of mean force (Hendlich et al., J. Mol. Biol. 216(1):167–180 (1990), also incorporated by reference) can also be calculated to score sequences. These methods assess the match between a sequence and a 3D protein structure and hence can act to screen for fidelity to the protein structure. By using different scoring functions to rank sequences, different regions of sequence space can be sampled in the computational screen.

Furthermore, scoring functions can be used to screen for sequences that would create metal or co-factor binding sites in the protein (Hellinga, Fold Des. 3(1):R1–8 (1998), hereby expressly incorporated by reference). Similarly, scoring functions can be used to screen for sequences that would create disulfide bonds in the protein. These potentials attempt to specifically modify a protein structure to introduce a new structural motif.

In a preferred embodiment, sequence and/or structural alignment programs can be used to generate the XA proteins of the invention. As is known in the art, there are a number of sequence-based alignment programs; including for example, Smith-Waterman searches, Needleman-Wunsch, Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and GeneWise.

As is known in the art, there are a number of sequence alignment methodologies that can be used.

For example, sequence homology based alignment methods can be used to create sequence alignments of proteins related to the target structure (Altschul et al., J. Mol. Biol. 215(3):403–410 (1990), Altschul et al., Nucleic Acids Res. 25:3389–3402 (1997), both incorporated by reference). These sequence alignments are then examined to determine the observed sequence variations. These sequence variations are tabulated to define a set of XA proteins.

Sequence based alignments can be used in a variety of ways. For example, a number of related proteins can be aligned, as is known in the art, and the "variable" and "conserved" residues defined; that is, the residues that vary or remain identical between the family members can be defined. These results can be used to generate a probability table, as outlined below. Similarly, these sequence variations can be tabulated and a secondary library defined from them as defined below. Alternatively, the allowed sequence variations can be used to define the amino acids considered at each position during the computational screening. Another variation is to bias the score for amino acids that occur in the sequence alignment, thereby increasing the likelihood that they are found during computational screening but still allowing consideration of other amino acids. This bias would result in a focused library of XA proteins but would not eliminate from consideration amino acids not found in the alignment. In addition, a number of other types of bias may be introduced. For example, diversity may be forced; that is, a "conserved" residue is chosen and altered to force diversity on the protein and thus sample a greater portion of the sequence space. Alternatively, the positions of high variability between family members (i.e. low conservation) can be randomized, either using all or a subset of amino acids. Similarly, outlier residues, either positional outliers or side chain outliers, may be eliminated.

Similarly, structural alignment of structurally related proteins can be done to generate sequence alignments (Orengo et al., Structure 5(8):1093–108 (1997); Holm et al., Nucleic Acids Res. 26(1):316–9 (1998), both of which are incorporated by reference). These sequence alignments can then be examined to determine the observed sequence variations. Libraries can be generated by predicting secondary structure from sequence, and then selecting sequences that are compatible with the predicted secondary structure. There are a number of secondary structure prediction methods such as helix-coil transition theory (Munoz and Serrano, Biopolymers 41:495, 1997), neural networks, local structure alignment and others (e.g., see in Selbig et al., Bioinformatics 15:1039–46, 1999).

Similarly, as outlined above, other computational methods are known, including, but not limited to, sequence profiling [Bowie and Eisenberg, Science 253(5016):164–70, (1991)], rotamer library selections [Dahiyat and Mayo, Protein Sci. 5(5):895–903 (1996); Dahiyat and Mayo, Science 278(5335):82–7 (1997); Desjarlais and Handel, Protein Science 4:2006–2018 (1995); Harbury et al Proc. Natl. Acad. Sci. U.S.A. 92(18):8408–8412 (1995); Kono et al., Proteins: Structure, Function and Genetics 19:244–255 (1994); Hellinga and Richards, Proc. Natl. Acad. Sci. U.S.A. 91:5803–5807 (1994)]; and residue pair potentials [Jones, Protein Science 3: 567–574, (1994)]; PROSA [Heindlich et al., J. Mol. Biol. 216:167–180 (1990)]; THREADER [Jones et al., Nature 358:86–89 (1992)], an inverse folding methods such as those described by Simons et al. [Proteins, 34:535–543, (1999)], Levitt and Gerstein [Proc. Natl. Acad. Sci. U.S.A., 95:5913–5920, (1998)], Godzik and Skolnick [Proc. Natl. Acad. Sci. U.S.A., 89:12098–102, (1992)], Godzik et al. [J. Mol. Biol. 227:227–38, (1992)] and two profile methods [Gribskov et al. Proc. Natl. Acad. Sci. U.S.A. 84:4355–4358 (1987) and Fischer and Eisenberg, Protein Sci. 5:947–955 (1996), Rice and Eisenberg J. Mol. Biol. 267:1026–1038(1997)], all of which are expressly incorporated by reference. In addition, other computational methods such as those described by Koehl and Levitt (J. Mol. Biol. 293:1161–1181 (1999); J. Mol. Biol. 293:1183–1193 (1999); expressly incorporated by reference) can be used to create a protein sequence library which can optionally then be used to generate a smaller secondary library for use in experimental screening for improved properties and function. In addition, there are computational methods based on forcefield calculations such as SCMF that can be used as well for SCMF, see Delarue et al. Pac. Symp. Biocomput. 109–21 (1997); Koehl et al., J. Mol. Biol. 239:249–75 (1994); Koehl et al., Nat. Struct. Biol. 2:163–70 (1995); Koehl et al., Curr. Opin. Struct. Biol. 6:222–6 (1996); Koehl et al., J. Mol. Biol. 293:1183–93 (1999); Koehl et al., J. Mol. Biol. 293:1161–81 (1999); Lee J., Mol. Biol. 236:918–39 (1994); and Vasquez Biopolymers 36:53–70 (1995); all of which are expressly incorporated by reference. Other forcefield calculations that can be used to optimize the conformation of a sequence within a computational method, or to generate de novo optimized sequences as outlined herein include, but are not limited to, OPLS-AA [Jorgensen et al., J. Am. Chem. Soc. 118:11225–11236 (1996); Jorgensen, W. L.; BOSS, Version 4.1; Yale University: New Haven, Conn. (1999)]; OPLS [Jorgensen et al., J. Am. Chem. Soc.110:1657ff (1988); Jorgensen et al., J Am. Chem. Soc.112:4768ff (1990)]; UNRES (United Residue Forcefield; Liwo et al., Protein Science 2:1697–1714 (1993); Liwo et al., Protein Science 2:1715–1731 (1993); Liwo et al., J. Comp. Chem. 18:849–873 (1997); Liwo et al., J. Comp. Chem. 18:874–884 (1997); Liwo et al., J. Comp. Chem. 19:259–276 (1998); Forcefield for Protein Structure Prediction (Liwo et al., Proc. Natl. Acad. Sci. U.S.A. 96:5482–5485 (1999)]; ECEPP/3 [Liwo et al., J Protein Chem. 13(4):375–80 (1994)]; AMBER 1.1 force field (Weiner et a Am. Chem. Soc. 106:765–784); AMBER 3.0 force field [U.C. Singh et al., Proc. Natl. Acad. Sci. U.S.A. 82:755–759 (1985)]; CHARMM and CHARMM22 (Brooks et al., J. Comp. Chem. 4:187–217); cvff3.0 [Dauber-Osguthorpe et al., Proteins: Structure, Function and Genetics, 4:3147 (1988)]; cff91 (Maple et al., J. Comp. Chem. 15:162–182); also, the DISCOVER (cvff and cff91) and AMBER forcefields are used in the INSIGHT molecular modeling package (Biosym/MSI, San Diego Calif.) and CHARMM is used in the QUANTA molecular modeling package (Biosym/MSI, San Diego Calif.), all of which are expressly incorporated by reference. In fact, as is outlined below, these forcefield methods may be used to generate the secondary library directly; that is, no primary library is generated; rather, these methods can be used to generate a probability table from which the secondary library is directly generated.

In a preferred embodiment, the computational method used to generate the primary library is Protein Design Automation (PDA), as is described in U.S. Ser. Nos. 60/061,097, 60/043,464, 60/054,678, 09/127,926, 60/104,612, 60/158,700, 09/419,351, 60/181630, 60/186,904, 60/132,475, 60/133,714, U.S. patent application, entitled Protein Design Automation For Protein Libraries (Filed: Apr. 14, 2000; Inventor: Bassil Dahiyat) and PCT US98/07254, all of which are expressly incorporated herein by reference. Briefly, PDA can be described as follows. A known protein structure is used as the starting point. The residues to be optimized are then identified, which may be the entire sequence or subset(s) thereof. The side chains of any positions to be varied are then removed. The resulting structure consisting of the protein backbone and the remaining sidechains is called the template. Each variable residue position is then preferably classified as a core residue, a surface residue, or a boundary residue; each classification defines a subset of possible amino acid residues for the position (for example, core residues generally will be selected from the set of hydrophobic residues, surface residues generally will be selected from the hydrophilic residues, and boundary residues may be either). Each amino acid can be represented by a discrete set of all allowed conformers of each side chain, called rotamers. Thus, to arrive at an optimal sequence for a backbone, all possible sequences of rotamers must be screened, where each backbone position can be occupied either by each amino acid in all its possible rotameric states, or a subset of amino acids, and thus a subset of rotamers.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include the energy of van der Waal's forces, the energy of hydrogen bonding, the energy of secondary structure propensity, the energy of surface area solvation and the electrostatics. Thus, the total energy of each rotamer interaction, both with the backbone and other rotamers, is calculated, and stored in a matrix form.

The discrete nature of rotamer sets allows a simple calculation of the number of rotamer sequences to be tested. A backbone of length n with m possible rotamers per position will have $m^n$ possible rotamer sequences, a number which grows exponentially with sequence length and renders the calculations either unwieldy or impossible in real time. Accordingly, to solve this combinatorial search problem, a "Dead End Elimination" (DEE) calculation is performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a Monte Carlo search may be done to generate a rank-ordered list of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated. Monte Carlo searching is a sampling technique to explore sequence space around the global minimum or to find new local minima distant in sequence space. As is more additionally outlined below, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example), etc.). Similarly, for all the sampling techniques, the acceptance criteria of whether a sampling jump is accepted can be altered.

As outlined in U.S. Ser. No. 09/127,926, the protein backbone (comprising (for a naturally occurring protein) the nitrogen, the carbonyl carbon, the α-carbon, and the carbonyl oxygen, along with the direction of the vector from the α-carbon to the β-carbon) may be altered prior to the computational analysis, by varying a set of parameters called supersecondary structure parameters.

Once a protein structure backbone is generated (with alterations, as outlined above) and input into the computer, explicit hydrogens are added if not included within the structure (for example, if the structure was generated by X-ray crystallography, hydrogens must be added). After hydrogen addition, energy minimization of the structure is run, to relax the hydrogens as well as the other atoms, bond angles and bond lengths. In a preferred embodiment, this is done by doing a number of steps of conjugate gradient minimization [Mayo et al., J. Phys. Chem. 94:8897 (1990)] of atomic coordinate positions to minimize the Dreiding force field with no electrostatics. Generally from about 10 to about 250 steps is preferred, with about 50 being most preferred.

The protein backbone structure contains at least one variable residue position. As is known in the art, the residues, or amino acids, of proteins are generally sequentially numbered starting with the N-terminus of the protein. Thus a protein having a methionine at it's N-terminus is said to have a methionine at residue or amino acid position 1, with the next residues as 2, 3, 4, etc. At each position, the wild type (i.e. naturally occurring) protein may have one of at least 20 amino acids, in any number of rotamers. By "variable residue position" herein is meant an amino acid position of the protein to be designed that is not fixed in the design method as a specific residue or rotamer, generally the wild-type residue or rotamer.

In a preferred embodiment, all of the residue positions of the protein are variable. That is, every amino acid side chain may be altered in the methods of the present invention. This is particularly desirable for smaller proteins, although the present methods allow the design of larger proteins as well. While there is no theoretical limit to the length of the protein which may be designed this way, there is a practical computational limit.

In an alternate preferred embodiment, only some of the residue positions of the protein are variable, and the remainder are "fixed", that is, they are identified in the three dimensional structure as being in a set conformation. In some embodiments, a fixed position is left in its original conformation (which may or may not correlate to a specific rotamer of the rotamer library being used). Alternatively, residues may be fixed as a non-wild type residue; for example, when known site-directed mutagenesis techniques have shown that a particular residue is desirable (for example, to eliminate a proteolytic site or alter the substrate specificity of an enzyme), the residue may be fixed as a particular amino acid. Alternatively, the methods of the present invention may be used to evaluate mutations de novo, as is discussed below. In an alternate preferred embodiment, a fixed position may be "floated"; the amino acid at that position is fixed, but different rotamers of that amino acid are tested. In this embodiment, the variable residues may be at least one, or anywhere from 0.1% to 99.9% of the total number of residues. Thus, for example, it may be possible to change only a few (or one) residues, or most of the residues, with all possibilities in between.

In a preferred embodiment, residues which can be fixed include, but are not limited to, structurally or biologically functional residues; alternatively, biologically functional residues may specifically not be fixed. For example, residues which are known to be important for biological activity, such as the residues which the binding site for a binding partner (ligand/receptor, antigen/antibody, etc.), phosphorylation or glycosylation sites which are crucial to biological function, or structurally important residues, such as disulfide bridges, metal binding sites, critical hydrogen bonding residues, residues critical for backbone conformation such as proline or glycine, residues critical for packing interactions, etc. may all be fixed in their amino acid identity and a single rotamer conformation, or "floated", which only fixes the identity but not the rotamer conformation.

Similarly, residues which may be chosen as variable residues may be those that confer undesirable biological attributes, such as susceptibility to proteolytic degradation, dimerization or aggregation sites, glycosylation sites which may lead to immune responses, unwanted binding activity, unwanted allostery, undesirable enzyme activity but with a preservation of binding, etc.

In a preferred embodiment, each variable position is classified as either a core, surface or boundary residue position, although in some cases, as explained below, the variable position may be set to glycine to minimize backbone strain. In addition, as outlined herein, residues need not be classified, they can be chosen as variable and any set of amino acids may be used. Any combination of core, surface and boundary positions can be utilized: core, surface and boundary residues; core and surface residues; core and boundary residues, and surface and boundary residues, as well as core residues alone, surface residues alone, or boundary residues alone.

The classification of residue positions as core, surface or boundary may be done in several ways, as will be appreciated by those in the art. In a preferred embodiment, the classification is done via a visual scan of the original protein backbone structure, including the side chains, and assigning a classification based on a subjective evaluation of one skilled in the art of protein modeling. Alternatively, a preferred embodiment utilizes an assessment of the orientation of the Cα–Cβ vectors relative to a solvent accessible surface computed using only the template Cα atoms, as outlined in U.S. Ser. Nos. 60/061,097, 60/043,464, 60/054,678, 09/127,926 60/104,612, 60/158,700, 09/419,351, 60/181630, 60/186,904, 60/132,475, 60/133,714, U.S. patent application, entitled Protein Design Automation For Protein Libraries (Filed: Apr. 14, 2000; Inventor: Bassil Dahiyat) and PCT US98/07254. Alternatively, a surface area calculation can be done.

Suitable core and boundary positions for XA proteins are outlined below.

Once each variable position is classified as either core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that will be evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the a scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used). Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues. Finally, boundary positions are generally chosen from alanine, serine, threonine, aspartic acid, asparagine, glutamine, glutamic acid, arginine, lysine histidine, valine, isoleucine, leucine, phenylalanine, tyrosine, tryptophan, and methionine. The rotamer set for each boundary position thus potentially includes every rotamer for these seventeen residues (assuming cysteine, glycine and proline are not used, although they can be). Additionally, in some preferred embodiments, a set of 18 naturally occurring amino acids (all except cysteine and proline, which are known to be particularly disruptive) are used.

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize or multimerize, or have ligand binding sites, may contain hydrophobic surface residues, etc. In addition, residues that do not allow helix "capping" or the favorable interaction with an α-helix dipole may be subtracted from a set of allowed residues. This modification of amino acid groups is done on a residue by residue basis.

In a preferred embodiment, proline, cysteine and glycine are not included in the list of possible amino acid side chains, and thus the rotamers for these side chains are not used. However, in a preferred embodiment, when the variable residue position has a φ angle (that is, the dihedral angle defined by 1) the carbonyl carbon of the preceding amino acid; 2) the nitrogen atom of the current residue; 3) the α-carbon of the current residue; and 4) the carbonyl carbon of the current residue) greater than 0°, the position is set to glycine to minimize backbone strain.

Once the group of potential rotamers is assigned for each variable residue position, processing proceeds as outlined in U.S. Ser. No. 09/127,926 and PCT US98/07254. This processing step entails analyzing interactions of the rotamers with each other and with the protein backbone to generate optimized protein sequences. Simplistically, the processing initially comprises the use of a number of scoring functions to calculate energies of interactions of the rotamers, either to the backbone itself or other rotamers. Preferred PDA scoring functions include, but are not limited to, a Van der Waals potential scoring function, a hydrogen bond potential scoring function, an atomic solvation scoring function, a secondary structure propensity scoring function and an electrostatic scoring function. As is further described below, at least one scoring function is used to score each position, although the scoring functions may differ depending on the position classification or other considerations, like favorable interaction with an α-helix dipole. As outlined below, the total energy which is used in the calculations is the sum of the energy of each scoring function used at a particular position, as is generally shown in Equation 1:

$$E_{total} = nE_{vdw} + nE_{as} + nE_{h\text{-}bonding} + nE_{ss} + nE_{elec}$$ Equation 1

In Equation 1, the total energy is the sum of the energy of the van der Waals potential ($E_{vdw}$), the energy of atomic solvation ($E_{as}$), the energy of hydrogen bonding ($E_{h\text{-}bonding}$), the energy of secondary structure ($E_{ss}$) and the energy of electrostatic interaction ($E_{elec}$) The term n is either 0 or 1, depending on whether the term is to be considered for the particular residue position.

As outlined in U.S. Ser. Nos 60/061,097, 60/043,464, 60/054,678, 09/127,926, 60/104,612, 60/158,700, 09/419,351, 60/181630, 60/186,904, 60/132,475, 60/133,714, U.S. patent application, entitled Protein Design Automation For Protein Libraries (Filed: Apr. 14, 2000; Inventor:Bassil Dahiyat) and PCT US98/07254, any combination of these scoring functions, either alone or in combination, may be used. Once the scoring functions to be used are identified for each variable position, the preferred first step in the computational analysis comprises the determination of the interaction of each possible rotamer with all or part of the remainder of the protein. That is, the energy of interaction, as measured by one or more of the scoring functions, of each possible rotamer at each variable residue position with either the backbone or other rotamers, is calculated. In a preferred embodiment, the interaction of each rotamer with the entire remainder of the protein, i.e. both the entire template and all other rotamers, is done. However, as outlined above, it is possible to only model a portion of a protein, for example a domain of a larger protein, and thus in some cases, not all of the protein need be considered. The term "portion", or similar grammatical equivalents thereof, as used herein, with regard to a protein refers to a fragment of that protein. This fragment may range in size from 5–10 amino acid residues to the entire amino acid sequence minus one amino acid. Accordingly, the term "portion", as used herein, with regard to a nucleic refers to a fragment of that nucleic acid. This fragment may range in size from 6–10 nucleotides to the entire nucleic acid sequence minus one nucleotide.

In a preferred embodiment, the first step of the computational processing is done by calculating two sets of interactions for each rotamer at every position: the interaction of the rotamer side chain with the template or backbone (the "singles" energy), and the interaction of the rotamer side chain with all other possible rotamers at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid.

Thus, "singles" (rotamer/template) energies are calculated for the interaction of every possible rotamer at every variable residue position with the backbone, using some or all of the scoring functions. Thus, for the hydrogen bonding scoring function, every hydrogen bonding atom of the rotamer and every hydrogen bonding atom of the backbone is evaluated, and the $E_{HB}$ is calculated for each possible rotamer at every variable position. Similarly, for the van der Waals scoring function, every atom of the rotamer is compared to every atom of the template (generally excluding the backbone atoms of its own residue), and the $E_{vdW}$ is calculated for each possible rotamer at every variable residue position. In addition, generally no van der Waals energy is calculated if the atoms are connected by three bonds or less. For the atomic salvation scoring function, the surface of the rotamer is measured against the surface of the template, and the $E_{as}$ for each possible rotamer at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer and the template position; that is, the farther apart the two moieties, the lower the energy.

For the calculation of "doubles" energy (rotamer/rotamer), the interaction energy of each possible rotamer is compared with every possible rotamer at all other variable residue positions. Thus, "doubles" energies are calculated for the interaction of every possible rotamer at every variable residue position with every possible rotamer at every other variable residue position, using some or all of the scoring functions. Thus, for the hydrogen bonding scoring function, every hydrogen bonding atom of the first rotamer and every hydrogen bonding atom of every possible second rotamer is evaluated, and the $E_{HB}$ is calculated for each possible rotamer pair for any two variable positions. Similarly, for the van der Waals scoring function, every atom of the first rotamer is compared to every atom of every possible second rotamer, and the $E_{vdW}$ is calculated for each possible rotamer pair at every two variable residue positions. For the atomic salvation scoring function, the surface of the first rotamer is measured against the surface of every possible second rotamer, and the $E_{as}$ for each possible rotamer pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is, the farther apart the two moieties, the lower the energy.

In addition, as will be appreciated by those in the art, a variety of force fields that can be used in the PDA calculations, including, but not limited to, Dreiding I and Dreiding II [Mayo et al, J. Phys. Chem. 94:8897 (1990)], AMBER [Weiner et al., J. Amer. Chem. Soc. 106:765 (1984) and Weiner et al., J. Comp. Chem. 106:230 (1986)], MM2 [Allinger, J. Chem. Soc. 99:8127 (1977), Liljefors et al., J. Com. Chem. 8:1051 (1987)]; MMP2 [Sprague et al., J. Comp. Chem. 8:581 (1987)]; CHARMM [Brooks et al., J. Comp. Chem. 106:187 (1983)]; GROMOS; and MM3 [Allinger et al., J. Amer. Chem. Soc. 111:8551 (1989)], OPLS-AA [Jorgensen et al., J. Am. Chem. Soc. 118:11225–11236 (1996); Jorgensen, W. L.; BOSS, Version 4.1; Yale University: New Haven, Conn. (1999)]; OPLS [Jorgensen et al., J. Am. Chem. Soc.1 10:1657ff (1988); Jorgensen et al., J Am. Chem. Soc. 112:4768ff (1990)]; UNRES (United Residue Forcefield; Liwo etal., Protein Science 2:1697–1714 (1993); Liwo etal., Protein Science 2:1715–1731 (1993); Liwo et al., J. Comp. Chem. 18:849–873 (1997); Liwo et al., J. Comp. Chem. 18:874–884 (1997); Liwo et al., J. Comp. Chem. 19:259–276 (1998); Forcefield for Protein Structure Prediction (Liwo et al., Proc. Natl. Acad. Sci. U.S.A 96:5482–5485 (1999)]; ECEPP/3 [Liwo et al., J Protein Chem. 13(4):375–80 (1994)]; AMBER 1.1 force field (Weiner, et al., J. Am. Chem. Soc. 106:765–784); AMBER 3.0 force field (U.C. Singh et al., Proc. Natl. Acad. Sci. U.S.A. 82:755–759); CHARMM and CHARMM22 (Brooks et al., J. Comp. Chem. 4:187–217); cvff3.0 [Dauber-Osguthorpe, et al., Proteins: Structure, Function and Genetics, 4:31–47 (1988)]; cff91 (Maple, et al., J. Comp. Chem. 15:162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference.

Once the singles and doubles energies are calculated and stored, the next step of the computational processing may occur. As outlined in U.S. Ser. No. 091127,926 and PCT US98/07254, preferred embodiments utilize a Dead End Elimination (DEE) step, and preferably a Monte Carlo step.

PDA, viewed broadly, has three components that may be varied to alter the output (e.g. the primary library): the scoring functions used in the process; the filtering technique, and the sampling technique.

In a preferred embodiment, the scoring functions may be altered. In a preferred embodiment, the scoring functions outlined above may be biased or weighted in a variety of ways. For example, a bias towards or away from a reference sequence or family of sequences can be done; for example, a bias towards wild-type or homolog residues may be used. Similarly, the entire protein or a fragment of it may be biased; for example, the active site may be biased towards wild-type residues, or domain residues towards a particular desired physical property can be done. Furthermore, a bias towards or against increased energy can be generated. Additional scoring function biases include, but are not limited to applying electrostatic potential gradients or hydrophobicity gradients, adding a substrate or binding partner to the calculation, or biasing towards a desired charge or hydrophobicity.

In addition, in an alternative embodiment, there are a variety of additional scoring functions that may be used. Additional scoring functions include, but are not limited to torsional potentials, or residue pair potentials, or residue entropy potentials. Such additional scoring functions can be used alone, or as functions for processing the library after it is scored iniially. For example, a variety of functions derived from data on binding of pepbdes to MHC (Major Histocompatibility Complex) can be used to rescore a library in order to eliminate proteins containing sequences which can potentially bind to MHC, i.e. potentially immunogenic sequences.

In a preferred embodiment, a variety of filtering techniques can be done, including, but not limited to, DEE and its related counterparts. Additional filtering techniques include, but are not limited to branch-and-bound techniques for finding optimal sequences (Gordon and Mayo, Structure Fold. Des. 7:1089–98, 1999), and exhaustive enumeration of sequences.

As will be appreciated by those in the art, once an optimized sequence or set of sequences is generated, a variety of sequence space sampling methods can be done, either in addition to the preferred Monte Carlo methods, or instead of a Monte Carlo search. That is, once a sequence or set of sequences is generated, preferred methods utilize sampling techniques to allow the generation of additional, related sequences for testing.

These sampling methods can include the use of amino acid substitutions, insertions or deletions, or recombinations of one or more sequences. As outlined herein, a preferred embodiment utilizes a Monte Carlo search, which is a series of biased, systematic, or random jumps. However, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example, etc.). Jumps where multiple residue positions are coupled (two residues always change together, or never change together), jumps where whole sets of residues change to other sequences (e.g., recombination). Similarly, for all the sampling techniques, the acceptance criteria of whether a sampling jump is accepted can be altered.

In addition, it should be noted that the preferred methods of the invention result in a rank ordered list of sequences; that is, the sequences are ranked on the basis of some objective criteria. However, as outlined herein, it is possible to create a set of non-ordered sequences, for example by generating a probability table directly (for example using SCMF analysis or sequence alignment techniques) that lists sequences without ranking them. The sampling techniques outlined herein can be used in either situation.

In a preferred embodiment, Boltzman sampling is done. As will be appreciated by those in the art, the temperature criteria for Boltzman sampling can be altered to allow broad searches at high temperature and narrow searches close to local optima at low temperatures (see e.g., Metropolis et al., J. Chem. Phys. 21:1087, 1953).

In a preferred embodiment, the sampling technique utilizes genetic algorithms, e.g., such as those described by Holland (Adaptation in Natural and Artifical Systems, 1975, Ann Arbor, U. Michigan Press). Genetic algorithm analysis generally takes generated sequences and recombines them computationally, similar to a nucleic acid recombination event, in a manner similar to "gene shuffling". Thus the "jumps" of genetic algorithm analysis generally are multiple position jumps. In addition, as outlined below, correlated multiple jumps may also be done. Such jumps can occur with different crossover positions and more than one recombination at a time, and can involve recombination of two or more sequences. Furthermore, deletions or insertions (random or biased) can be done. In addition, as outlined below, genetic algorithm analysis may also be used after the secondary library has been generated.

In a preferred embodiment, the sampling technique utilizes simulated annealing, e.g., such as described by Kirkpatrick et al. [Science, 220:671–680 (1983)]. Simulated annealing alters the cutoff for accepting good or bad jumps by altering the temperature. That is, the stringency of the cutoff is altered by altering the temperature. This allows broad searches at high temperature to new areas of sequence space, altering with narrow searches at low temperature to explore regions in detail.

In addition, as outlined below, these sampling methods can be used to further process a first set to generate additional sets of XA proteins.

The computational processing results in a set of optimized XA protein sequences. These optimized XA protein sequences are generally significantly different from the wild-type xylanase sequence from which the backbone was taken. That is, each optimized XA protein sequence preferably comprises at least about 3–10% variant amino acids from the starting or wild type sequence, with at least about 10–15% being preferred, with at least about 15–20% changes being more preferred and at least 25% being particularly preferred.

In a preferred embodiment, the XA proteins of the invention have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different residues from the *Bacillus circulans* xylanase sequence.

Thus, in the broadest sense, the present invention is directed to XA proteins that have xylanase activity. By "Xylanase activity" or "XA" herein is meant that the XA protein exhibits at least one, and preferably more, of the biological functions of a xylanase, as defined below. In one embodiment, the biological function of an XA protein is altered, preferably improved, over the corresponding biological activity of the *B. circulans* xylanase.

By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e., "analogs" such as peptoids [see Simon et al., Proc. Natl. Acad. Sci. U.S.A. 89(20:9367–71 (1992)], generally depending on the method of synthesis. Thus "amino acid", or "peptide residue", as used herein means both naturally occurring and synthetic amino acids. For example, homo-phenylalanine, citrulline, and noreleucine are considered amino acids for the purposes of the invention. "Amino acid" also includes amino acid residues such as proline and hydroxyproline. In addition, any amino acid representing a component of the XA proteins can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability, and therefore are advantageous in the formulation of compounds which may have longer in vivo half lives, when administered by oral, intravenous, intramuscular, intraperitoneal, topical, rectal, intraocular, or other routes. In the preferred embodiment, the amino acids are in the (S) or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Left 428:(1–2) 68–70 May 22 1998 and Tang et al., Abstr. Pap Am. Chem. S218:U138-U138 Part 2 Aug. 22, 1999, both of which are expressly incorporated by reference herein.

Additionally, modified amino acids or chemical derivatives of amino acids of consensus or fragments of XA proteins, according to the present invention may be provided, which polypepbdes contain additional chemical moieties or modified amino acids not normally a part of the protein. Covalent and non-covalent modifications of the protein are thus included within the scope of the present invention. Such modifications may be introduced into an XA polypeptide by reacting targeted amino acid residues of the polypeptide with an organic derivatzing agent that is capable of reacting with selected side chains or terminal residues. The following examples of chemical derivatives are provided by way of illustration and not by way of limitation.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1–C20.

Acidic amino acids can be substituted with non-carboxylate amino acids while maintaining a negative charge, and derivatives or analogs thereof, such as the non-limiting examples of (phosphono)alanine, (phosphono) glycine, (phosphono)leucine, (phosphono)isoleucine, (phosphono)threonine, or (phosphono)serine; or sulfated (e.g., —SO$_3$H) threonine, serine, tyrosine.

Other substitutions may include unnatural hyroxylated amino acids that may be made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Preferred alkyl groups herein contain 1 to 12 carbon atoms. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, and nitrogen being preferred. Alkyl includes substituted alkyl groups. By "substituted alkyl group" herein is meant an alkyl group further comprising one or more substitution moieties. A preferred heteroalkyl group is an alkyl amine. By "alkyl amine" or grammatical equivalents herein is meant an alkyl group as defined above, substituted with an amine group at any position. In addition, the alkyl amine may have other substitution groups, as outlined above for alkyl group. The amine may be primary (—NH$_2$R), secondary (—NHR$_2$), or tertary (—NR$_3$). Basic amino acids may be subsbtuted with alkyl groups at any position of the naturally occurring amino acids lysine, arginine, ornithine, citrulline, or (guanidino)-acetic acid, or other (guanidino) alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the XA polypepudes can be replaced by a ketomethylene moiety. Such derivatives are expected to have the property of increased stability to degradation by enzymes Additional amino acid modifications of amino acids of XA polypeptides of the present invention may include the following: Cysteinyl residues may be reacted with alpha-haloacetates (and corresponding amines), such as 2-chloroacetc acid or chloroacetamide, to give carboxymethyl or carboxyamidomethyl derivatives. Cysteinyl residues may also be derivatzed by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri4-nitrophenol, or chloro-7-nitrobenzo-2-oxa-1,3-diazole.

Histidyl residues may be derivatzed by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; 0-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatzation of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4-azonia4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

The xylanase may be from any number of organisms, with xylanase from *Bacillus circulans* being particularly preferred. Suitable organisms include, but are not limited to bacteria, archaebacteria, yeast and fungi and plants. The GenBank accession numbers for a variety of endo-1,4-beta xylanases (xylanase) proteins and nucleic acids encoding same, include, but are not limited to: *Acidobacterium capsulatum* (JE0182); *Arabidopsis thaliana* (T00624);

Aspergillus awamori (S48229); Aspergillus kawachii (BAA07264, BAA03576, BAA03575); Aspergillus niger (BM07265, JT0608, JC1198); Aspergillus tubigensis (S49542); Bacillus circulans (S01734); Bacillus polymyxa (S19011); Bacillus pumilus (S00067, WWBSXP); Bacillus sp. (T17628, JC7103, 140356, JD0003); Bacillus subtilis (H69735, G69849, F69829; 140569); Bacillus stearothermophilus (140570,139760); Bacteroides ovatus (S55892); barley (T06195, T06191); Caldicellulosiruptor sp. (T31085, T31082); Caldocellum saccharolyticum (T30909, A60154); Cellulomonas fimi (T31351,140712); Cellvibrio mixtus (S59631); Chaetomium gracile (BAA08650, BAA08649, S71472, S71473); Clostridium acetobutylium (S12745); Clostridium stercorarium (JC2484, JQ1 935); Clostridium thermocellum (S54975, A31842); Cryptococcus sp. (JC4909); Dictyoglomus thermophilum (T08469); Emericella nidulans (JC5034, S57477, S57469); Filobasidium floriforme (JS0734); Humicola grisea (JC5861); Humicola insolens (S43919); Neocallimastix frontalis (S48865); Neocallimastix patriciarum (S43846; S24754); Nocardiopsis dassonvillei (PQ0203); Penicillium chrysogenum (JN0575); Pseudomonas fluorescens (S59633, S59634, S13391, S06047); Ruminococcus flavefaciens (S51592, S20907); Ruminococcus sp. (S58235); Schizophyllum commune (A44597); Streptomyces sp. (S70615, S47512); Streptomyces coelicolor (T37005, CAB61738); Streptomyces lividans (JS0591, JS0590, JS0589); Streptomyces roseiscleroticus (C57001, A57001, B57001, D57001); Streptomyces thermoviolaceus (B43937, A43937); Thermoanaerobacterium saccharolyticum (A48490); thermophilic bacterium RT8.B4 (S41788); Thermoascus Aurantiacus (1TAXA, 1TIXA, AAF24127, CAB65468); Thermotoga maritima (strain MSB8) (B72423, S61311); Thielavia terrestris (A44598); Trichoderma viride (A44595, A44594); Trichoderma harzianum (A44593); Trichoderma reesei (S39883, S39155, S39154).

The XA proteins of the invention exhibit at least one biological function of a xylanase. By "xylanase" herein is meant a wild type xylanase or an allelic variant thereof. Included within this definition are, for example, the B. circulans xylanase and the B. subtilis xylanase; these two enzymes are identical except at position 147, where B. circulans has a threonine and B. subtilis has a serine. In its broadest term, xylanase refers to all forms of xylanase that are active in accepted xylanase assays.

In a preferred embodiment, a xylanase belongs to the Family 11 of xylanases. An enzyme is classified in family 11 if it possesses the conserved amino acid residues common to Family 11, including the two glutamic acid residues serving as the essential catalytic residues [see Wakarchuk et al., Protein Sci. 3:467–475 (1994)].

The XA proteins of the invention exhibit at least one biological function of a xylanase. By "biological function" or "biological property" herein is meant any one of the properties or functions of a xylanase including, but not limited to, the ability to hydrolyze pulp xylan, the ability to hydrolyze pure xylan, and the ability to hydrolyze cellulose, and the ability to be secreted.

"Hydrolyzing xylan" herein means hydrolyzing the 1,4-beta-D-xyloside bond of xylan to thereby produce reducing sugars of xylooligosaccharides.

"Xylan" as used herein, includes birch xylan, oat spelt xylan, as well as xylan-containing materials including hardwood kraft pulp and oat spelt pulp.

All of these XA proteins will exhibit at least 50% of the biological activity as the wild type B. circulans xylanase. More preferred are XA proteins that exhibit at least 75%, even more preferred are XA proteins that exhibit at least 90%, and most preferred are XA proteins that exhibit more than 100% of the biological activity as the wild type xylanase. Xylanase assays are described in U.S. Pat. Nos. 5,405,769; 5,736,384; 5,759,840; Arase et al. [FEB Left. 316(2):123–7 (1993)]; Wakarchuk et al. [Protein Sci. 3(3):467–75 (1994); Protein Eng. 7(11):1379–86 (1994)]; and reference cited therein, all of which are expressly incorporated by reference.

In one embodiment, at least one biological property of the XA protein is altered when compared to the same property of B. circulans xylanase. As outlined above, the invention provides XA nucleic acids encoding XA polypeptides. The XA polypeptide preferably has at least one property, which is substantially different from the same property of the corresponding naturally occurring B. circulans xylanase. polypeptide. The property of the XA polypepbde is the result the PDA analysis of the present invenbon.

The term "altered property" or grammatical equivalents thereof in the context of a polypeptide, as used herein, refer to any characteristic or attribute of a polypeptide that can be selected or detected and compared to the corresponding property of a naturally occurring protein. These properties include, but are not limited to oxidative stability, substrate specificity, substrate binding or catalytic activity, thermostability, thermophilicity, alkaline stability, alkalophilicity, pH activity profile, resistance to proteolytic degradation, Km, kcat, Km/kcat ratio, kinetic association ($K_{on}$) and dissociation ($K_{off}$) rate, protein folding, ability to be secreted, ability to be modified by phosphorylabon or glycosylation Unless otherwise specified, a substantial change in any of the above-listed properties, when comparing the property of an XA polypeptide to the property of a naturally occurring B. circulans xylanase is at least a 10%, preferably at least a 20%, more preferably, 50%, more preferably at least a 2-fold increase or decrease.

A change in oxidative stability is evidenced by at least about 20%, more preferably at least 50% increase of activity of an XA protein when exposed to various oxidizing conditions as compared to that of B. circulans xylanase. Oxidative stability is measured by known procedures.

The term "thermophilicity", as used herein is defined as the ability of an enzyme to be active at a high temperature. For example, a XA protein has more thermophilicity than B. circulans xylanase if it is more efficient in hydrolyzing a substrate, such as xylan, at a temperature higher than the optimum for the B. circulans xylanase. Thermophilicity relates to enzyme activity in the presence of substrate. In the present invention, the substrate can be pulp xylan or purified xylan. The XA protein will have a temperature optimum which is at least 1° C. greater than the temperature optimum for the B. circulans xylanase, preferably at least 3° C.–5° C., more preferably at least 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., or 25° C., In some embodiments, the shift in temperature optimum may be as high 30° C., to 35° C. and even up to 60° C. Included within this definition of thermophilicity is a XA protein, which has at least one temperature at which it hydrolyzes a substrate more efficient than the B. circulans xylanase. In another example, a shift in temperature of 5° C. means that the XA enzyme has the same activity as the wild type B. circulans xylanase, however at a 5° C. higher temperature. Generally, thermophilicity is measured by known procedures.

The term "substrate", as used herein refers to a substrate of an enzyme. In a preferred embodiment, the substrate is xylan and the enzyme is xylanase or a XA protein. In one aspect of this embodiment the substrate is a derivative of xylan. Most xylanase enzymes are effective at higher temperatures in the hydrolysis of pure xylan than in the treatment of pulp. This is due to a combination of factors relating to the substrates (i.e. inhibitors present in the pulp) and to the length of time, pH, and other aspects of the procedures used to carry out the tests. Quantitative measures of thermophilicity refer herein to xylan substrates unless otherwise indicated.

The term "thermostability" or "thermal stability" or grammatical equivalents thereof, as used herein, is defined as the ability of an enzyme to be stored or incubated at a high temperature in the absence of substrate, such as xylan, and then exhibit xylanase activity when returned to standard assay conditions. For example, an XA protein is more thermostable than B. circulans xylanase if it can be held at 65° C.–70° C. for a period of time and still retains a greater percentage of its activity when compared to the B. circulans xylanase, which loses all or most of its activity after 24 hours at 65° C.–70° C. Thus, in contrast to thermophilicity, thermostability relates to the enzyme activity remaining after incubation in the absence of a substrate, such as xylan [Mathrani and Ahring, Appl. Microbiol. Biotechnol. 38:23–27 (1992)].

A change in thermostability is evidenced by at least about a 5% or greater increase or decrease (preferably increase) in the half life of the activity of an XA protein when exposed to a relatively high temperature and neutral pH as compared to that of B. circulans xylanase Generally, thermal stability is measured by known procedures.

The term "alkalophilicity", as used herein is defined as the ability of an enzyme to be active at a high (alkaline) pH. For example, an XA protein has more alkalophilicity than B. circulans xylanase if it is more efficient in hydrolyzing a substrate, such as xylan, at a pH higher than the optimum for the B. circulans xylanase. Alkalophilicity is analogous to thermophilicity and relates to enzyme activity in the presence of a substrate, such as xylan. The XA protein will have a pH optimum which is at least greater by 0.1, preferably at least greater than 0.3–0.5, more preferably at least greater than 0.5–1.0, 1–0–2.0, 2.0–3.0, 3.0–4.0, 4.0–5.0, or 5.0–6.0. Included within this definition of alkalophilicity is a XA protein, which has at least one pH at which it hydrolyzes a substrate more efficient than the B. circulans xylanase. In another example, a shift in pH of 3.0 means that the XA enzyme has the same activity as the wild type B. circulans xylanase, however at a pH that is 3.0 higher. Generally, alkalophilicity is measured by known procedures.

Accordingly, the term "alkaline stability" or grammatical equivalents thereof, as used herein refers ability of an enzyme to be stored or incubated at a high pH in the absence of substrate, such as xylan, and then exhibit xylanase activity when returned to standard assay conditions. For example, an XA protein is more alkaline stable than B. circulans xylanase if it can be held at pH 8 and retain all or most of its activity, while B. circulans xylanase loses all or most of its activity after being held at pH 8 for the same time. Thus, in contrast to alkalophilicity, alkaline stability relates to the enzyme activity remaining after incubation in the absence of a substrate, such as xylan.

A change in alkaline stability is evidenced by at least about a 5% or greater increase or decrease (preferably increase) in the activity of an XA protein when exposed to increasing or decreasing pH conditions as compared to that of B. circulans xylanase. Generally, alkaline stability is measured by known procedures.

Production, purification procedures and assays for xylanases, including (i) standard assays for the measurement of enzymatic activity, (ii) assays for determining the temperature/activity profile of xylanases, (iii) assays for comparing the thermophilicity of xylanases (iv) assays for determining the pH/activity profile of xylanases, (v) assays for measuring the thermostability of xylanases, (vi) assays for evaluating the performance of xylanases in treatment of pulp, (vii) bleaching of pulp are described in U.S. Pat. Nos. 5,759,840, 5,736,384 and 5,405,769 and in the references cited therein, all of which are expressly incorporated by reference. A preferred xylanase assay that can be used for high throughput assays is described by Green et al. [Analytical Biochemistry 182:197–199 (1989); hereby expressly incorporated by reference].

Similarly, XA proteins, for example are experimentally tested and validated in in vitro assays. Suitable assays include, but are not limited to e.g., examining their binding affinity to naturally occurring substrates or variant substrates. Quantitative comparison are made comparing kinetic and equilibrium binding constants for the B. circulans xylanase to a substrate and of the XA proteins to a substrate. The kinetic association rate ($K_{on}$) and dissociation rate ($K_{off}$), and the equilibrium binding constants ($K_d$) can be determined using surface plasmon resonance on a BIAcore instrument following the standard procedure in the literature [Pearce et al., Biochemistry 38:81–89 (1999)]. Comparing the binding constant between B. circulans xylanase and a substrate to the binding constant of an XA protein and the same substrate, the sensitivity and specificity of the XA protein can be determined. Preferably, binding affinity of the XA protein to a substrate increases relative to the B. circulans xylanase.

A change in substrate specificity is defined as a difference between the kcat/Km ratio of the naturally occurring protein, such as B. circulans xylanase and that of a variant thereof, such as an XA protein of the invention. The kcat/Km ratio is generally a measure of catalytic efficiency. Generally, the objective will be to generate variants of naturally occurring proteins with greater (numerically large) kcat/Km ratio for a given substrate when compared to that of the naturally occurring protein, thereby enabling the use of the protein to more efficiently act on a target substrate. An increase in kcat/Km ratio for one substrate may be accompanied by a reduction in kcat/Km ratio for another substrate. This is a shift in substrate specificity and variants of naturally occurring proteins exhibiting such shifts have utility where the naturally occurring protein is undesirable, e.g., to prevent undesired hydrolysis of a particular substrate in an admixture of substrates. Km and kcat are measured in accord with known procedures.

The XA proteins and nucleic acids of the invention are distinguishable from naturally occurring B. circulans xylanase. By "naturally occurring" or "wild type" or grammatical equivalents, herein is meant an amino acid sequence or a nucleotide sequence that is found in nature and includes allelic variations; that is, an amino acid sequence or a nucleotide sequence that usually has not been intentionally modified. Accordingly, by "non-naturally occurring" or "synthetic" or "recombinant" or grammatical equivalents thereof, herein is meant an amino acid sequence or a nucleotide sequence that is not found in nature; that is, an amino acid sequence or a nucleotide sequence that usually has been intentionally modified. It is understood that once a recombinant nucleic acid is made and reintroduced into a host cell or organism, it will replicate non-recombinantly, i.e., using the in vivo cellular machinery of the host cell rather than in vitro manipulations, however, such nucleic acids, once produced recombinantly, although subsequently replicated non-recombinantly, are still considered recombinant for the purpose of the invention. Representative amino acid and nucleotide sequences of a naturally occurring *B. circulans* xylanase are shown in FIG. 1 (SEQ ID NOS:1,2). It should be noted that unless otherwise stated, all positional numbering of XA proteins and XA nucleic acids is based on these sequences. That is, as will be appreciated by those in the art, an alignment of *B. circulans* xylanase and XA proteins can be done using standard programs, as is outlined below, with the identification of "equivalent" positions between the two proteins. Thus, the XA proteins and nucleic acids of the invention are non-naturally occurring; that is, they do not exist in nature.

Thus, in a preferred embodiment, the XA protein has an amino acid sequence that differs from a wild-type *B. circulans* xylanase sequence by at least 3% of the residues. That is, the XA proteins of the invention are less than about 97% identical to a *B. circulans* xylanase amino acid sequence. Accordingly, a protein is an "XA protein" if the overall homology of the protein sequence to the amino acid sequence shown in FIG. 1A or FIG. 1B (SEQ ID NO:1) is preferably less than about 97%, more preferably less than about 95%, even more preferably less than about 90% and most preferably less than 85%. In some embodiments the homology will be as low as about 75 to 80%. Stated differently, based on the sequence of the secreted form of *B. circulans* xylanase of 185 residues (see FIG. 1A and FIG. 1B) (SEQ ID NO:1:), XA proteins have at least about 5 to 6 residues that differ from the *B. circulans* xylanase sequence (3%), with XA proteins having from 5 residues to upwards of 33 residues or even upwards to 79 residues being different from the *B. circulans* xylanase sequence. Preferred XA proteins have 5–30 different residues with from about 5 to about 15 being particularly preferred (that is, about 3–8% of the protein is not identical to *B. circulans* xylanase).

In another preferred embodiment, XA proteins have 2, 3, 4, 5, 6, 7, 8, 9, 10, 11, 12, 13, 14, 15, 16, 17, 18,19, 20, 21, 22, 23, 24, 25, 26, 27, 28, 29, 30, 31, 32, 33, 34, 35, 36, 37, 38, 39, or 40 different residues from the *B. circulans* xylanase sequence.

Homology in this context means sequence similarity or identity, with identity being preferred. As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403–410, (1990); Altschul et al., Nucleic Acids Res. 25:3389–3402 (1997); and Karlin et al., Proc. Natl. Acad. Sci. U.S.A. 90:5873–5787 (1993). A particularly useful BLAST program is the WU-BLAST-2 program which was obtained from Altschul et al., Methods in Enzymology, 266:460–480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., Nucl. Acids Res., 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleobde residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 1 (SEQ ID NOS:1,2), it is understood that in one embodiment, the percentage of sequence identity will be determined based on the number of identical amino acids in relation to the total number of amino acids. Thus, for example, sequence identity of sequences shorter than that shown in FIG. 1, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Thus, XA proteins of the present invention may be shorter or longer than the amino acid sequence shown in FIG. 1A (SEQ ID NO:1). Thus, in a preferred embodiment, included within the definition of XA proteins are portions or fragments of the sequences depicted herein. Fragments of XA proteins are considered XA proteins if a) they share at least one antigenic epitope; b) have at least the indicated homology; c) and preferably have XA biological activity as defined herein.

In a preferred embodiment, as is more fully outlined below, the XA proteins include further amino acid variations, as compared to the wild type B. circulans xylanase, than those outlined herein. In addition, as outlined herein, any of the variations depicted herein may be combined in any way to form additional novel XA proteins.

In addition, XA proteins can be made that are longer than those depicted in the figures, for example, by the addition of epitope or purification tags, as outlined herein, or the addition of other fusion sequences.

It is well known in the art that xylanase also has uses in non-pulp applications. For example, xylanases have been reported to be useful in clarifying juice and wine [Zeikus et al., ACS Symp. Ser. 460:36–51 (1991); Beily, ACS Symp. Ser. 460:408416 (1991); Woodward, Top Enzyme Ferment. Biotechnol. 8:9–30 (1984)]; extracting coffee, plant oils and starch [Beily, supra; Woodward supra; McCleary, Int. J. Biol. Macromol. 8:349–354 (1986)]; for the production of food thickeners (Zeikus et al., supra); altering texture in bakery products, e.g., improving the quality of dough, help bread rise and processing of wheat and corn for starch production (Maat et al. In Xylans and xylanases, eds. Visseret al., Elsevier Sci pub., Amsterdam. ISBN 0-444-894-772 (1992); McCleary, supra; Krishnarau et al., J. Food Sci. 59:1251–1254 (1994); U.S. Pat. No. 5,306,633); for use as animal food additives to aid in the digestibility of feedstuffs; and in the washing of super precision devices and semiconductors [Takayuki et al., U.S. Pat. No. 5,078,802). Several of these application could benefit from a thermostable xylanase, for example, food processing at elevated temperatures.

Due to the sequence homology among related xylanases, one could expect that the introduction of mutations into one member of the xylanase family, for example, as demonstrated in the examples below for B. circulans xylanase, could be extended to other xylanases from bacteria, archaebacteria, yeast, fungi or plants and produce similar effects.

In a preferred embodiment, the xylanase used for PDA design is *Bacillus subtilis* xylanase (FIG. 16A) (SEQ ID NO:13); *Bacillus pumilus* xylanase (FIG. 16B) (SEQ ID NO:14); *Streptomyces lividans* xylanase B (FIG. 16C) (SEQ ID NO:15); *Streptomyces lividans* xylanase C (FIG. 16D) (SEQ ID NO:16); *Clostridium acetobutyliticum* xylanase (FIG. 16E) (SEQ ID NO:17); *Schizophyllum commune* xylanase (FIG. 16F) (SEQ ID NO:18); *Trichoderma viride* xylanase (FIG. 16G) (SEQ ID NO:19); *Trichoderma harzianum* xylanase (FIG. 16H) (SEQ ID NO:20); *Trichoderma reesei* xyn I xylanase (FIG. 16I) (SEQ ID NO:21); *Trichoderma reesei* xyn II xylanase (FIG. 16J) (SEQ ID NO:22); *Paecilomyces variotii* xylanase (FIG. 16K) (SEQ ID NO:23); *Thermomyces lanuginosus* xylanase (FIG. 16L) (SEQ ID NO:24); *Aspergillus niger* xylanase (FIG. 16M) (SEQ ID NO:25); *Aspergillus awamori* var. *kawachi* xylanase A (FIG. 16N) (SEQ ID NO:26); *Aspergillus awamori* var. *kawachi* xylanase (FIG. 16O) (SEQ ID NO:27); *Neocalimastix patriciarum* xylanase (FIG. 16P) (SEQ ID NO:28); *Cochliobolus carbonum* xylanase (FIG. 16Q) (SEQ ID NO:29); *Clostridium stercorarium* xylanase (FIG. 16R) (SEQ ID NO:30); *Ruminococcus flavefaciens* xylanase (FIG. 16S) (SEQ ID NO:31); *Fibrobacter succinogenes* xylanase (FIG. 16T) (SEQ ID NO:32); *Aspergillus tubigensis* xylanase (FIG. 16U) (SEQ ID NO:33); or Bacillus sp. strain 41M-1 xylanase (FIG. 16V) (SEQ ID NO:34).

In a preferred embodiment, the PDA design is performed on the *Trichoderma reesei* xylanase (xynII) sequence. The structure of the fungal xylanase from *Trichoderma reesi* (xynII)as solved by Torronen and Rouvinen [Biochemistry 34:847 (1995)] was taken from the PDB server, entry 1XYP.

In another preferred embodiment, the xylanase used for PDA design is Bacillus sp. B2113.

In a particularly preferred embodiment, the xylanase used for PDA design is *B. circulans* xylanase (PDB entry 1XNB).

The XA proteins of the invention comprise variable amino acid residues in core residues, in regions around D83, in the helix region and around the active site region.

In a preferred embodiment, the XA proteins comprise variable amino acid residues in core residues.

B. circulans xylanase core residues are as follows: positions 26, 28, 30, 36, 38, 51, 53, 55, 58, 62, 64, 66, 68, 70, 72, 77, 79, 81, 105, 107, 130, 142, 144, 146, 153, 169, 171, 173, 176, 178, 180, 182, and 184 (see FIG. 3). Accordingly, in a preferred embodiment, XA proteins have variable positions selected from these positions.

In a preferred embodiment, XA proteins have variable positions selected solely from core residues of B. circulans xylanase. Alternatively, at least a majority (51 %) of the variable positions are selected from core residues, with at least about 75% of the variable positions being preferably selected from core residue positions, and at least about 90% of the variable positions being particularly preferred. A specifically preferred embodiment has only core variable positions altered as compared to B. circulansxylanase.

Particularly preferred embodiments where XA proteins have variable positions as compared to B. circulans xylanase comprise the CORE region, as shown in FIG. 4.

In one embodiment, the variable core positions are altered to any of the other 19 amino acids. In a preferred embodiment, the variable core residues are chosen from Ala, Val, Phe, Ile, Leu, Tyr, Trp and Met. In another preferred embodiment, the variable core residues are chosen from Ala, Val, Leu, Ile, Phe, Tyr, and Trp plus the original wild type residue.

In a preferred embodiment, the XA protein of the invention has a sequence that differs from a wild-type B. circulans xylanase protein in at least one amino acid position selected from positions 5, 7, 11, 26, 28, 30, 36, 37, 38, 39, 51, 53, 55, 58, 62, 63, 64, 65, 66, 67, 68, 70, 71, 72, 77, 79, 80, 81, 82, 83, 84, 85, 88, 95, 96, 98, 100, 101, 102, 103, 105, 107, 109, 110, 115, 118, 125, 128, 129, 130, 132, 136, 138, 142, 144, 146, 147, 148, 149, 150, 152, 153, 156, 157, 158, 160, 161, 164, 167, 168, 169, 170, 171, 173, 176, 178, 180, 182, and 184; see also FIG. 3, which outlines sets of amino acid positions.

In another preferred embodiment, the XA protein of the invention has a sequence that differs from a wild type B.

*circulans* xylanase sequence in at least one amino acid position selected from the positions 26, 28, 30, 36, 38, 51, 53, 55, 58, 62, 64, 66, 68, 70, 72, 77, 79, 81, 105, 107, 130, 142, 144, 146, 153, 169, 171, 173, 176, 178, 180, 182, and 184 (see FIG. 3).

In one aspect of this embodiment, preferred amino acid changes within the CORE region are as follows (see FIG. 4A): Y26F; V28I; V28A; V28S; V28L; V28W: W30F; W30Y; F36L; F36Y; V38I; I51L; I51V; Y53F; Y53W; A55S; W58F; W58A; W58S; G64V; G64A; L68V; I77V; I77L; Y79F;Y79W; V81I; Y105F; I107V; I107L; S130A; A142L; A142S; A142V; I144V; I144L; F146I; F146 Y; F146V; W153L; M169L; T171L; T171I; T171V; G173A; S176A; S180A; S180F; V182I; and V182L. These may be done either individually or in combination, with any combination possible. However, as outlined herein, preferred embodiments utilize at least five, and preferably more variable positions in each XA protein.

In one particularly preferred embodiment, a preferred XA protein comprises the following changes (see FIG. 4B) (SEQ ID NO:3); Y26F, V28I, W30F, Y53F, W58F, G64V, Y79F, Y105F, A142L, T171L, S176A, S180A, and V182I.

Particularly preferred embodiments where XA proteins have variable positions as compared to *B. circulans* xylanase comprise the 'Region around D83', as shown in FIGS. 5–10.

In a preferred embodiment, XA proteins have variable positions selected solely from 'Regions around D83' residues of *B. circulans* xylanase. Alternatively, at least a majority (51%) of the variable positions are selected from 'Regions around D83' residues, with at least about 75% of the variable positions being preferably selected from 'Regions around D83' residue positions, and at least about 90% of the variable positions being particularly preferred. A specifically preferred embodiment has only 'Regions around D83' variable positions altered as compared to *B. circulans* xylanase.

In one embodiment, the variable 'Region around D83' positions are altered to any of the other 19 amino acids. In a preferred embodiment, the variable core residues are chosen from Ala, Val, Phe, Ile, Leu, Tyr, Trp and Met. In another preferred embodiment, the variable core residues are chosen from Ala, Val, Leu, Ile, Phe, Tyr, and Trp plus the original wild type residue. In another embodiment, the variable residues were chosen from boundary rotamers (Ala, Val, Leu, Ile, Phe, Trp, Asp, Asn, Glu, Gln, Lys, Ser, Thr, His, Arg, Met).

In another preferred embodiment, the XA protein of the invention has a sequence that differs from a wild type *B. circulans* xylanase sequence in at least one amino acid position selected from the positions 53, 66, 67, 68, 81, 82, 83, 84, 85, 101, 105, 132, 136, 138, 142, 144, 149, and 169 (see FIG. 3).

In one aspect of this embodiment, preferred amino acid changes within the 'Region around D83' are as follows (see FIGS. 5A, 6A, 9A, 10A): Y53F; Y53W; L66F; T67A; T67D; T67S; T67N; L68V; L68I; V81A; V82L; V82T; V82D; D83V; D83F; D83T; S84V; S84A; S84T; S84D; W85F; W85Y; D101N; D101A; D101S; Y105F; R132M; R132L; R132A; R132S; R136M; R136K; R136L; R136I; R136F; R136E; R136A; T138V; T138D; T138L; T138A; T138S; T138N; T138Hsp; A142L; A142I; A142V; A142F; I144L; I144A; H149F; H149Y; and M169L. These may be done either individually or in combination, with any combination possible. However, as outlined herein, preferred embodiments utilize at least five, and preferably more variable positions in each XA protein.

In one particularly preferred aspect of this embodiment, a preferred XA protein comprises the following changes (see FIGS. 5B and 6B) (SEQ ID NO:4); Y53F, D83V, S84V, W85F, Y105F, R132M, R136M, A142L, I144L, and H149F.

In another preferred aspect of this embodiment, a preferred XA protein comprises the following changes (see FIG. 9B) (SEQ ID NO:6): Y53F, D83V, S84V, W85F, Y105F, R132A, R136L, A142L, I144L, and H149F.

In another preferred aspect of this embodiment, a preferred XA protein comprises the following changes (see FIG. 10B) (SEQ ID NO:7): Y53F, D83V, S84A, W85F, Y105F, R132A, R136L, A142L, I144L, and H149F.

In another preferred embodiment, the XA protein of the invention has a sequence that differs from a wild type *B. circulans* xylanase sequence in at least one amino acid position selected from the positions 53, 66, 68, 81, 83, 84, 101, 105, 132, 136, 138, 142, 144, 149, and 169 (see FIG. 3).

In one aspect of this embodiment, preferred amino acid changes within the 'Region around D83' are as follows (see FIGS. 7A, 8A): Y53F; Y53W; L66F; L68V; L68I; V81A; D83V; D83T; D83A D83E; D83F; S84V; S84A; S84T; S84D; D101N; D101A; D101S; Y105F; R132M; R132; R132A; R132S; R132D; R132E; R136M; R136K; R136L; R136E; R136F; R136E; T138V; T138D; T138L; T1384A; T138S; T138N; T138Hsp; A142L; A142I; A142V; I144L; I144V; I144A; H149F; H149Y; H149Hsp; and M169L. These may be done either individually or in combination, with any combination possible. However, as outlined herein, preferred embodiments utilize at least five, and preferably more variable positions in each XA protein.

In one particularly preferred aspect of this embodiment, a preferred XA protein comprises the following changes (see FIGS. 7B and 8B) (SEQ ID NO:5); Y53F, D83V, S84V, Y105F, R132M, R136M, A142L, I144L, and H149F.

Particularly preferred embodiments where XA proteins have variable positions as compared to *B. circulans* xylanase comprise the 'Helix region', as shown in FIGS. 11–13.

In a preferred embodiment, XA proteins have variable positions selected solely from 'Helix Region' residues of *B. circulans* xylanase. Alternatively, at least a majority (51%) of the variable positions are selected from 'Helix Region' residues, with at least about 75% of the variable positions being preferably selected from 'Helix Region' residue positions, and at least about 90% of the variable positions being particularly preferred. A specifically preferred embodiment has only "Helix Region" variable positions altered as compared to *B. circulans* xylanase.

In one embodiment, the variable 'Helix Region' positions are altered to any of the other 19 amino acids. In a preferred embodiment, the variable core residues are chosen from Ala, Val, Phe, Ile, Leu, Tyr, Trp and Met. In another preferred embodiment, the variable core residues are chosen from Ala, Val, Leu, lie, Phe, Tyr, and Trp plus the original wild type residue. In another embodiment, the variable residues were chosen from boundary rotamers (Ala, Val, Leu, Ile, Phe, Trp, Asp, Asn, Glu, Gin, Lys, Ser, Thr, His, Arg, Met).

In another preferred embodiment, the XA protein of the invention has a sequence that differs from a wild type *B. circulans* xylanase sequence in at least one amino acid position selected from the positions: 70, 72, 77, 79, 81, 95, 96, 98, 100, 101, 102, 103, 105, 107, 109, 128, 130, 132, 144, 146, 147, 148, 149, 150, 152, 153, 156, 157, 158, 160, 161, 164, and 167 (see FIG. 3).

In one aspect of this embodiment, preferred amino acid changes within the 'Helix Region' are as follows (see FIGS. 11A, 12A): I77L; I77V; Y79F; V81I; K95L; K95I; K95E; K95Q; K95V; K95R; K96S; V98T, V98D; V98A; V98E; V98T; V98L; S100V; S100A; G102D; G103I; Y105F;

I107L; T109V; T109I; T109K; T109E; T109Q; T109L; T109D; T109R; Y112SV; Y128I; Y128L; S130A; R132A; I144L; I144V; T147I; T147D; T147E; T147V; T147Q; T147L; T147A; T147K; T147N; T147S N148E; N148Q; N148K; N148R; N148D; N148A; N148L; N148S; H149F; V150I; A152S; A152Y; A152W; A152D; W153F; H156Y, H156F; H156E; H156V; H156I; H156L; H156Q; H156N; H156K; M158I; M158L; M158L; M158V; M158E; L160F; and Q167E. These may be done either individually or in combination, with any combination possible. However, as outlined herein, preferred embodiments utilize at least five, and preferably more variable positions in each XA protein.

In one particularly preferred aspect of this embodiment, a preferred XA protein comprises the following changes (see FIGS. 11B) (SEQ ID NO:8); Y79F, G96S, V98T, S100V, G102D, G103I, Y105F, T109I, Y128V, S130A, R132A, I144L, T147I, N148E, H149F, V150I, A152S, H156Y, M158I,L160G, and Q167E.

In another particularly preferred aspect of this embodiment, a preferred XA protein comprises the following changes (see FIGS. 12B) (SEQ ID NO:9); Y79F, S100V, T109I, Y128V, T147I, N148E, V150I, A152S, H156Y, M158I, L160F, and Q167E.

In another particularly preferred aspect of this embodiment, a preferred XA protein comprises the following changes (see FIGS. 13B) (SEQ ID NO:10); Y79F, G96S, V98T, S1000V, Y105F, T109I, Y128V, S130A; R132M; I144I; T147I, N148E, H149F; A152S, H156Y, M158I, and Q167E.

Particularly preferred embodiments where XA proteins have variable positions as compared to *B. circulans* xylanase comprise the 'Active Site Region', as shown in FIGS. 14 and 15.

In a preferred embodiment, XA proteins have variable positions selected solely from 'Active Site Region' residues of *B. circulans* xylanase. Alternatively, at least a majority (51 %) of the variable positions are selected from 'Active Site Region' residues, with at least about 75% of the variable positions being preferably selected from 'Active Site Region' residue positions, and at least about 90% of the variable positions being particularly preferred. A specifically preferred embodiment has only 'Active Site Region' variable positions altered as compared to *B. circulans* xylanase.

In another preferred embodiment, the XA protein of the invention has a sequence that differs from a wild type *B. circulans* xylanase sequence in at least one amino acid position selected from the positions: 5, 7, 11, 37, 39, 63, 65, 67, 71, 80, 82, 88, 110, 115, 118, 125, 129, 168, and 170, (see FIG. 3).

In one aspect of this embodiment, preferred amino acid changes within the 'Active Site Region' are as follows (see FIG. 14A): Y5W; Y5F; Y5H; Q7E; Q7L; D11I; D11V; D 11M; D11L; D11E; D11Q D11Y; D11F; D11N; D11S; D11A; V37D; V37M; V37S; V374I; V37E; V37A, V37L; G39A; G39S; N63W; N63Q; N63A; N63D; Y65E; Y65L; Y65M; T67E; T67D; T67L; T67A; W71V;W71F; W71M; W71 D; W71 E; W71I; W71S; Y80M; Y80L; Y80F; Y80I; Y80E; V82D; Y88N; Y88K; Y88W; Y88F; Y88Q; Y88D; Y88M; T110 D; A115Y; A15T; A115D; A115S; A115F; I118E; I118D; I118V; I118A; F125Y; F125M; F125L; W129E; W129S; W129L; W129M; V168D; V168A; A170S; A170T, and A170D. These may be done either individually or in combination, with any combination possible. However, as outlined herein, preferred embodiments utilize at least five, and preferably more variable positions in each XA protein.

In one particularly preferred aspect of this embodiment, a preferred XA protein comprises the following changes (see FIG. 14B) (SEQ ID NO:11): Q7E, G39A, N63W, Y65E, T67E, Y88N, T110D, I118E W129E, and V168D.

In another preferred embodiment, the substrate is included in the PDA design of the 'Active site Region'.

In one particularly preferred aspect of this embodiment, a preferred XA protein comprises the following changes (see FIG. 15B) (SEQ ID NO:12): G39S, N63W, Y65E, T67E, Y80M, T110D; W129L, V168D, and A170T.

Any of the above described mutations may be done either individually or in combination, with any combination possible. For example, two mutations selected by the PDA design of the CORE may be combined with 4 mutations selected by the PDA design of the 'Helix Region'.

In a preferred embodiment, the XA proteins of the invention are *B. circulans* xylanase conformers. By "conformer" herein is meant a protein that has a protein backbone 3D structure that is virtually the same but has significant differences in the amino acid side chains. That is, the XA proteins of the invention define a conformer set, wherein all of the proteins of the set share a backbone structure and yet have sequences that differ by at least 3–5%. The three dimensional backbone structure of an XA protein thus substantially corresponds to the three dimensional backbone structure of *B. circulans* xylanase. "Backbone" in this context means the non-side chain atoms: the nitrogen, carbonyl carbon and oxygen, and the α-carbon, and the hydrogens attached to the nitrogen and α-carbon. To be considered a conformer, a protein must have backbone atoms that are no more than 2 Å from the *B. circulans* xylanase structure, with no more than 1.5 Å being preferred, and no more than 1 Å being particularly preferred. In general, these distances may be determined in two ways. In one embodiment, each potential conformer is crystallized and its three dimensional structure determined. Alternatively, as the former is quite tedious, the sequence of each potential conformer is run in the PDA program to determine whether it is a conformer.

XA proteins may also be identified as being encoded by XA nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred.

In a preferred embodiment, an XA nucleic acid encodes an XA protein. As will be appreciated by those in the art, due to the degeneracy of the genetic code, an extremely large number of nucleic acids may be made, all of which encode the XA proteins of the present invention. Thus, having identified a particular amino acid sequence, those skilled in the art could make any number of different nucleic acids, by simply modifying the sequence of one or more codons in a way which does not change the amino acid sequence of the XA.

In one embodiment, the nucleic acid homology is determined through hybridization studies. Thus, for example, nucleic acids which hybridize under high stringency to the nucleic acid sequence shown in FIG. 1 or its complement and encode a XA protein is considered an XA gene.

High stringency conditions are known in the art; see for example Sambrook et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridizabon with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Sambrook wt al, supra; Ausubel et al., supra, and Tijssen, supra.

The XA proteins and nucleic acids of the present invention are recombinant. As used herein, "nucleic acid" may refer to either DNA or RNA, or molecules which contain both deoxy- and ribonucleotdes. The nucleic acids include genomic DNA, cDNA and oligonucleotides including sense and anb-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 1 also includes the complement of the sequence. By the term "recombinant nucleic acid" herein is meant nucleic acid, originally formed in vitro, in general, by the manipulation of nucleic acid by endonucleases, in a form not normally found in nature. Thus an isolated XA nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in as natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an XA protein from one organism in a different organism or host cell. Alternatively, the protein may be made at a significantly higher concentration than is normally seen, through the use of an inducible promoter or high expression promoter, such that the protein is made at increased concentration levels. Furthermore, all of the XA proteins outlined herein are in a form not normally found in nature, as they contain amino acid substitutions, insertions and deletions, with substitutions being preferred, as discussed below.

Also included within the definition of XA proteins of the present invention are amino acid sequence variants of the XA sequences outlined herein and shown in the Figures. That is, the XA proteins may contain additional variable positions as compared to wild type xylanase. These variants fall into one or more of three classes: substitutional, insertional or deletional variants. These variants ordinarily are prepared by site specific mutagenesis of nucleotides in the DNA encoding an XA protein, using cassette or PCR mutagenesis or other techniques well known in the art, to produce DNA encoding the variant, and thereafter expressing the DNA in recombinant cell culture as outlined above. However, variant XA protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the XA protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed XA variants screened for the optimal combination of desired activity. Techniques for making substitution mutations at predetermined sites in DNA having a known sequence are well known, for example, M13 primer mutagenesis and PCR mutagenesis. Screening of the mutants is done using assays of XA protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the XA protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electroposifive side chain, e.g. lysyl, arginyl, or hisbdyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the original XA protein, although variants also are selected to modify the characteristics of the XA proteins as needed. Alternatively, the variant may be designed such that the biological activity of the XA protein is altered. For example, glycosylabon sites may be altered or removed. Similarly, the biological function may be altered; for example, in some instances it may be desirable to have more or less potent xylanase activity.

The XA proteins and nucleic acids of the invention can be made in a number of ways. Individual nucleic acids and proteins can be made as known in the art and outlined below. Alternatively, libraries of XA proteins can be made for testing.

In a preferred embodiment, sets or libraries of XA proteins are generated from a probability distribution table. As outlined herein, there are a variety of methods of generating a probability distribution table, including using PDA, sequence alignments, forcefield calculations such as SCMF calculations, etc. In addition, the probability distribution can be used to generate information entropy scores for each position, as a measure of the mutational frequency observed in the library.

In this embodiment, the frequency of each amino acid residue at each variable position in the list is identified. Frequencies can be thresholded, wherein any variant frequency lower than a cutoff is set to zero. This cutoff is preferably 1%, 2%, 5%, 10% or 20%, with 10% being particularly preferred. These frequencies are then built into the XA protein library. That is, as above, these variable positions are collected and all possible combinations are generated, but the amino acid residues that "fill" the library are utilized on a frequency basis. Thus, in a non-frequency based library, a variable position that has 5 possible residues will have 20% of the proteins comprising that variable position with the first possible residue, 20% with the second, etc. However, in a frequency based library, a variable position that has 5 possible residues with frequencies of 10%, 15%, 25%, 30% and 20%, respectively, will have 10% of the proteins comprising that variable position with the first possible residue, 15% of the proteins with the second residue, 25% with the third, etc. As will be appreciated by those in the art, the actual frequency may depend on the method used to actually generate the proteins; for example, exact frequencies may be possible when the proteins are synthesized. However, when the frequency-based primer system outlined below is used, the actual frequencies at each position will vary, as outlined below.

As will be appreciated by those in the art and outlined herein, probability distribution tables can be generated in a variety of ways. In addition to the methods outlined herein, self-consistent mean field (SCMF) methods can be used in the direct generation of probability tables. SCMF is a deterministic computational method that uses a mean field description of rotamer interactions to calculate energies. A probability table generated in this way can be used to create libraries as described herein. SCMF can be used in three ways: the frequencies of amino acids and rotamers for each amino acid are listed at each position; the probabilities are determined directly from SCMF (see Delarue et la. Pac. Symp. Biocomput. 109–21 (1997), expressly incorporated by reference). In addition, highly variable positions and non-variable positions can be identified. Alternatively, another method is used to determine what sequence is jumped to during a search of sequence space; SCMF is used to obtain an accurate energy for that sequence; this energy is then used to rank it and create a rank-ordered list of sequences (similar to a Monte Carlo sequence list). A probability table showing the frequencies of amino acids at each position can then be calculated from this list (Koehl et al., J. Mol. Biol. 239:249 (1994); Koehl et al., Nat. Struc. Biol. 2:163 (1995); Koehl et al., Curr. Opin. Struct. Biol. 6:222 (1996); Koehl et al., J. Mol. Bio. 293:1183 (1999); Koehl et al., J. Mol. Biol. 293:1161 (1999); Lee J. Mol. Biol. 236:918 (1994); and Vasquez Biopolymers 36:53–70 (1995); all of which are expressly incorporated by reference. Similar methods include, but are not limited to, OPLS-AA (Jorgensen, et al., J. Am. Chem. Soc. (1996), v 118, pp 11225–11236; Jorgensen, W. L.; BOSS, Version 4.1; Yale University: New Haven, Conn. (1999)); OPLS (Jorgensen, et al., J. Am. Chem. Soc. (1988), v 110, pp 1657ff; Jorgensen, et al., J Am. Chem. Soc. (1990), v 112, pp 4768ff); UNRES (United Residue Forcefield; Liwo, et al., Protein Science (1993), v 2, pp1697–1714; Liwo, et al., Protein Science (1993), v 2, pp1715–1731; Liwo, et al., J. Comp. Chem. (1997), v 18, pp849–873; Liwo, et al., J. Comp. Chem. (1997), v 18, pp874–884; Liwo, et al., J. Comp. Chem. (1998), v 19, pp259–276; Forcefield for Protein Structure Prediction (Liwo, et al., Proc. Natl. Acad. Sci. USA (1999), v 96, pp5482–5485); ECEPP/3 (Liwo et al., J Protein Chem 1994 May;13(4):375–80); AMBER 1.1 force field (Weiner, et al., J. Am. Chem. Soc. v 106, pp765–784); AMBER 3.0 force field (U.C. Singh et al., Proc. Natl. Acad. Sci. USA. 82:755–759); CHARMM and CHARMM22 (Brooks, et al., J. Comp. Chem. v4, pp 187–217); cvff3.0 (Dauber-Osguthorpe, et al.,(1988) Proteins: Structure, Function and Genetics, v4, pp3147); cff91 (Maple, et al., J. Comp. Chem. v15, 162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.).

In addition, as outlined herein, a preferred method of generating a probability distribution table is through the use of sequence alignment programs. In addition, the probability table can be obtained by a combination of sequence alignments and computational approaches. For example, one can add amino acids found in the alignment of homologous sequences to the result of the computation. Preferable one can add the wild type amino acid identity to the probability table if it is not found in the computation.

As will be appreciated, an XA protein library created by recombining variable positions and/or residues at the variable position may not be in a rank-ordered list. In some embodiments, the entire list may just be made and tested. Alternatively, in a preferred embodiment, the XA protein library is also in the form of a rank ordered list. This may be done for several reasons, including the size of the library is still too big to generate experimentally, or for predictive purposes. This may be done in several ways. In one embodiment, the library is ranked using the scoring functions of PDA to rank the library members. Alternatively, statistical methods could be used. For example, the library may be ranked by frequency score; that is, proteins containing the most of high frequency residues could be ranked higher, etc. This may be done by adding or multiplying the frequency at each variable position to generate a numerical score. Similarly, the library different positions could be weighted and then the proteins scored; for example, those containing certain residues could be arbitrarily ranked.

In a preferred embodiment, the different protein members of the XA protein library may be chemically synthesized. This is particularly useful when the designed proteins are short, preferably less than 150 amino acids in length, with less than 100 amino acids being preferred, and less than 50 amino acids being particularly preferred, although as is known in the art, longer proteins can be made chemically or enzymatically. See for example Wilken et al, Curr. Opin. Biotechnol. 9:412–26 (1998), hereby expressly incorporated by reference.

In a preferred embodiment, particularly for longer proteins or proteins for which large samples are desired, the library sequences are used to create nucleic acids such as DNA which encode the member sequences and which can then be cloned into host cells, expressed and assayed, if desired. Thus, nucleic acids, and particularly DNA, can be made which encodes each member protein sequence. This is done using well known procedures. The choice of codons, suitable expression vectors and suitable host cells will vary depending on a number of factors, and can be easily optimized as needed.

In a preferred embodiment, multiple PCR reactions with pooled oligonucleotides is done, as is generally depicted in FIG. 17. In this embodiment, overlapping oligonucleotides are synthesized which correspond to the full length gene. Again, these oligonucleotides may represent all of the different amino acids at each variant position or subsets.

In a preferred embodiment, these oligonucleotides are pooled in equal proportions and multiple PCR reactions are performed to create full length sequences containing the combinations of mutations defined by the library. In addition, this may be done using error-prone PCR methods.

In a preferred embodiment, the different oligonucleotides are added in relative amounts corresponding to the probability distribution table. The multiple PCR reactions thus result in full length sequences with the desired combinations of mutations in the desired proportions.

The total number of oligonucleotides needed is a function of the number of positions being mutated and the number of mutations being considered at these posibons:

(number of oligos for constant positions)+$M1+M2+M3+ \ldots Mn$=(total number of oligos required), where $Mn$ is the number of mutations considered at position n in the sequence.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo can contain the codon for a single position being mutated, or for more than one position being mutated. The multiple positions being mutated must be close in sequence to prevent the oligo length from being impractical. For multiple mutating positions on an oligonucleotide, particular combinations of mutations can be included or excluded in the library by including or excluding the oligonucleotide encoding that combination. For example, as discussed herein, there may be correlations between variable regions; that is, when position X is a certain residue, position Y must (or must not) be a particular residue. These sets of variable positions are sometimes referred to herein as a "cluster". When the clusters are comprised of residues close together, and thus can reside on one oligonucleotide primer, the clusters can be set to the "good" correlations, and eliminate the bad combinations that may decrease the effectiveness of the library. However, if the residues of the cluster are far apart in sequence, and thus will reside on different oligonucleotides for synthesis, ft may be desirable to either set the residues to the "good" correlation, or eliminate them as variable residues entirely. In an alternative embodiment, the library may be generated in several steps, so that the cluster mutations only appear together. This procedure, i.e. the procedure of identifying mutation clusters and either placing them on the same oligonucleotides or eliminating them from the library or library generation in several steps preserving clusters, can considerably enrich the experimental library with properly folded protein. Identification of clusters can be carried out by a number of ways, e.g. by using known pattern recognition methods, comparisons of frequencies of occurence of mutations or by using energy analysis of the sequences to be experimentally generated (for example, if the energy of interaction is high, the positions are correlated). These correlations may be positional correlations (e.g. variable positions 1 and 2 always change together or never change together) or sequence correlations (e.g. if there is residue A at position 1, there is always residue B at position 2). See: Pattern discovery in Biomolecular Data: Tools, Techniques, and Applications; edited by Jason T. L. Wang, Bruce A. Shapiro, Dennis Shasha. New York: Oxford University, 1999; Andrews, Harry C. Introduction to mathematical techniques in pattern recognition; New York, Wiley-Interscience [1972]; Applications of Pattern Recognition; Editor, K. S. Fu. Boca Raton, Fla. CRC Press, 1982; Genetic Algorithms for Pattern Recognition; edited by Sankar K. Pal, Paul P. Wang. Boca Raton: CRC Press, c1996; Pandya, Abhijit S., Pattern recognition with neural networks in C++/Abhijit S. Pandya, Robert B. Macy. Boca Raton, Fla.: CRC Press, 1996; Handbook of pattern recognition & computer vision/edited by C. H. Chen, L. F. Pau, P. S. P. Wang. 2nd ed. Singapore; River Edge, N.J.: World Scientific, c1999; Friedman, Introduction to Pattern Recognition: Statistical, Structural, Neural, and Fuzy Logic Approaches; River Edge, N.J.: World Scientfic, c 1999, Series title: Series in machine perception and artificial intelligence; vol. 32; all of which are expressly incorporated by reference. In addition, programs used to search for consensus motifs can be used as well.

In addition, correlations and shuffling can be fixed or optimized by altering the design of the oligonucleotides; that is, by deciding where the oligonucleofides (primers) start and stop (e.g. where the sequences are "cut"). The start and stop sites of oligos can be set to maximize the number of clusters that appear in single oligonucleobdes, thereby enriching the library with higher scoring sequences. Different oligonucleotide start and stop site options can be computationally modeled and ranked according to number of clusters that are represented on single oligos, or the percentage of the resulting sequences consistent with the predicted library of sequences.

The total number of oligonucleotides required increases when multiple mutable positions are encoded by a single oligonucleotide. The annealed regions are the ones that remain constant, i.e. have the sequence of the reference sequence.

Oligonucleotides with insertions or deletions of codons can be used to create a library expressing different length proteins. In particular computational sequence screening for insertions or deletions can result in secondary libraries defining different length proteins, which can be expressed by a library of pooled oligonucleotde of different lengths.

In a preferred embodiment, the XA protein library is done by shuffling the family (e.g. a set of variants); that is, some set of the top sequences (if a rank-ordered list is used) can be shuffled, either with or without error-prone PCR. "Shuffling" in this context means a recombination of related sequences, generally in a random way. It can include "shuffling" as defined and exemplified in U.S. Pat. Nos. 5,830,721; 5,811,238; 5,605,793; 5,837,458 and PCT US/19256, all of which are expressly incorporated by reference in their entirety. This set of sequences can also be an artificial set; for example, from a probability table (for example generated using SCMF) or a Monte Carlo set. Similarly, the "family" can be the top 10 and the bottom 10 sequences, the top 100 sequence, etc. This may also be done using error-prone PCR.

Thus, in a preferred embodiment, in silico shuffling is done using the computational methods described herein. That is, starting with either two libraries or two sequences, random recombinations of the sequences can be generated and evaluated.

In a preferred embodiment, error-prone PCR is done to generate the XA protein library. See U.S. Pat. Nos. 5,605, 793, 5,811,238, and 5,830,721, all of which are hereby incorporated by reference. This can be done on the optimal sequence or on top members of the library, or some other artificial set or family. In this embodiment, the gene for the optimal sequence found in the computational screen of the primary library can be synthesized. Error prone PCR is then performed on the optimal sequence gene in the presence of oligonucleotides that code for the mutations at the variant positions of the library (bias oligonucleotides). The addition of the oligonucleotides will create a bias favoring the incorporation of the mutations in the library. Alternatively, only oligonucleotides for certain mutations may be used to bias the library.

In a preferred embodiment, gene shuffling with error prone PCR can be performed on the gene for the optimal sequence, in the presence of bias oligonucleobdes, to create a DNA sequence library that reflects the proportion of the mutations found in the XA protein library. The choice of the bias oligonucleotdes can be done in a variety of ways; they can be chosen on the basis of their frequency, i.e. oligonucleobdes encoding high mutational frequency positions can be used; alternatively, oligonucleotides containing the most variable positions can be used, such that the diversity is increased; if the secondary library is ranked, some number of top scoring positions can be used to generate bias oligonucleobdes; random positions may be chosen; a few top scoring and a few low scoring ones may be chosen; etc. What is important is to generate new sequences based on preferred variable positions and sequences.

In a preferred embodiment, PCR using a wiud type gene or other gene can be used, as is schematically depicted in FIG. 18. In this embodiment, a starting gene is used; generally, although this is not required, the gene is usually the wild type gene. In some cases it may be the gene encoding the global optimized sequence, or any other sequence of the list, or a consensus sequence obtained e.g. from aligning homologous sequences from different organisms. In this embodiment, oligonucleotides are used that correspond to the variant positions and contain the different amino acids of the library. PCR is done using PCR primers at the termini, as is known in the art. This provides two benefits; the first is that this generally requires fewer oligonucleotides and can result in fewer errors. In addition, it has experimental advantages in that if the wild type gene is used, it need not be synthesized.

In addition, there are several other techniques that can be used, as exemplified in the figures, e.g. FIGS. 19–21. In a preferred embodiment, ligation of PCR products is done.

In a preferred embodiment, a variety of additional steps may be done to the XA protein library; for example, further computational processing can occur, different XA libraries can be recombined, or cutoffs from different libraries can be combined. In a preferred embodiment, an XA protein library may be computationally remanipulated to form an additional XA protein library (sometimes referred to herein as "tertiary libraries"). For example, any of the XA protein library sequences may be chosen for a second round of PDA, by freezing or fixing some or all of the changed positions in the first library. Alternatively, only changes seen in the last probability distribution table are allowed. Alternatively, the stringency of the probability table may be altered, either by increasing or decreasing the cutoff for inclusion. Similarly, the XA protein library may be recombined experimentally after the first round; for example, the best gene/genes from the first screen may be taken and gene assembly redone (using techniques outlined below, multiple PCR, error prone PCR, shuffling, etc.). Alternatively, the fragments from one or more good gene(s) to change probabilities at some positions. This biases the search to an area of sequence space found in the first round of computational and experimental screening.

In a preferred embodiment, a tertiary library can be generated from combining different XA libraries. For example, a probability distribution table from a first XA protein library can be generated and recombined; either computationally or experimentally, as outlined herein. A PDA XA protein library may be combined with a sequence alignment XA protein library, and either recombined (again, computationally or experimentally) or just the cutoffs from each joined to make a new tertiary library. The top sequences from several libraries can be recombined. Sequences from the top of a library can be combined with sequences from the bottom of the library to more broadly sample sequence space, or only sequences distant from the top of the library can be combined. XA libraries that analyzed different parts of a protein can be combined to a tertiary library that treats the combined parts of the protein.

In a preferred embodiment, a tertiary library can be generated using correlations in an XA protein library: That is, a residue at a first variable position may be correlated to a residue at second variable position (or correlated to residues at additional positions as well). For example, two variable positions may sterically or electrostatically interact, such that if the first residue is X, the second residue must be Y. This may be either a positive or negative correlation.

Using the nucleic acids of the present invention which encode an XA protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the XA protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotc cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the XA protein, a replacement of the naturally occurring secretory leader sequence is desired. In this embodiment, an unrelated secretory leader sequence is operably linked to an XA encoding nucleic acid leading to increased protein secretion. Thus, any secretory leader sequence resulting in enhanced secretion of the XA protein, when compared to the secretion of the wild type xylanase and its secretory sequence, is desired. Suitable secretory leader sequences that lead to the secretion of a protein are know in the art.

In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from Bacillus are preferably used to express the fusion protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

The XA nucleic acids are introduced into the cells either alone or in combination with an expression vector. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $(Ca_3PO_4)_2$ precipitation, liposome fusion, lipofectin®, electroporation, viral infection, etc. The XA nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

The XA proteins of the present invention are produced by culturing a host cell transformed with an expression vector containing nucleic acid encoding an XA protein, under the appropriate conditions to induce or cause expression of the XA protein. The conditions appropriate for XA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melanogaster* cells, *Saccharomyces cerevisiae* and other yeasts, *E. coli, Bacillus subtilis*, SF9 cells, C129 cells, 293 cells, Neurospora, BHK, CHO, COS, *Pichia Pastoris*, Aspergillus, Trichoderma, etc.

In a preferred embodiment, XA proteins of the invention are expressed in filamentous fungi. Filamentous fungi are eukaryotic microorganisms and include all filamentous forms of the subdivision Eumycotina. Various species of filamentous fungi may be used as expression hosts, including the following genera: Aspergillus, Trichderma, Neurospora, Podospora, Endothia Mucor, Cochiobolus and Pyricularia. Specific expression hosts include *A. nidulans, A. niger, A. awomari, A. oryzae, N. crassa, Trichoderma reesei*, and *Trichoderma viride*. Suitable vectors and methods for expression and secretion of heterologous polypeptides from filamentous fungi are described in U.S. Pat. No. 6,004,785, hereby expressly incorporated by reference.

In a preferred embodiment, the XA proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleobide(s) in liposomes, and direct microinjecton of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred. Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as hematopoietic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be additionally genetically engineered, that is, contain exogeneous nucleic acid other than the XA nucleic acid.

In a preferred embodiment, the XA proteins are expressed in bacterial systems. Bacterial expression systems are well known in the art. Sung et al. [Protein Expression and Purification 4:200–206 (1993); hereby expressly incorporated by reference] report expression of *B. circulans* in *E.coli*.

A suitable bacterial promoter is any nucleic acid sequence capable of binding bacterial RNA polymerase and initiating the downstream (3') transcription of the coding sequence of the XA protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the XA protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria). For expression in bacteria, usually bacterial secretory leader sequences, operably linked to an XA encoding nucleic acid, are preferred.

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, XA proteins are produced in insect cells. Expression vectors for the transformation of insect cells, and in particular, baculovirus-based expression vectors, are well known in the art.

In a preferred embodiment, XA protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In addition, the XA polypeptides of the invention may be further fused to other proteins, if desired, for example to increase expression or stabilize the protein.

Once made, the XA proteins may be covalently modified. One type of covalent modification includes reacting targeted amino acid residues of an XA polypeptide with an organic derivatizing agent that is capable of reacting with selected side chains or the N- or C-terminal residues of an XA polypeptide. Derivatization with bifunctional agents is useful, for instance, for crosslinking an XA protein to a water-insoluble support matrix or surface for use in the method for purifying anti-XA antibodies or screening 10 assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W. H. Freeman & Co., San Francisco, pp. 79–86 (1983)], acetylation of the N-terminal amine, and amidaton of any C-terminal carboxyl group.

Another type of covalent modification of the XA polypeptide included within the scope of this invention comprises altering the native glycosylation pattern of the polypeptide. "Altering the native glycosylation pattern" is intended for purposes herein to mean deleting one or more carbohydrate moieties found in native sequence XA polypeptide, and/or adding one or more glycosylation sites that are not present in the native sequence XA polypeptide.

Addition of glycosylation sites to XA polypeptides may be accomplished by altering the amino acid sequence thereof. The alteration may be made, for example, by the addition of, or substitution by, one or more serine or threonine residues to the native sequence XA polypeptide (for O-linked glycosylation sites). The XA amino acid sequence may optionally be altered through changes at the DNA level, particularly by mutating the DNA encoding the XA polypeptide at preselected bases such that codons are generated that will translate into the desired amino acids.

Another means of increasing the number of carbohydrate moieties on the XA polypeptide is by chemical or enzymatic coupling of glycosides to the polypeptide. Such methods are described in the art, e.g., in WO 87/05330 published Sep. 11, 1987, and in Aplin and Wriston, CRC Crit. Rev. Biochem., pp. 259–306 (1981).

Removal of carbohydrate moieties present on the XA polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Another type of covalent modification of XA comprises linking the XA polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 15 4,179,337.

XA polypeptides of the present invention may also be modified in a way to form chimeric molecules comprising an XA polypeptide fused to another, heterologous polypeptide or amino acid sequence. In one embodiment, such a chimeric molecule comprises a fusion of an XA polypeptide with a tag polypeptide which provides an epitope to which an anti-tag antibody can selectively bind. The epitope tag is generally placed at the amino-or carboxyl-terminus of the XA polypeptide. The presence of such epitope-tagged forms of an XA polypeptide can be detected using an antibody against the tag polypeptide. Also, provision of the epitope tag enables the XA polypeptide to be readily purified by affinity purification using an anti-tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol. 8:2159–2165 (1988)]; the c-myc tag and the 8F9, 3C7, 6E10, G4, 87 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology 6:1204–1210 (1988)]; the KT3 epitope peptide [Martin et al., Science 255:192–194 (1992)]; tubulin epitope peptide [Skinner et al., J. Biol. Chem. 266:15163–15166 (1991)]; and the T7gene 10 protein peptide tag [Lutz-Freyermuth et al., Proc. Natl. Acad. Sci. U.S.A. 87:6393–6397 (1 990)].

In a preferred embodiment, the XA protein is purified or isolated after expression. XA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the XA protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, New York (1982). The degree of purification necessary will vary depending on the use of the XA protein. In some instances no purification will be necessary.

Once made, the XA proteins and nucleic acids of the invention find use in a number of applications. In a preferred embodiment, the XA proteins are used in pulp bleaching.

In another preferred embodiment, the XA proteins and nucleic acids of the invention are useful in the bioconversion of lignocellulosic materials to fuels.

The XA proteins and nucleic acids of the invention are also useful for clarifying juice and wine [Zeikus et al., ACS Symp. Ser. 460:36–51 (1991); Beily, ACS Symp. Ser. 460:408–416 (1991); Woodward, Top Enzyme Ferment. Biotechnol. 8:9–30 (1984)]; for extracting coffee, plant oils and starch [Beily, supra; Woodward supra; McCleary, Int. J. Biol. Macromol. 8:349–354 (1986)]; for the production of food thickeners (Zeikus et al., supra); for altering texture in bakery products, e.g., improving the quality of dough, help bread rise and processing of wheat and corn for starch production (Maat et al. In Xylans and xylanases, eds. Visseret al., Elsevier Sci pub., Amsterdam. ISBN 0-444-894-772 (1992); McCleary, supra; Krishnarau et al., J. Food Sci. 59:1251–1254 (1994); U.S. Pat. No. 5,306,633); for use as animal food additives to aid in the digestibility of feedstuffs; and in the washing of super precision devices and semiconductors [Takayuki et al., U.S. Pat. No. 5,078,802].

In a preferred embodiment, the invention provides a bleaching agent comprising as an active ingredient an XA proteins of the invention.

The invention further provides methods for bleaching pulp. This method comprises the step of contacting the pulp with a bleaching agent as described herein. In addition to enzymatic treatment using the bleaching agent comprising an XA protein of the invention, the pulp may be bleached as is known in the art by chemicals and/or alkaline extraction before, after or during the enzymatic treatment. Bleaching chemicals are known in the art and include, but are not limited to chlorine, chlorine dioxide, nitrogen dioxide, hypochlorites, hydrogen, oxygen peroxide, ozone, etc.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLE 1

Design and Characterization of Novel XA Proteins by PDA

Summary: Sequences for novel thermostable, thermophilic and/or alkaliphilic xylanase activity (XA) proteins were designed by optimizing (i) residues in the core of the protein, (ii) residues around D83, (iii) residues around the helix region, and (iv) residues around the active site region using Protein Design Automation (PDA) as described in WO98/47089, U.S. Ser. Nos. 09/058,459, 09/127,926, 60/104,612, 60/158,700, 09/419,351, 60/181,630, 60/186,904, 60/132, 475, 60/133,714, U.S. patent application, entitled Protein Design Automation For Protein Libraries (Filed: Apr. 14, 2000; Inventor: Bassil Dahiyat), and PCT US98/07254, all of which are expressly incorporated by reference in their entirety. Several core designs were completed, with 15–33 residues considered corresponding to $20^{15}$–$20^{33}$ sequence possibilities. Residues unexposed to solvent were designed in order to minimize changes to the molecular surface and to limit the potential for antigenicity of designed novel protein analogues.

Calculations required from 12–67 hours on 16 Silicon Graphics R10000 CPU's. The global optimum sequence from each design was selected for characterization. From 3–27 residues were changed from *Bacillus circulans* xylanase in the designed proteins, out of 185 residues total (mature protein).

COMPUTATIONAL PROTOCOLS

Template Structure Preparation:

For this study the crystal structure of *Bacillus circulans* xylanase as deposited in the PDB data bank was used [PDB record 1XNB; Campbell et al., in Suominen and Geinikainen, eds. Proceedings of the second *TRICEL symposium* on *Trichderma reesei* cellulases and other *hydrolases*, Espoo, Finland, Helsinki: Foundation for Biotechnological and Industrial Fermentation Research, pp 63–77 (1993)]. For the PDA design with the substrate, the PDA structure 1BCX was used [Wakarchuk et al., Protein Sci. 3:467–475 (1994)]. In the PDA design the mutated position E172C of the PDB structure was forced back to be the wild type glutamate. After removing all water molecules and the sulfate anion and adding all hydrogen atoms to the protein, this resulting structure was minimized for 50 steps with a conjugate gradient method within the Dreiding forcefield without using coulombic forces.

Design strategies:

Core residues, residues around D83, residues around the helix region, and residues around the active site region were selected for design since optimization of these positions can improve stability, although stabilization has been obtained from modifications at other sites as well. Thus, the complete *Bacillus circulans* xylanase was divided into three different regions called 'CORE', 'D83 Region', 'Helix Region', and 'Active Site' by visually inspecting the three dimensional structure. PDA calculations were run on (i) one set of selected core positions, (ii) two sets of selected 'D83 Region' positions with a total of 6 different designs, (iii) on two sets of selected 'Helix region' positions with a total of 3 different designs, (iv) one set of 'Active Site' positions with a total of 2 designs, one with and one without a substrate (see FIG. 3) with the purpose to create a thermostable, thermophilic, and/or alkaliphilic xylanase.

PDA Calculations

All PDA calculations were performed with solvabon model 2. Solvation model 2 is the solvation model described by Street and Mayo [Fold. Design 3:253–258 (1998)]. If possible, Dead End Elimination (DEE) was run to completion to find the PDA ground state. This was done for the PDA calculations for the CORE, the '83 Region' the 'Helix Region', and the 'Active Site', as defined below.

The DEE calculation was for all the given PDA calculation followed by Monte Carlo (MC) minimization and a list of the 1000 lowest energy sequences was generated. In the case of the 'Active Site' design, a Monte Carlo list of 10,000 sequences was generated.

The PDA calculations for all the designs were run using the a2h1 p0 rotamer library. This library is based on the backbone-dependent rotamer library of Dunbrack and Karplus (Dunbrack and Karplus, J. Mol. Biol. 230(2):543–74 (1993); hereby expressly incorporated by reference) but includes more rotamers for the aromatic and hydrophobic amino acids; $X_1$ and $X_2$ angle values of rotamers for all the aromatic amino acids and $X_1$ angle values for all the other hydrophobic amino acids were expanded ±1 standard deviation about the mean value reported in the Dunbrack and Karplus library. Unless explicitly stated, typical PDA parameters were used: the van der Waals scale factor was set to 0.9, the H-bond potential well-depth was set to 8.0 kcal/mol, the solvation potential was calculated using type 2 solvation with a nonpolar burial energy of 0.048 kcal/mol and a nonpolar exposure multiplication factor of 1.6, and the secondary structure scale factor was set to 0.0 (secondary structure propensities were not considered). Calculations required from 12–67 hours on 16 Silicon Graphics R10000 CPU's.

Monte Carlo Analysis

Monte Carlo analysis of the sequences produced by PDA calculations shows the ground state (optimal) amino acid and amino acids allowed for each variable position and their frequencies of occurrence (see FIGS. 4 through 15).

EXAMPLE 2

PDA Calculations for the *Bacillus circulans* Xylanase CORE Region

By visual inspection, the following residues were identified as belonging to the CORE of *Bacillus circulans* xylanase: Y26, V28, W30, F36, V38, I51, Y53, A55, W58, G62, G64, L66, L68, G70, T72, I77, Y79, V81, Y105, I107, S130, A142, I144, F146, W153, M169, T171, G173, S176, G178, S180, V182, and V184 (see FIG. 2A).

Thus, the following positions were included in the PDA design (see also FIG. 3):

```
26  28  30  36  38  51  53  55  58  62  64  66
Tyr Val Trp Phe Val Ile Tyr Ala Trp Gly Gly Leu 68  70  72  77  79  81  105 107 130 142 144 146
Leu Gly Thr Ile Tyr Val Tyr Ile Ser Ala Ile Phe 153 169 171 173 176 178 180 182 184
Trp Met Thr Gly Ser Gly Ser Val Val
```

A rotamer group was assigned to each CORE position which allows this position to become any phobic residue with the exception of methionine (i.e., Ala, Val, Leu, Ile, Phe, Tyr, and Trp) plus the original wild type residue. Thus, e.g., the group PHOB_NO_MET+G was assigned to G62, PHOB_NO_MET+T to T72, and PHOB_NO_MET+M to M169.

In the following PDA design only the CORE residues were allowed to mutate to any amino acid rotamer restricted by the definition of the rotamer group assigned to this position. The rest of the protein was treated as a template, with fixed coordinates. An energy cutoff of 50 kcal/mol for the rotamer/template energy was used to exclude unfavorable rotamers. The van der Waals radius was scaled by a factor of 0.9 and the solvation model 2 as defined by Street and Mayo (supra) was used. The ground state rotamer sequence was extracted from all the possible rotamer sequences using the Dead End Elimination (DEE) method. To check for other low energy sequences a Monte Carlo (MC) search was performed starting from the DEE ground state.

The PDA calculation resulted in the following ground state sequence (SEQ ID NO:3):

```
26  28  30  36  38  51  53  55  58  62  64  66
Phe Ile Phe Phe Val Ile Phe Ala Phe Gly Val Leu 68  70  72  77  79  81  105 107 130 142 144 146
Leu Gly Thr Ile Phe Val Phe Ile Ser Leu Ile Phe 153 169 171 173 176 178 180 182 184
Trp Met Leu Gly Ala Gly Ala Ile Val
```

This sequence shows 13 mutations when compared to the wild type *Bacillus circulans* xylanase sequence, Y26F, V28I, W30F, Y53F, W58F, G64V, Y79F, Y105F, A142L, T171L, S176A, S180A, and V182I (see FIG. 4B) (SEQ ID NO:3). This state shows 93% identity with the complete wild type *Bacillus circulans* xylanase sequence and has 60% identity in the designed positions with the wild type sequence.

Using the Monte Carlo technique a list of low energy sequences was generated. The analysis of the lowest 1000 protein sequences generated by Monte Carlo leads to the mutation pattern shown in FIG. 4A. Out of the lowest 1000 sequences none has more than 20 mutations from the wild type sequence and out of the lowest 101 sequences none has more than 18 mutations. Thus, any protein sequence showing mutations at the positions according to FIG. 4A will potentially generate a more stable and/or active XA protein. In particular those protein sequences found among the list of the lowest 101 MC generated sequences (data not shown) have a high potential to result in a more stable and active XA protein. A preferred XA sequence is shown in FIG. 4B (SEQ ID NO:3). A DNA library can be generated to mirror the probability table of FIG. 4A that comprises at least one sequence that is more stable and/or active than wild type *Bacillus circulans* xylanase.

EXAMPLE 3

PDA Calculations for the *Bacillus circulans* Xylanase Region Around D83 (a)

Buried polar residues are known targets that create more stable proteins when mutated to hydrophobic residues as has been shown for the arc repressor protein [Hendsch et al., Biochemistry 35:7621–7625 (1996)]. D83 in *Bacillus circulans* xylanase is such a buried polar residue. PDA was used to design the region around this position (see FIG. 2B). All amino acid residues having heavy side chain atoms within a distance of 7 Å from any heavy side chain atom of D83 that is: Y53, L66, T67, L68, V81, V82, D83, S84, W85, D101, Y105, R132, R136, T138, A142, I144, H149, and M169, were included in the calculation. Of these residues Y53, L66, L68, V81, Y105, A142, I144, H149, and M169, were defined as CORE positions and T67, V82, D83, S84, W85, D101, R132, R136, T138 as BOUNDARY positions. A rotamer group consisting of the phobic residues without methionine (Ala, Val, Leu, Ile, Phe, Tyr, Trp) plus the wild type amino acid was assigned to the CORE positions. To D83, R132, and R136 the boundary rotamers (Ala, Val, Leu, Ile, Phe, Trp, Asp, Asn, Glu, Gln, Lys, Ser, Thr, His, Arg, Met) were assigned and to T67, V82, S84, W85, D101, T138 THE BOUNDARY ROTAMERS WITHOUT METHION- INE. The rest of the protein was treated as a fixed template. In the PDA calculation an energy cutoff of 50 kcal/mol was used for the rotamer/template energy to exclude unfavorable rotamers. The van der Waals radius was scaled by a factor of 0.9 and the solvation model 2 as defined by Street and Mayo (supra) was used. The ground state rotamer sequence was extracted from all the possible rotamer sequences using the Dead End Elimination (DEE) method. To check for other low energy sequences a Monte Carlo (MC) search was performed starting from the DEE ground state.

Thus, the following positions were included in the PDA design (see also FIG. 3):

```
 53  66  67  68  81  82  83  84  85 101 105 132
Tyr Leu Thr Leu Val Val Asp Ser Trp Asp Tyr Arg 136 138 142 144 149 169
Arg Thr Ala Ile His Met
```

The PDA calculation resulted in the following ground state sequence (SEQ ID NO:4):

```
 53  66  67  68  81  82  83  84  85 101 105 132
Phe Leu Thr Leu Val Val Val Val Phe Asp Phe Met 136 138 142 144 149 169
Met Thr Leu Leu Phe Met
```

This sequence shows 10 mutations when compared to the wild type Bacillus circulans xylanase sequence, Y53F, D83V, S84V, W85F, Y105F, R132M, R136M, A142L, I144L, and H149F (see FIG. 5B) (SEQ ID NO:4). This DEE ground state shows 95% identity with the complete wild type Bacillus circulans xylanase sequence and has 44% identity in the designed positions with the wild type sequence.

Using the Monte Carlo technique a list of low energy sequences was generated. The analysis of the lowest 1000 protein sequences generated by Monte Carlo leads to the mutation pattern shown in FIG. 5A. Out of the lowest 1000 sequences none has more than 14 mutations from the wild type sequence and out of the lowest 101 sequences none has more than 13 mutations. Thus, any protein sequence showing mutations at the positions according to FIG. 5A will potentially generate a more stable and/or active XA protein. In particular those protein sequences found among the list of the lowest 101 MC generated sequences (data not shown) have a high potential to result in a more stable and active XA protein. A preferred XA sequence is shown in FIG. 5B (SEQ ID NO:4). A DNA library can be generated to mirror the probability table of FIG. 5A that comprises at least one sequence that is more stable and/or active than wild type Bacillus circulans xylanase.

PDA Calculations for the *Bacillus circulans* Xylanase Region Around D83 (b)

A similar calculation as above was performed where D83 was considered a CORE residue, but was still allowed to change its identity to all rotamers of the boundary group.

The PDA calculation resulted in the following ground state sequence, which is identical to the one obtained above in (a) (SEQ ID NO:4):

```
 53  66  67  68  81  82  83  84  85 101 105 132
Phe Leu Thr Leu Val Val Val Val Phe Asp Phe Met
```

-continued

```
136 138 142 144 149 169
Met Thr Leu Leu Phe Met
```

Using the Monte Carlo technique a list of low energy sequences was generated. The analysis of the lowest 1000 protein sequences generated by Monte Carlo leads to the mutation pattern shown in FIG. 6A. This pattern is slightly different from the one shown in FIG. 5A. Out of the lowest 1000 sequences none has more than 13 mutations from the wild type sequence and out of the lowest 101 sequences none has more than 13 mutations. Thus, any protein sequence showing mutations at the positions according to FIG. 6A will potentially generate a more stable and/or active XA protein. In particular those protein sequences found among the list of the lowest 101 MC generated sequences (data not shown) have a high potential to result in a more stable and/or active XA protein. A preferred XA sequence is shown in FIG. 6B (SEQ ID NO:4). A DNA library can be generated to mirror the probability table of FIG. 6A that comprises at least one sequence that is more stable and/or active than wild type *Bacillus circulans* xylanase.

PDA Calculations for the *Bacillus circulans* Xylanase Region Around D83 (c)

A similar calculation as above was performed where T67, V82, W85, which have side chains pointing away from th D83 side chain, were excluded and D83 was considered as a BOUNDARY residue (see FIG. 3).

The PDA calculation resulted in the following ground state sequence (SEQ ID NO:5):

```
 53  66  68  81  83  84 101 105 132 136 138 142
Phe Leu Leu Val Val Val Asp Phe Met Met Thr Leu 144 149 169
Leu Phe Met
```

This sequence shows 9 mutations when compared to the wild type *Bacillus circulans* xylanase sequence, Y53F, D83V, S84V, Y105F, R132M, R136M, A142L, I144L, and H149F (see FIG. 7B) (SEQ ID NO:5). This DEE ground state shows 95% identity with the complete wild type *Bacillus circulans* xylanase sequence and has 40% identity in the designed positions with the wild type sequence.

Using the Monte Carlo technique a list of low energy sequences was generated. The analysis of the lowest 1000 protein sequences generated by Monte Carlo leads to the mutation pattern shown in FIG. 7A. Out of the lowest 1000 sequences none has more than 12 mutations from the wild type sequence and out of the lowest 101 sequences none has more than 12 mutations. Thus, any protein sequence showing mutations at the positions according to FIG. 7A will potentially generate a more stable and/or active XA protein. In particular those protein sequences found among the list of the lowest 101 MC generated sequences (data not shown) have a high potential to result in a more stable and/or active XA protein. A preferred XA sequence is shown in FIG. 7B (SEQ ID NO:5). A DNA library can be generated to mirror the probability table of FIG. 7A that comprises at least one sequence that is more stable and/or active than wild type *Bacillus circulans* xylanase.

PDA Calculations for the *Bacillus circulans* Xylanase Region Around D83 (d)

A similar calculation as above was performed where T67, V82, W85, were excluded and D83 was considered as a CORE residue, but was still allowed to change its identity to all rotamers of the boundary group (see FIG. 3).

The PDA calculation resulted in the following ground state sequence, which is identical to the one obtained above in (c) (SEQ ID NO:5):

```
53  66  68  81  83  84  101 105 132 136 138 142
Phe Leu Leu Val Val Val Asp Phe Met Met Thr Leu 144 149 169
Leu Phe Met
```

Using the Monte Carlo technique a list of low energy sequences was generated. The analysis of the lowest 1000 protein sequences generated by Monte Carlo leads to the mutation pattern shown in FIG. 8A. This pattern is slightly different from the one shown in FIG. 7A. Out of the lowest 1000 sequences none has more than 12 mutations from the wild type sequence and out of the lowest 101 sequences none has more than 12 mutations. Thus, any protein sequence showing mutations at the positions according to FIG. 8A will potentially generate a more stable and/or active XA protein. In particular those protein sequences found among the list of the lowest 101 MC generated sequences (data not shown) have a high potential to result in a more stable and/or active XA protein. A preferred XA sequence is shown in FIG. 8B (SEQ ID NO:5). A DNA library can be generated to mirror the probability table of FIG. 8A that comprises at least one sequence that is more stable and/or active than wild type *Bacillus circulans* xylanase.

PDA Calculations for the *Bacillus circulans* Xylanase Region Around D83 (e)

A similar calculation as above was performed where the boundary rotamer group without methionine was used for R132 AND R136 and D83 was considered as a BOUNDARY residue (see FIG. 3).

The PDA calculation resulted in the following ground state sequence (SEQ ID NO:6):

```
53  66  67  68  81  82  83  84  85  101 105 132
Phe Leu Thr Leu Val Val Val Val Phe Asp Phe Ala 136 138 142 144 149 169
Leu Thr Leu Leu Phe Met
```

This sequence shows 10 mutations when compared to the wild type *Bacillus circulans* xylanase sequence, Y53F, D83V, S84V, W85F, Y105F, R132A, R136L, A142L, I144L, and H149F (see 9B) (SEQ ID NO:6). This DEE ground state shows 95% identity with the complete wild type *Bacillus circulans* xylanase sequence and has 40% identity in the designed positions with the wild type sequence.

Using the Monte Carlo technique a list of low energy sequences was generate/d. The analysis of the lowest 1000 protein sequences generated by Monte Carlo leads to the mutation pattern shown in FIG. 9A. Out of the lowest 1000 sequences none has more than 13 mutations from the wild type sequence and out of the lowest 101 sequences none has more than 13 mutations. Thus, any protein sequence showing mutations at the positions according to FIG. 9A will potentially generate a more lowest 101 MC generated sequences (data not shown) have a high potential to result in a more stable and/or active XA protein. A preferred XA sequence is shown in FIG. 9B (SEQ ID NO:6). A DNA library can be generated to mirror the probability table of FIG. 9A that comprises at least one sequence that is more stable and/or active than wild type *Bacillus circulans* xylanase.

PDA Calculations for the *Bacillus circulans* Xylanase Region Around D83 (f)

A similar calculation as above(e) was performed where the boundary rotamer group without methionine was used for R132 AND R136 and D83 was considered as a CORE residue, but was still allowed to change its identity to all rotamers of the boundary group (see FIG. 3).

The PDA calculation resulted in the following ground state sequence (SEQ ID NO:7):

```
53  66  67  68  81  82  83  84  85  101 105 132
Phe Leu Thr Leu Val Val Val Ala Phe Asp Phe Ala 136 138 142 144 149 169
Leu Thr Leu Leu Phe Met
```

This sequence shows 10 mutations when compared to the wild type *Bacillus circulans* xylanase sequence, Y53F, D83V, S84A, W85F, Y105F, R132A, R136L, A142L, I144L, and H149F (see FIG. 10B) (SEQ ID NO:7). This DEE ground state shows 95% identity with the complete wild type *Bacillus circulans* xylanase sequence and has 40% identity in the designed positions with the wild type sequence.

Using the Monte Carlo technique a list of low energy sequences was generated. The analysis of the lowest 1000 protein sequences generated by Monte Carlo leads to the mutation pattern shown in FIG. 10A. Out of the lowest 1000 sequences none has more than 13 mutations from the wild type sequence and out of the lowest 101 sequences none has more than 13 mutations. Thus, any protein sequence showing mutations at the positions according to FIG. 10A will potentially generate a more stable and/or active XA protein. In particular those protein sequences found among the list of the lowest 101 MC generated sequences (data not shown) have a high potential to result in a more stable and/or active XA protein. A preferred XA sequence is shown in FIG. 10B (SEQ ID NO:7). A DNA library can be generated to mirror the probability table of FIG. 10A that comprises at least one sequence that is more stable and/or active than wild type *Bacillus circulans* xylanase.

Both (c) and (d) or (e) and (f) show that the ground state sequence is nearly independent of D83 being a CORE or BOUNDARY residue.

EXAMPLE 4

PDA Calculations for the *Bacillus circulans* Xylanase Helix Region (a)

Another region offering potential for higher thermostability and alkaline activity is the region around the helix (residue T147 to K154) in the *Bacillus circulans* xylanase. The following residues were included in the PDA calculation: G70, T72, I77, Y79, V81, K95, G96, V98, S100, D101, G102, G103, Y105, I107, T109, Y128, S130, R132, I144, F146, T147, N148, H149, V150, A152, W153,H156, G157, M158, L160, G161, W164, and Q167 (see FIG. 2C). Residues G70, T72, I77, Y79, V81, S100, Y105, I107, Y128, S130, I144, F146, H149, V150, and W153 were treated as CORE positions and residues K95, G96, V98, D101, G102, G103, T109, R132, T147, N148, A152, H156,G157, M158, L160, G161, W164, and Q167 as BOUNDARY positions. The rest of the protein was treated as a fixed template.

Rotamer groups that include all phobic amino acids except methionine (Ala, Val, Leu, Ile, Phe, Tyr, Trp) plus the wild type residue were assigned to the CORE positions.

H149 was allowed to change to Ala, Val, Leu, Ile, Phe, Tyr, Trp, His, and Ser. The rotamer group containing boundary residues (Ala, Val, leu, Ile, Phe, Tyr, Trp, Asp, Asn, Glu, Gln, Lys, Ser, Thr, His, Arg, Met) was assigned to positions R132 and M158; and the rotamer group containing all boundary residues except methionine was assigned to positions K95, V98, D101, T109, T147, N148, A152, H156, L160, W164, and Q167; the rotamer group containing all boundary residues except methionine but plus glycine was used for the glycine boundary residues.

In the PDA calculation an energy cutoff of 20 kcal/mol was used for the rotamer/template energy to exclude unfavorable rotamers. The van der Waals radius was scaled by a factor of 0.9 and the solvation model 2 as defined by Street and Mayo (supra) was used. The DEE method was employed to extract the ground state rotamer sequence from all the possible rotamer sequences. In those cases where DEE could not extract a single sequence, a Monte Carlo (MC) search was performed starting from the point where DEE stopped.

Thus, the following positions were included in the PDA design (see also FIG. 3):

```
 70  72  77  79  81  95  96  98 100 101 102 103
Gly Thr Ile Tyr Val Lys Gly Val Ser Asp Gly Gly 105 107 109 128 130 132 144 146 147 148 149 150
Tyr Ile Thr Tyr Ser Arg Ile Phe Thr Asn His Val 152 153 156 157 158 160 161 164 167
Ala Trp His Gly Met Leu Gly Trp Gln
```

The PDA calculation resulted in the following ground state sequence (SEQ ID NO:8):

```
 70  72  77  79  81  95  96  98 100 101 102 103
Gly Thr Ile Phe Val Lys Ser Thr Val Asp Asp Ile 105 107 109 128 130 132 144 146 147 148 149 150
Phe Ile Ile Val Ala Ala Leu Phe Ile Glu Phe Ile 152 153 156 157 158 160 161 164 167
Ser Trp Tyr Gly Ile Phe Gly Trp Glu
```

This sequence shows 21 mutations when compared to the wild type *Bacillus circulans* xylanase sequence, Y79F, G96S, V98T, S100V, G102D, G103I, Y105F, T109I, Y128V, S130A, R132A, I144L, T147I, N148E, H149F, V150I, A152S, H156Y, M158I, L160F, and Q167E (see FIG. 11B) (SEQ ID NO:8). This DEE ground state shows 89% identity with the complete wild type *Bacillus circulans* xylanase sequence and has 36% identity in the designed positions with the wild type sequence.

Using the Monte Carlo technique a list of low energy sequences was generated. The analysis of the lowest 1000 protein sequences generated by Monte Carlo leads to the mutation pattern shown in FIG. 11A. Out of the lowest 1000 sequences none has more than 23 mutations from the wild type sequence and out of the lowest 101 sequences none has more than 22 mutations. Thus, any protein sequence showing mutations at the positions according to FIG. 11A will potentially generate a more stable and/or active XA protein. In particular those protein sequences found among the list of the lowest 101 MC generated sequences (data not shown) have a high potential to result in a more stable and/or active XA protein. A preferred XA sequence is shown in FIG. 11B (SEQ ID NO:8). A DNA library can be generated to mirror the probability table of FIG. 11A that comprises at least one sequence that is more stable and/or active than wild type *Bacillus circulans* xylanase.

PDA Calculations for the *Bacillus circulans* Xylanase Helix Region (b)

A similar calculation as above (a) was performed for the helix region where the residues G70, G96, G103, Y105, S130, R132, H149, W153, and G157, which are conserved over family 11 xylanases, are assigned to the rotamer group WILD TYPE and kept in the CORE and BOUNDARY region.

The PDA calculation resulted in the following ground state sequence (SEQ ID NO:9):

```
 70  72  77  79  81  95  96  98 100 101 102 103
Gly Thr Ile Phe Val Lys Gly Val Val Asp Gly Gly 105 107 109 128 130 132 144 146 147 148 149 150
Tyr Ile Ile Val Ser Arg Ile Phe Ile Glu His Ile 152 153 156 157 158 160 161 164 167
Ser Trp Tyr Gly Ile Phe Gly Trp Glu
```

This sequence shows 12 mutations when compared to the wild type *Bacillus circulans* xylanase sequence, Y79F, S100V, T109I, Y128V, T147I, N148E, V150I, A152S, H156Y, M158I, L160F, and Q167E (see FIG. 12B) (SEQ ID NO:9). This DEE ground state shows 94% identity with the complete wild type *Bacillus circulans* xylanase sequence and has 50% identity in the designed positions with the wild type sequence.

Using the Monte Carlo technique a list of low energy sequences was generated. The analysis of the lowest 1000 protein sequences generated by Monte Carlo leads to the mutation pattern shown in FIG. 12A. Out of the lowest 1000 sequences none has more than 15 mutations from the wild type sequence and out of the lowest 101 sequences none has more than 13 mutations. Thus, any protein sequence showing mutations at the positions according to FIG. 12A will potentially generate a more stable and/or active XA protein. In particular those protein sequences found among the list of the lowest 101 MC generated sequences (data not shown) have a high potential to result in a more stable and/or active XA protein. A preferred XA sequence is shown in FIG. 12B (SEQ ID NO:9). A DNA library can be generated to mirror the probability table of FIG. 12A that comprises at least one sequence that is more stable and/or active than wild type *Bacillus circulans* xylanase.

PDA Calculations for the *Bacillus circulans* Xylanase Helix Region (c)

A similar calculation as above (a) residue F160 was not allowed to become any aromatic residue (Phe, Trp, Tyr, His) nor methionine and the two glycine at positions 102 and 103 were excluded from the design.

Thus, the following positions were included in the PDA design (see also FIG. 3):

```
 70  72  77  79  81  95  96  98 100 101 105 107
Gly Thr Ile Tyr Val Lys Gly Val Ser Asp Tyr Ile 109 128 130 132 144 146 147 148 149 150 152 153
Thr Tyr Ser Arg Ile Phe Thr Asn His Val Ala Trp
```

-continued

```
156 157 158 160 161 164 167
His Gly Met Leu Gly Trp Gln
```

The PDA calculation resulted in the following ground state sequence (SEQ ID NO:10):

```
 70  72  77  79  81  95  96  98 100 101 105 107
Gly Thr Ile Phe Val Lys Ser Thr Val Asp Phe Ile 109 128 130 132 144 146 147 148 149 150 152 153
Ile Val Ala Met Leu Phe Ile Glu Phe Val Ser Trp 156 157 158 160 161 164 167
Tyr Gly Ile Leu Gly Trp Glu
```

This sequence shows 17 mutations when compared to the wild type *Bacillus circulans* xylanase sequence, Y79F, G96S, V98T, S100V, Y105F, T109I, Y128V, S130A, R132M, I144L, T147I, N148E, H149F, A152S, H156Y, M158I, and Q167E (see FIG. 13B) (SEQ ID NO:10). This DEE ground state shows 91% identity with the complete wild type *Bacillus circulans* xylanase sequence and has 45% identity in the designed positions with the wild type sequence.

Using the Monte Carlo technique a list of low energy sequences was generated. The analysis of the lowest 1000 protein sequences generated by Monte Carlo leads to the mutation pattern shown in FIG. 13A. Out of the lowest 1000 sequences none has more than 20 mutations from the wild type sequence and out of the lowest 101 sequences none has more than 19 mutations. Thus, any protein sequence showing mutations at the positions according to FIG. 13A will potentially generate a more stable and/or active XA protein. In particular those protein sequences found among the list of the lowest 101 MC generated sequences (data not shown) have a high potential to result in a more stable and/or active XA protein. A preferred XA sequence is shown in FIG. 13B (SEQ ID NO:10). A DNA library can be generated to mirror the probability table of FIG. 13A that comprises at least one sequence that is more stable and/or active than wild type *Bacillus circulans* xylanase.

EXAMPLE 5

PDA Calculations for the *Bacillus circulans* Xylanase Active Site Region (a)

To demonstrate that computational pre-screening is feasible and will lead to a significant reduction in the number of sequences that have to be experimentally screened, initial calculations for the *B. circulans* xylanase with and without the substrate were performed. The PDB structure 1XNB of *B. circulans* xylanase and 1BCX for the enzyme substrate complex were used. 27 residues inside the binding site were visually identified as belonging to the active site. These 27 residues are Y5, Q7, Y9, D11, N35, V37, G39, D63, Y65, T67, Y69, W71, E78, Y80, V82, Y88, T110, R112, A115, I118, F125, Q127, W129Y166, V168, A170, E172. 8 of these residues were regarded as absolutely essential for the enzymatic activity. These eight residues are Y9, N35, Y69, E78, R112, Q127, Y166, and E172. These positions were treated as wild type residues, which means that their conformation was allowed to change but not their amino acid identity.

Three of the 20 naturally occurring amino acids were not considered (cysteine, proline, and glycine). Therefore, 17 different amino acids were still possible at the remaining 19 positions; the problem yields $17^{19}=2.4\times10^{23}$ different amino acid sequences. This number is 10 orders of magnitude larger than what can be handled by state of the art directed evolution methods. Clearly these approaches cannot be used to screen the complete dimensionality of the problem and consider all sequences with multiple substitutions. Therefore PDA calculations were performed to reduce the search space.

Thus, the following positions were included in the PDA design (see also FIG. 3):

```
 5   7  11  37  39  63  65  67  71  80  82  88
Tyr Gln Asp Val Gly Asp Tyr Thr Trp Tyr Val Tyr 110 115 118 125 129 168 170
Thr Ala Ile Phe Trp Val Ala
```

The PDA calculation resulted in the following ground state sequence (SEQ ID NO:11):

```
 5   7  11  37  39  63  65  67  71  80  82  88
Trp Glu Ile Asp Ala Trp Glu Glu Trp Leu Val Asn 110 115 118 125 129 168 170
Asp Tyr Glu Met Ser Asp Ala
```

This sequence shows 15 mutations when compared to the wild type *Bacillus circulans* xylanase sequence, Y5W, Q7E, D11I, V37D, G39A, N63W, Y65E, T67E, Y80L, T110D, A115Y, I118E, F125M, W129S, and V168D (see FIG. 14B) (SEQ ID NO:11).

Using the Monte Carlo technique a list of low energy sequences was generated. The analysis of the lowest 10,000 protein sequences generated by Monte Carlo leads to the mutation pattern shown in FIG. 14A. Thus, any protein sequence showing mutations at the positions according to FIG. 14A will potentially generate a more stable and/or active XA protein. In particular those protein sequences found among the list of the lowest 101 MC generated sequences (data not shown) have a high potential to result in a more stable and/or active XA protein. A preferred XA sequence is shown in FIG. 14B (SEQ ID NO:1 1). A DNA library can be generated to mirror the probability table of FIG. 14A that comprises at least one sequence that is more stable and/or active than wild type *Bacillus circulans* xylanase.

Secondary Library Generation of a Xylanase

If we consider all the amino acids obtained from the PDA calculation (see above), including those with probabilities less than 1%, we obtain $4.1\times10^{15}$ different amino acid sequences. This is a reduction by 7 orders of magnitude. If one only considers those amino acids that have at least a probability of more than 1% as shown in FIG. 14A (1% criterion), the problem is decreased to $3.3\times10^9$ sequences. If one neglects all amino acids with a probability of less than 5% (5% criterion) there are only $4.0\times10^6$ sequences left. This is a number that can be easily handled by screening and gene shuffling techniques. Increasing the list of low energy sequences to 100,000 does not change these numbers significantly and the effect on the amino acids obtained at each position is negligible.

PDA Calculations for the *Bacillus circulans* xylanase with Active Site Region with Substrate (b)

For the PDA design with the substrate the PDB structure 1BCX was used (Wakarchuk et al., supra). In the PDA design the mutated position E172C of the PDB structure was forced back to the wild type glutamate.

The PDA calculation resulted in the following ground state sequence (SEQ ID NO:12):

```
  5   7  11  37  39  63  65  67  71  80  82  88
Tyr Gln Asp Asp Ser Trp Glu Glu Trp Met Val Trp 110 115 118 125 129 168 170
Asp Asp Ile Phe Leu Asp Thr
```

This sequence shows 12 mutations when compared to the wild type *Bacillus circulans* xylanase sequence, V37D, G39S, N63W, Y65E, T67E, Y80M, Y88W, T110D, A115D, W129L, V168D, and A170T (see FIG. 15B) (SEQ ID NO:12).

Using the Monte Carlo technique a list of low energy sequences was generated. The analysis of the lowest 10,000 protein sequences generated by Monte Carlo leads to the mutation pattern shown in FIG. 15a. Thus, any protein sequence showing mutations at the positions according to FIG. 15A will potentially generate a more stable and/or active XA protein. In particular those protein sequences found among the list of the lowest 101 MC generated sequences (data not shown) have a high potential to result in a more stable and/or active XA protein. A preferred XA sequence is shown in FIG. 15B. A DNA library can be generated to mirror the probability table of FIG. 15A that comprises at least one sequence that is more stable and/or active than wild type *Bacillus circulans* xylanase.

This PDA calculation further reduced the number of amino acids found at each position. If we consider those amino acids with a probability higher than 5%, we obtain $2.4 \times 10^6$ sequences (see FIG. 15A).

These preliminary calculations show that PDA can significantly reduce the dimensionality of the problem and can bring it into the scope of gene shuffling and screening techniques.

We claim:

1. A non-naturally occurring xylanase activity (XA) protein, wherein said protein has the sequence set forth in SEQ ID NO:3.

2. A non-naturally occurring xylanase activity (XA) protein consisting of at least four amino acid substitutions as compared to *Bacillus circulans* xylanase (SEQ ID NO:1), wherein said substitutions are selected from the amino acid residues at positions 26, 28, 30, 53, 58, 64, 79, 105, 142, 144, 171, 176, 180, and 182.

3. A non-naturally occurring xylanase activity (XA) protein consisting of amino acid substitutions at residues positions 28, 30, 58 and 144 as compared to *Bacillus circulans* xylanase (SEQ ID NO:1).

4. A bleaching agent comprising as an active ingredient an XA protein according to claims 1, 2, or 3.

* * * * *